US010004458B2

(12) United States Patent
Toth et al.

(10) Patent No.: US 10,004,458 B2
(45) Date of Patent: Jun. 26, 2018

(54) SYSTEMS AND METHODS FOR NEUROLOGICAL TRAFFIC AND/OR RECEPTOR FUNCTIONAL EVALUATION AND/OR MODIFICATION

(71) Applicant: Autonomix Medical, Inc., Excelsior, MN (US)

(72) Inventors: Landy Toth, Doylestown, PA (US); Robert Schwartz, Inver Grove Heights, MN (US)

(73) Assignee: AUTONOMIX MEDICAL, INC., Excelsior, MN (US)

( * ) Notice: Subject to any disclaimer, the term of this patent is extended or adjusted under 35 U.S.C. 154(b) by 295 days.

(21) Appl. No.: 14/780,068

(22) PCT Filed: Mar. 27, 2014

(86) PCT No.: PCT/US2014/031962
§ 371 (c)(1),
(2) Date: Sep. 25, 2015

(87) PCT Pub. No.: WO2014/160832
PCT Pub. Date: Oct. 2, 2014

(65) Prior Publication Data
US 2016/0029960 A1 Feb. 4, 2016

Related U.S. Application Data

(60) Provisional application No. 61/885,540, filed on Oct. 2, 2013, provisional application No. 61/805,523, filed on Mar. 27, 2013.

(51) Int. Cl.
*A61B 5/00* (2006.01)
*A61N 1/05* (2006.01)
(Continued)

(52) U.S. Cl.
CPC ........ *A61B 5/6851* (2013.01); *A61B 5/04001* (2013.01); *A61B 5/0488* (2013.01);
(Continued)

(58) Field of Classification Search
CPC .. A61B 18/14–18/16; A61N 1/36135–1/36189
(Continued)

(56) References Cited

U.S. PATENT DOCUMENTS 5,711,298 A   1/1998   Littmann et al.
5,957,920 A   9/1999   Baker
(Continued)

FOREIGN PATENT DOCUMENTS

WO   9636277 A1    11/1996
WO   01/22897 A1    4/2001
(Continued)

*Primary Examiner* — William Thomson
*Assistant Examiner* — Jonathan Kuo
(74) *Attorney, Agent, or Firm* — Ryan, Mason & Lewis, LLP

(57) ABSTRACT

Systems and methods for controlled sympathectomy procedures for neuromodulation are disclosed. A system for controlled micro ablation procedures is disclosed. A guidewire including one or more sensors or electrodes for accessing and recording physiologic information from one or more anatomical sites within the parenchyma of an organ as part of a physiologic monitoring session, a diagnostic test, or a neuromodulation procedure is disclosed. A guidewire including one or more sensors and/or a means for energy delivery, for performing a neuromodulation procedure within a small vessel within a body is disclosed.

31 Claims, 10 Drawing Sheets

(51) Int. Cl.
*A61B 5/04* (2006.01)
*A61B 18/14* (2006.01)
*A61B 5/0488* (2006.01)
*A61B 5/11* (2006.01)
*A61N 1/36* (2006.01)
*A61B 5/20* (2006.01)
*A61B 18/00* (2006.01)
*A61B 90/00* (2016.01)

(52) U.S. Cl.
CPC .............. *A61B 5/11* (2013.01); *A61B 5/4041* (2013.01); *A61B 5/4875* (2013.01); *A61B 5/685* (2013.01); *A61B 5/6852* (2013.01); *A61B 18/1492* (2013.01); *A61N 1/05* (2013.01); *A61N 1/36139* (2013.01); *A61B 5/201* (2013.01); *A61B 90/06* (2016.02); *A61B 2018/0016* (2013.01); *A61B 2018/0022* (2013.01); *A61B 2018/0088* (2013.01); *A61B 2018/00267* (2013.01); *A61B 2018/00404* (2013.01); *A61B 2018/00511* (2013.01); *A61B 2018/00577* (2013.01); *A61B 2018/00839* (2013.01); *A61B 2018/00875* (2013.01); *A61B 2090/064* (2016.02)

(58) Field of Classification Search
USPC .................................................. 600/372–397
See application file for complete search history.

(56) References Cited

U.S. PATENT DOCUMENTS

| | | | | |
|---|---|---|---|---|
| 6,090,052 A * | 7/2000 | Akerfeldt | ............... | H05K 1/118 600/585 |
| 6,296,619 B1 * | 10/2001 | Brisken | ............... | A61B 17/2202 600/466 |
| 7,255,695 B2 | 8/2007 | Falwell et al. | | |
| 9,649,064 B2 * | 5/2017 | Toth | ............... | A61B 5/4839 |
| 2002/0138075 A1 * | 9/2002 | Edwards | ............ | A61B 18/1477 606/41 |
| 2005/0288730 A1 | 12/2005 | Deem et al. | | |
| 2007/0208263 A1 | 9/2007 | John et al. | | |
| 2008/0027346 A1 * | 1/2008 | Litt | ............... | A61B 5/0478 600/544 |
| 2011/0034912 A1 * | 2/2011 | de Graff | ............... | H01L 29/82 606/21 |
| 2011/0306851 A1 * | 12/2011 | Wang | ................... | A61B 5/4893 600/301 |
| 2011/0307034 A1 | 12/2011 | Hastings et al. | | |
| 2015/0065945 A1 * | 3/2015 | Zarins | ................ | A61B 18/1492 604/21 |
| 2015/0289929 A1 * | 10/2015 | Toth | ................... | A61B 18/1492 600/372 |
| 2015/0297139 A1 * | 10/2015 | Toth | ...................... | A61B 18/18 600/381 |
| 2016/0082179 A1 * | 3/2016 | Toth | ................... | A61B 18/1492 600/1 |
| 2016/0213313 A1 * | 7/2016 | Toth | ................... | A61B 18/1492 |

FOREIGN PATENT DOCUMENTS

| | | |
|---|---|---|
| WO | 2011/059331 A2 | 5/2011 |
| WO | 2012100211 A2 | 7/2012 |
| WO | 2013/112844 A2 | 8/2013 |
| WO | 2013/188640 A1 | 12/2013 |
| WO | 2013181137 A1 | 12/2013 |
| WO | 2014070999 A2 | 5/2014 |
| WO | PCT/US2014/031962 | 9/2014 |

* cited by examiner

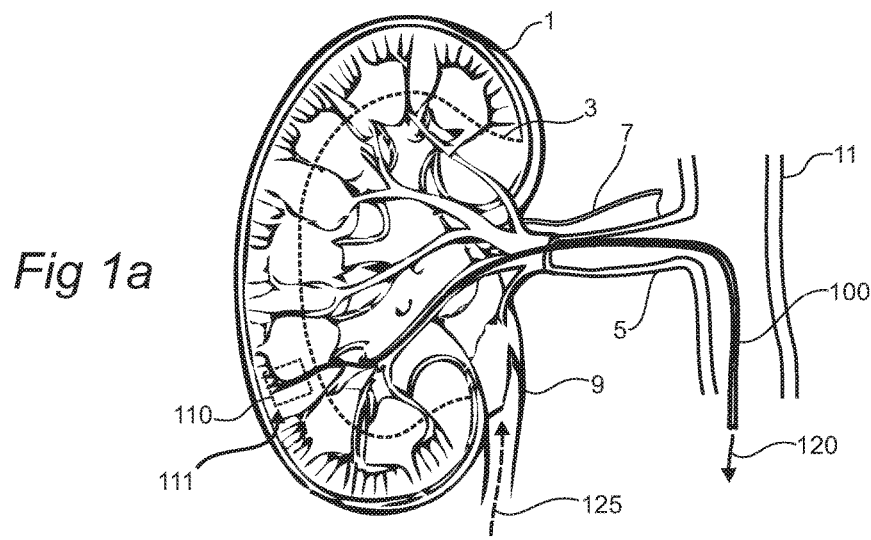
*Fig 1a*
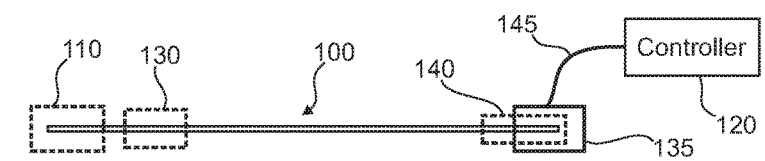
*Fig 1b*
*Fig 1c*
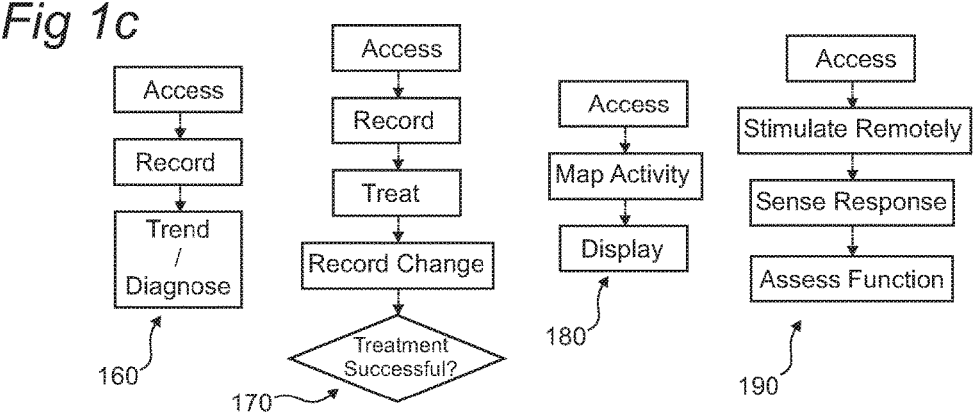
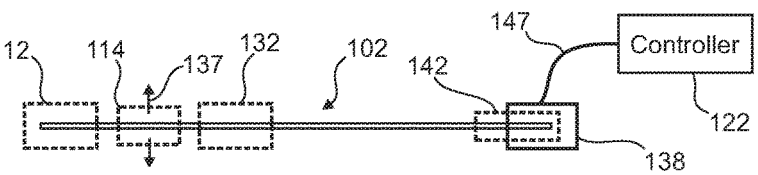
*Fig 1d*

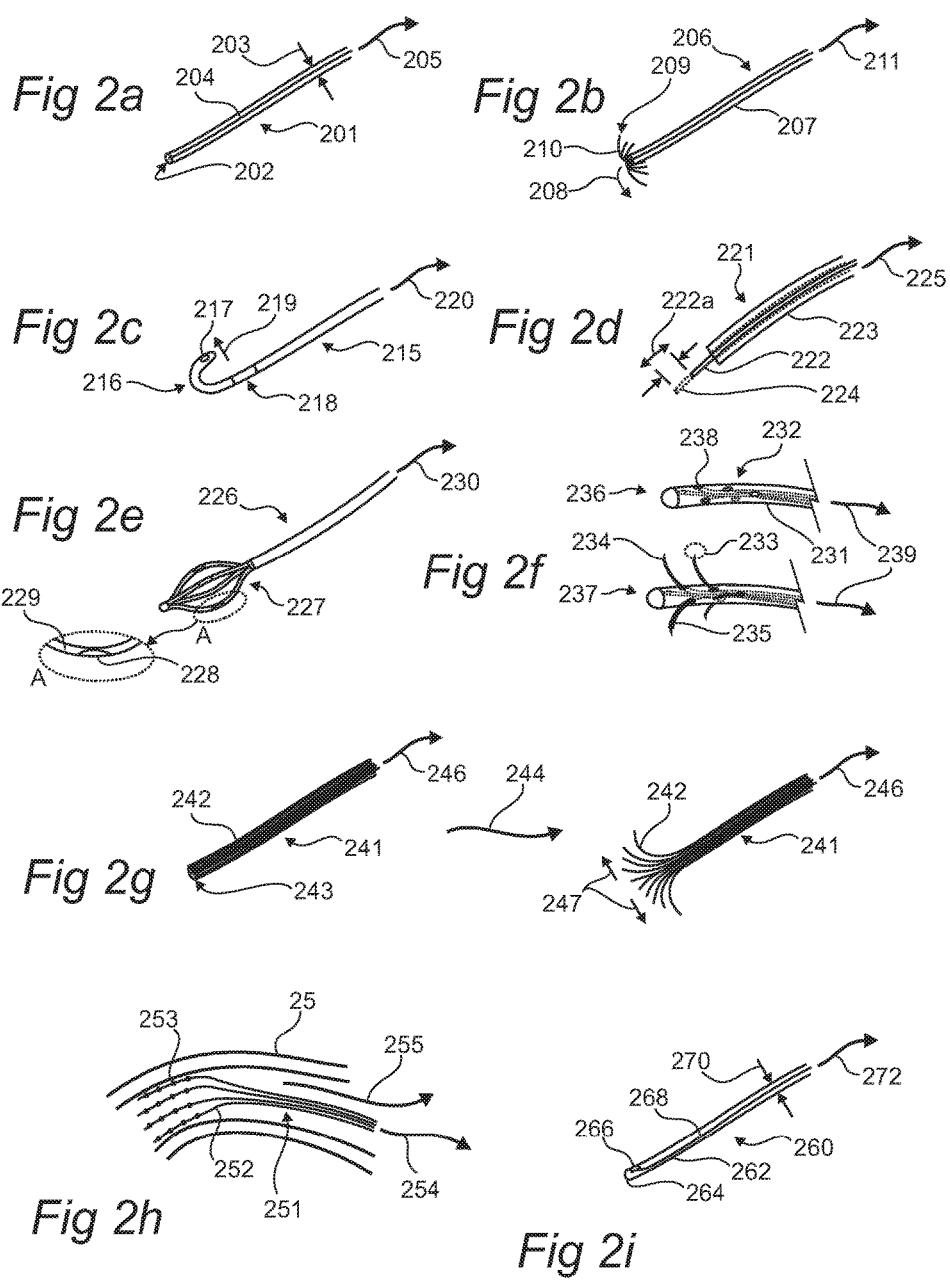

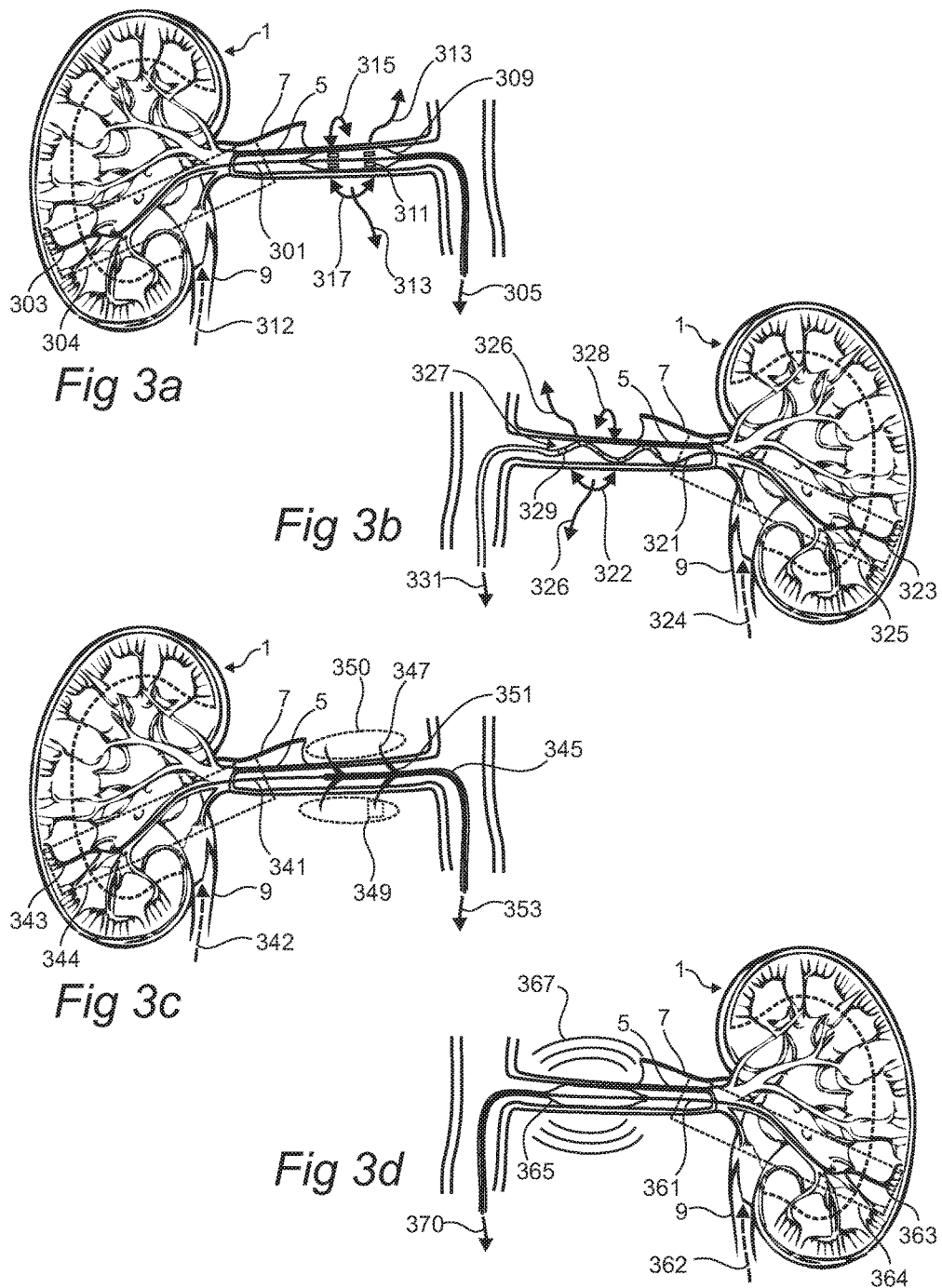

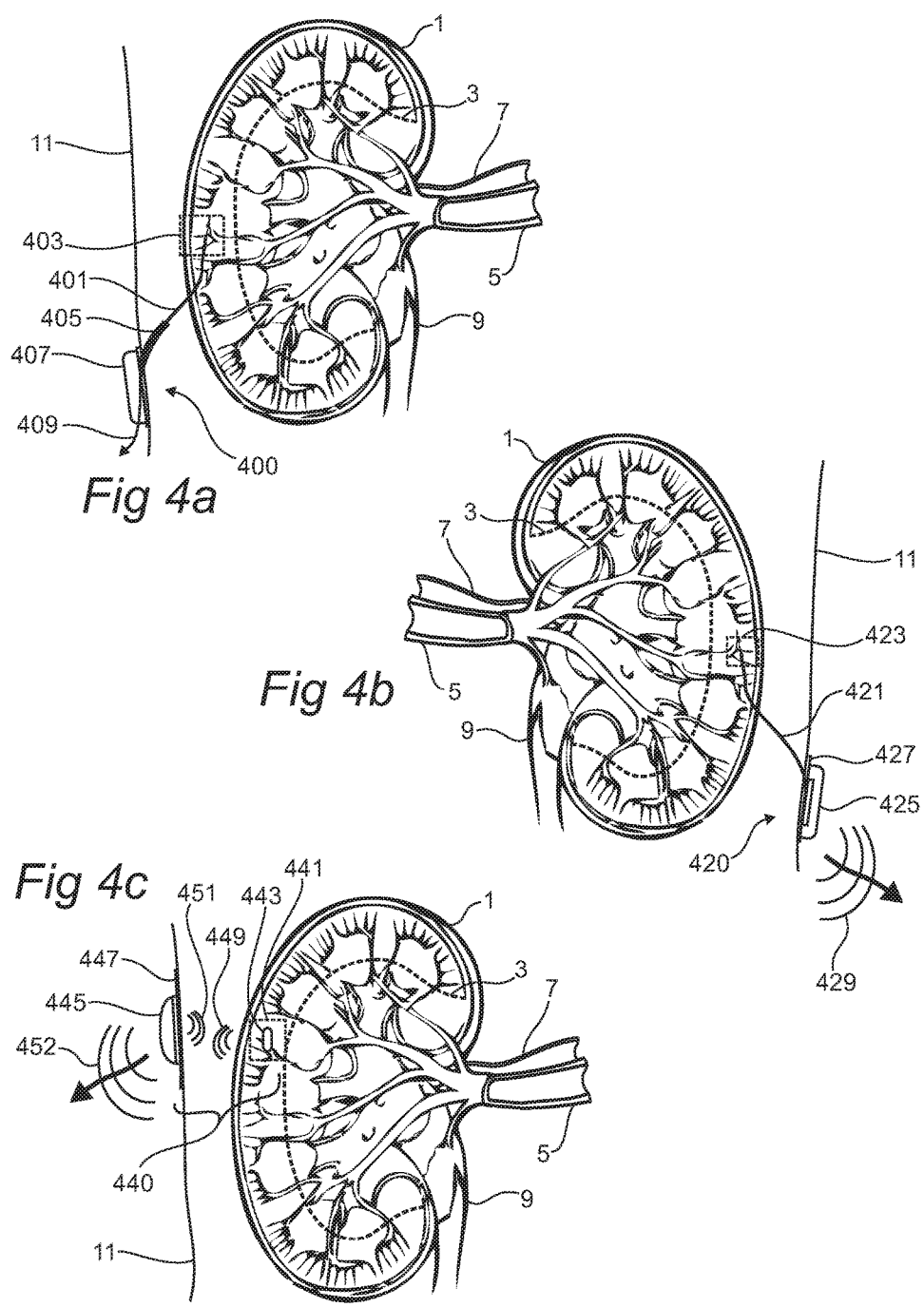

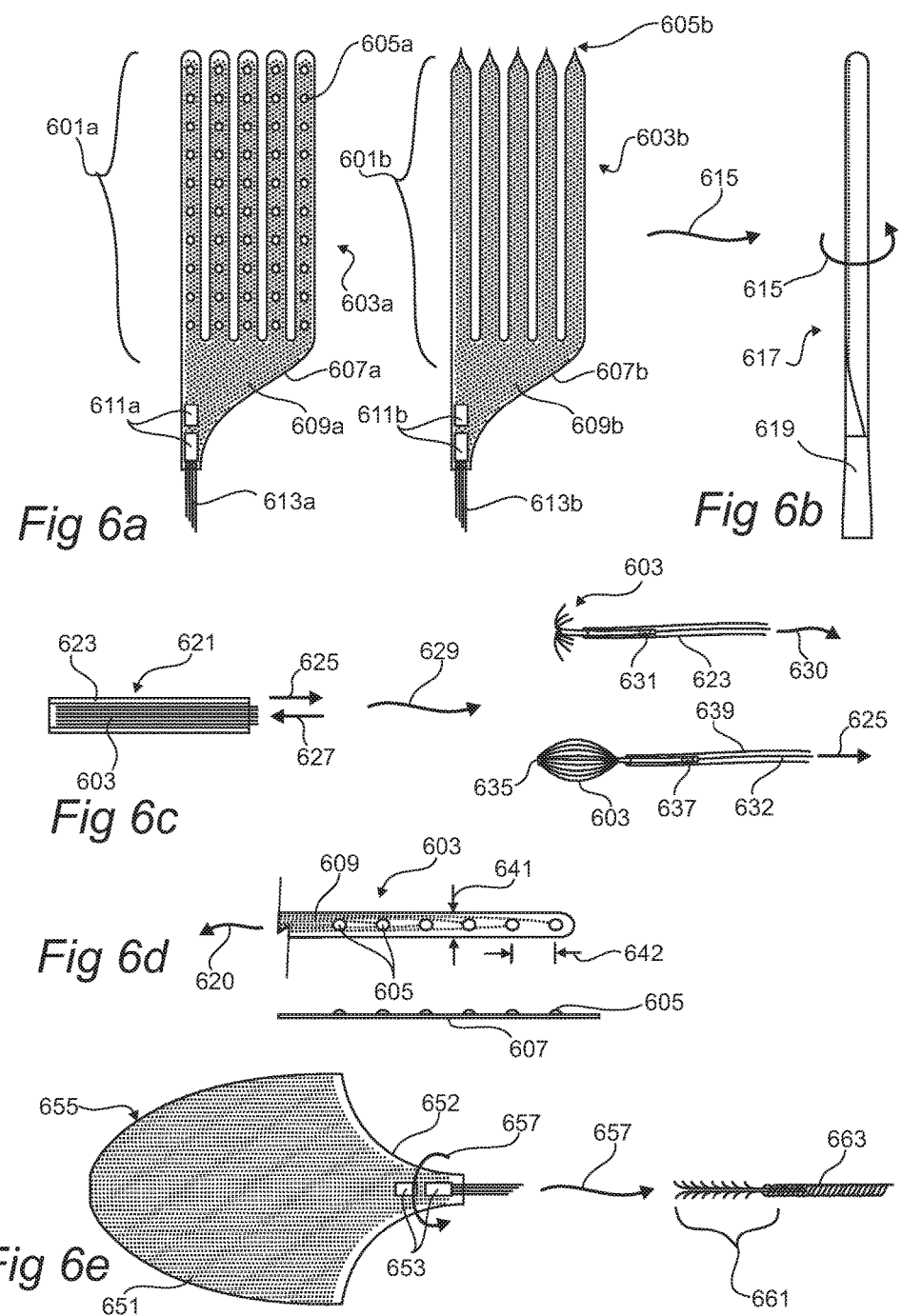

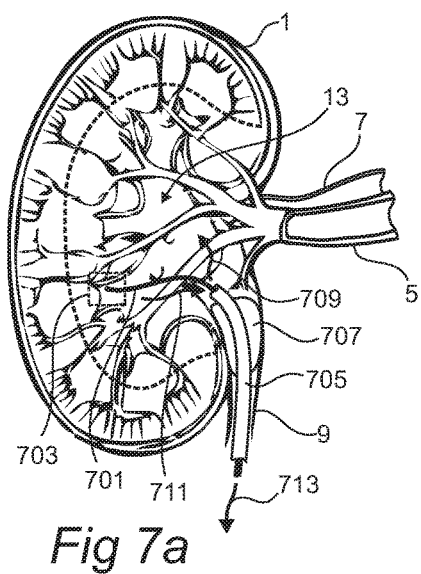
Fig 7a
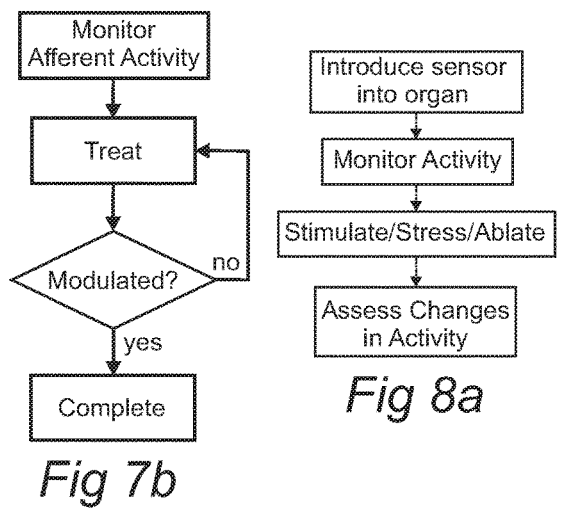
Fig 7b
Fig 8a
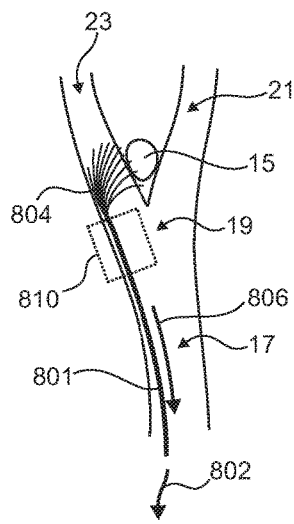
Fig 8b
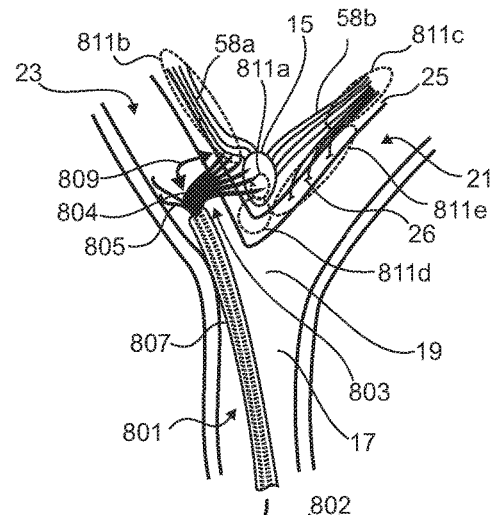
Fig 8c

SYSTEMS AND METHODS FOR NEUROLOGICAL TRAFFIC AND/OR RECEPTOR FUNCTIONAL EVALUATION AND/OR MODIFICATION

CROSS-REFERENCES TO RELATED APPLICATION

The present application is a national stage of International Application PCT/US2014/031962 which claims benefit of and priority to U.S. Provisional Application Ser. No. 61/805,523 filed on Mar. 27, 2013, entitled "Systems and Methods for Neurological traffic and/or Receptor Functional Evaluation and/or Modification", by Landy Toth et al., and U.S. Provisional Application Ser. No. 61/885,540 filed on Oct. 2, 2013, entitled "Systems and Methods for Neurological traffic and/or Receptor Functional Evaluation and/or Modification", by Landy Toth et al. the entire contents of which are incorporated by reference herein for all purposes.

BACKGROUND

Technical Field

The present disclosure relates to the field of surgical modification of neurological function as well as methods for locating, monitoring and/or mapping electrophysiological signals before, during and/or following a stimulus and/or surgical procedure, such as denervation or neuromodulation.

Background

Congestive heart failure, hypertension, diabetes, sleep apnea, and chronic renal failure have many different initial causes; however, all may include some form of sympathetic hyperactivity. Chemoreceptors, baroreceptors, stretch-receptors, and sympathetic nerves communicate signals with sympathetic centers located in the spinal cord and brain via afferent nerve activity, increasing systemic sympathetic tone; meanwhile, through efferent activity, nerves and arteries participate in sympathetic hyperactivity in response to signals from the brain, further increasing systemic sympathetic tone.

Sympathetic activation can initially be beneficial but eventually becomes maladaptive. In a state of sympathetic hyperactivity, a number of pathological events take place: abnormalities of hormonal secretion such as increased catecholamine, renine and angiotensin II levels, increased blood pressure due to peripheral vascular constriction and/or water and sodium retention, renal failure due to impaired glomerular filtration and nephron loss, cardiac dysfunction and heart failure due to left ventricular hypertrophy and myocyte loss, stroke, and even diabetes. Therefore, modulation (reduction/removal) of this increased sympathetic activity can slow or prevent the progression of these diseases.

Although ablation of such nerves can have positive effects on drug resistant hypertension and glucose metabolism abnormality, current methodologies for denervation (e.g. ablation via a range of energy sources or chemistries) are conducted without adequate feedback (with respect to the site of a denervation event, the extent of denervation, the effect of denervation on local physiology, etc.) and cases of non-responders in the clinic to treatment remains a concern.

SUMMARY

One objective of this disclosure is to provide a microsurgical tool for monitoring, evaluating the function of, mapping, and/or modulating electrophysiological activity in the vicinity of a lumen within a body. Another objective is to provide systems and methods for evaluating the extent of a neuromodulation procedure such as a neuromodulating surgery or stimulation. Another objective is to provide a sensing and/or ablating guidewire for monitoring physiologic signals, and/or performing a neuromodulation procedure in a body, particularly within or in the vicinity of the parenchyma of an organ, such as a kidney, a carotid body, a prostate, a pancreas, a liver, a stomach, an intestine, a spleen, one or more ganglia, etc. and/or the perivascular neural supply to the organ. Another objective is to provide a system and method for evaluating the sympathetic tone of a subject. Yet another objective is to provide systems and/or devices for neuromodulating an anatomical site in the vicinity of a lumen within a body. Another objective is to provide systems and/or devices for adjusting the functionality of an organ process, a receptor process, a cellular process or the like in the vicinity of a lumen within a body.

The above objectives are wholly or partially met by devices, systems, and methods according to the appended claims in accordance with the present disclosure. Features and aspects are set forth in the appended claims, in the following description, and in the annexed drawings in accordance with the present disclosure.

According to a first aspect there is provided, a microsurgical tool for monitoring electrophysiological activity within the vicinity of a lumen, the microsurgical tool including a microfinger in accordance with the present disclosure having a substantially elongate structure configured so as to bias a region thereof against a wall of the lumen upon deployment within the lumen, and a sensing tip in accordance with the present disclosure electrically and mechanically coupled to the microfinger in the vicinity of the region, configured to interface with the wall of the lumen, the sensing tip configured to convey one or more electrophysiological signals associated with the activity.

In aspects, one or more of the electrophysiological signals may be related to one or more of water concentration, tone, evoked potential, remote stimulation of nervous activity, an electromyographic signal [EMG], a mechanomyographic signal [MMG], a local field potential, an electroacoustic event, vasodilation, vessel wall stiffness, muscle sympathetic nerve activity (MSNA), central sympathetic drive (e.g. bursts per minute, bursts per heartbeat, etc.), tissue tone, nerve traffic (e.g. post ganglionic nerve traffic in the peroneal nerve, celiac ganglion, superior mesenteric ganglion, aorticorenal ganglion, renal ganglion, and/or related nervous system structures), combinations thereof, or the like.

In aspects, one or more of the sensing tips may include one or more electrodes, a needle electrode, a force sensor, mechanomyographic (MMG) sensing element, a strain sensor, a compliance sensor, a temperature sensor, combinations thereof, or the like each in accordance with the present disclosure. In aspects, one or more sensing tips may be electrically coupled with a microcircuit, the microcircuit configured to condition the signal.

In aspects, a system/surgical tool in accordance with the present disclosure may be used to access, monitor, and/or to treat one or more sensory receptors: Ampullae of Lorenzini (respond to electric field, salinity, temperature, etc.), baroreceptors, chemoreceptors, hydroreceptors, mechanoreceptors, nociceptors, osmoreceptors (osmolarity sensing), photoreceptors, proprioceptors, thermoreceptors, combinations thereof, and the like.

According to aspects there is provided, an elongate medical device including one or more sensing tips each in accordance with the present disclosure. The elongate medical device may be configured for placement within a vessel, for delivery to or within the parenchyma of an organ into which the vessel extends.

In aspects, the elongate medical device may be a guidewire configured for nerve monitoring, electrophysiological monitoring, stimulation, and/or ablation procedures.

In aspects, a guidewire in accordance with the present disclosure may be configured to provide a path over which a second surgical tool may be delivered to the vessel, the guidewire sensing tip configured to monitor one or more physiologic functions relevant to the operation and/or evaluation of a procedure performed by the surgical tool.

In aspects, a guidewire and/or sensing tip in accordance with the present disclosure may be dimensioned and configured for placement into the parenchyma of an organ, a renal cortex of a kidney, an adrenal gland, a vessel connected with the adrenal gland, an adrenal medulla, and/or a renal pelvis of a kidney.

In aspects, a guidewire in accordance with the present disclosure may include a plurality of zones arranged along the length thereof, each zone configured for sensing local electrophysiological activity, stimulating local neural anatomy, and/or neuromodulating local neural anatomy (e.g. ablating, denervating, etc.). In aspects, a guidewire in accordance with the present disclosure may include a sensing zone located at the distal tip thereof, an ablating/stimulating zone located along the length of the guidewire proximally to the distal tip, and a second sensing zone located along the length of the guidewire proximally to the ablating/stimulating zone. In aspects, functions performed within each zone during a procedure may be coordinated by a controller in accordance with the present disclosure for purposes of diagnosis, determining the extent of a procedure, performing a neuromodulation procedure, denervating a neural structure, combinations thereof, or the like.

In aspects, a guidewire in accordance with the present disclosure may be sized with a diameter of less than 1 mm, less than 0.75 mm, less than 0.5 mm, less than 0.25 mm, etc. In aspects, the guidewire may be configured with a shape set region, configured to bias one or more regions of the guidewire against a wall of a lumen into which it has been placed. In aspects, the guidewire may include a wire basket, a helical region, a balloon, etc. in order to provide such bias against an adjacent lumen wall. In aspects, the shape set region may be retractably collapsible into a delivery sheath (i.e. a sheath provided over the guidewire sized and dimensioned for delivery thereof to an anatomical site of interest). In aspects, the shape set region may be deployed so as to bias against a wall of a lumen into which it is placed by an actuation procedure, retraction of a delivery sheath, protrusion of the guidewire distal tip beyond the distal tip of a delivery sheath, etc.

In aspects, a guidewire in accordance with the present disclosure may include a bulbous feature located within the vicinity of the distal tip thereof, the bulbous feature configured to bottom out the guidewire within a lumen (e.g. when the lumen diameter approaches that of the bulbous feature, between a step between a feeding lumen and a treatment lumen, etc.). Such a feature may be advantageous to position the distal tip of the guidewire within a treatment lumen (e.g. a vessel, an artery, a vein, a tubule, etc.), to provide hemostasis to the treatment lumen, etc.

In aspects, a guidewire in accordance with the present disclosure may include a microelectronic circuit embedded within or coupled to the distal tip thereof, as well as coupled to an interconnect and/or controller coupled to the proximal end thereof, configured to control signal flow to/from one or more zones of the guidewire for purposes of performing a procedure in accordance with the present disclosure.

According to aspects there is provided, a method for treating an anatomical site within a body, including imaging the anatomical site (e.g. with a computed tomography system, high-resolution computed tomography (HRCT), magnetic resonance imaging (MRI), functional magnetic resonance imaging (fMRI), positron emission tomography, ultrasound, optical coherence tomography (OCT), combinations thereof, or the like) to produce one or more images (e.g. 2D images, 3D images, etc.) thereof, guiding a guidewire, device, and/or aspects of a system in accordance with the present disclosure to within the vicinity of the anatomical site (optionally in combination with the images), and performing a procedure, and/or treating the anatomical site (e.g. via ablation, chemical delivery, energy delivery, etc.). In aspects, the procedure may include sensing one or more physiologic aspects of the anatomical site and/or a bodily process related thereto, stimulating the anatomical site, etc.

In aspects, a method in accordance with the present disclosure may include advancing a guidewire in accordance with the present disclosure until it "bottoms out" against the walls of the lumen including and/or coupled to the anatomical site.

In aspects, a method in accordance with the present disclosure may include releasing a chemical substance in accordance with the present disclosure into, through the wall of, and/or into the adventitia around a lumen coupled with the anatomical site, and/or associated organ.

In aspects, a method in accordance with the present disclosure may include monitoring one or more physiologic processes with the distal tip of a guidewire in accordance with the present disclosure, before, during, and/or after the release of the chemical substance. The method may include assessing the efficacy of a procedure (e.g. ablation, chemical release, chemical ablation, RF ablation, ultrasound ablation, hypothermic ablation, radiosurgical ablation, etc.). In aspects, the method may include inducing a temporary neural block, monitoring the effects of the temporary neural block, and/or creating a substantially long term neural block depending on the monitoring.

In aspects, a guidewire in accordance with the present disclosure may include one or more electrodes, each electrode configured to sense, stimulate, and/or ablate a local anatomical site within a body. In aspects, the guidewire may include a plurality of ablation electrodes configured to interface with a wall of a lumen into which the guidewire is placed, so as to provide coupling for delivery of radiofrequency, and/or microwave frequency energy into the wall of the lumen and/or tissues surrounding the lumen, as part of a procedure in accordance with the present disclosure. In aspects, the guidewire may be configured to monitor one or more physiologic aspects in conjunction with the energy delivery process (e.g. before, during, after, etc.).

In aspects, a system in accordance with the present disclosure may include a delivery catheter including one or more electrodes, and a guidewire including one or more electrodes, the system configured to pass energy between the catheter electrode(s) and the guidewire electrode(s) as part of a procedure. In aspects, the system may be configured to monitor electrophysiological activity between the guidewire electrode(s) and the catheter electrode(s) as part of a procedure.

In aspects, a guidewire in accordance with the present disclosure may include a drug eluting region (e.g. over an electrode, at the distal tip, etc.), configured so as to elute a drug into the vicinity of the region during a procedure (e.g. so as to minimize clotting, minimize damage to adjacent structures, etc.).

In aspects, a guidewire in accordance with the present disclosure may include a thrombus net coupled to the distal tip thereof. The thrombus net may be configured so as to bridge a cross section of a lumen into which the guidewire is placed during a procedure. The thrombus net may be configured to capture debris generated at a site along the system, guidewire, associated catheter, etc. during a procedure in accordance with the present disclosure. The thrombus net may be configured so as to withdraw any captured debris along with the guidewire during withdrawal from the body.

In aspects there is provided a guidewire for monitoring electrophysiological activity in the vicinity of an anatomical site of interest within the vicinity of a lumen within a body, the guidewire including an elongate body dimensioned for insertion into the lumen, and a sensing tip electrically and mechanically coupled to the elongate body, configured to interface with the wall of the lumen, the sensing tip configured to convey one or more electrophysiological signals associated with the activity.

In aspects, the sensing tip may include one or more sensors and/or electrodes each in accordance with the present disclosure. The sensor and/or electrode dimensioned and configured to interface with the anatomical site of interest upon placement thereby.

In aspects, the sensing tip may include one or more sensors configured to measure one or more electrophysiological signals related to one or more of water concentration, tone, evoked potential, remote stimulation of nervous activity, an electromyographic signal [EMG], a mechanomyographic signal [MMG], a local field potential, an electroacoustic event, vasodilation, vessel wall stiffness, muscle sympathetic nerve activity (MSNA), central sympathetic drive, tissue tone, nerve traffic, combinations thereof, or the like.

In aspects, a sensing tip in accordance with the present disclosure may be dimensioned for placement into the parenchyma of an organ coupled with the lumen (e.g. into a liver, a prostate, a pancreas, a spleen, a bladder, a prostate, a ganglion, a gland, into a renal cortex of a kidney, an adrenal gland, an adrenal medulla, an adrenal cortex, and/or a renal pelvis of a kidney, combinations thereof, or the like).

In aspects, the sensing tip may be configured such that the sensor and/or the electrode included therein may be substantially isolated from a fluid within the lumen upon deployment of the sensing tip within the lumen, maintains contact with a wall of the lumen during a procedure upon deployment of the sensing tip within the lumen, substantially maintains contact with the wall of the lumen while the sensing tip is dragged along the interior thereof, after deployment of the sensing tip within the lumen, and/or may be embedded into a wall of the lumen upon deployment of the sensing tip within the lumen.

In aspects, the guidewire may be coupled to a second surgical device, the second surgical device configured to perform an ablation, stress, and/or stimulation procedure within the body.

In aspects, the second surgical device may include a reference electrode electrically coupled with one or more of the sensors and/or electrodes included within the guidewire.

In aspects, a guidewire in accordance with the present disclosure may include a microcircuit coupled to the sensing tip, configured to convey one or more sensed physiologic signals to a proximal end of the guidewire, to condition the signal, to perform a digital conversion of the signal, to multiplex signals from a plurality of sensors and/or electrodes within the guidewire.

In aspects, a guidewire in accordance with the present disclosure may include one or more electrodes electrically and mechanically coupled with the elongate body, configured to deliver energy to the anatomical site of interest upon placement thereby.

In aspects, the guidewire may include one or more microneedles slidingly coupled with the elongate body, configured so as to be deployed beyond the elongate body into the anatomical site of interest upon placement thereby. Such a microneedle may include a lumen through which a substance may be delivered to the anatomical site of interest upon deployment of the microneedle there into. Some non-limiting examples of substances include a neurotoxin, a cancer treating agent, a neuroblocking agent, a neurostimulating agent, a neurodepressant, a vasodilator, a vasoconstrictor, glucose, insulin, a combination thereof, a formulation of the substance with a delivery vehicle, or the like.

In aspects, one or more of the microneedles may include one or more electrodes for sensing, stimulating, and/or ablating the anatomical site of interest upon deployment of the microneedle there into.

According to aspects there is provided, use of a guidewire in accordance with the present disclosure, to monitor electrophysiological activity in the vicinity of a vessel, an artery, a vein, a renal artery, or a hepatic artery, or the like.

According to aspects there is provided, use of a guidewire in accordance with the present disclosure to monitor electrophysiological activity in the parenchyma of an organ, a kidney, a renal cortex, a gland, an adrenal gland, a liver, a pancreas, a spleen, a prostate, or a renal pelvis, an arteriole, venule, or vesicle associated therewith, or the like.

According to aspects there is provided, use of a guidewire in accordance with the present disclosure to perform and/or monitor a neuromodulation procedure.

According to aspects there is provided, use of a guidewire in accordance with the present disclosure, to evaluate a sympathetic and/or parasympathetic activity level associated with an organ, a process associated with the organ, or a region thereof within a body.

According to aspects there is provided, a system for neuromodulating an anatomical site in the vicinity of a lumen, including a subsystem configured to perform a surgical procedure on the anatomical site, a guidewire in accordance with the present disclosure, configured to monitor electrophysiological activity within the parenchyma of an organ coupled to the lumen and to generate one or more signals therefrom, and a control unit configured to accept signals from the guidewire, and to adjust the surgical procedure dependent upon the signals, to display the signals (e.g. to an operator, a subject, a client, etc.), to evaluate the surgical procedure dependent upon the signals, to plan a surgical path dependent upon the signals, and/or to determine the extent of the procedure dependent upon the signals, or the like.

In aspects, the surgical procedure may comprise an ablation, an excision, a cut, a burn, a radio frequency ablation, radiosurgery, an ultrasonic ablation, a cryoablation, an abrasion, a biopsy, delivery of a substance, a combination thereof, or the like.

In aspects, the system may include a stimulation and/or ablation electrode configured so as to convey a pulsatile and/or radio frequency signal to the anatomical site from the control unit, the guidewire configured to convey one or more feedback signals related to the pulsatile and/or radio frequency signals back to the control unit. Such feedback signals may be related to electrode impedance, a bioimpedance, a local electrical field, or an electrophysiological response to the pulsatile and/or radio frequency signal, or the like. In aspects, the stimulation and/or ablation electrode may be included within the guidewire and/or a sensing tip thereof.

In aspects, the subsystem may be situated coaxially with the guidewire in the lumen.

In aspects, the system may include a sensor to measure one or more physiologic signals associated with a body comprising the lumen, and to convey the physiologic signals to the control unit for use in the procedure. The sensor may be configured to measure one or more of water concentration, tone, blood oxygen saturation of local tissues, evoked potential, stimulation/sensing of nervous activity, electromyography, temperature, blood pressure, vasodilation, vessel wall stiffness, muscle sympathetic nerve activity (MSNA), central sympathetic drive, tissue tone, blood flow, a blood flow differential signal, blood perfusion, pupil dilation, electrolyte levels in a biofluid, a blood analyte level, nerve traffic, a combination thereof, or the like.

According to aspects there is provided, a method for evaluating sympathetic tone of a subject including, recording electrophysiological signals from a lumen and/or from one or more sites within an organ of the subject, and generating a metric relating to sympathetic tone from the recorded signals.

In aspects the recording may be at least partially facilitated by a guidewire in accordance with the present disclosure.

The method may include applying a stress test to the subject during the recording. The stress test may include having the subject perform a valsalva maneuver, a tilt table test, elevating one or more legs, transient sitting to standing exercises, execute a change in posture, move from a prone position to a sitting or standing position, a breath hold technique, or combinations thereof. In aspects, the stress test may include injecting into the subject a vasodilator, a vasoconstrictor, a neuroblocker, a neurostimulant, a diuretic, insulin, glucose, beta-adrenergic receptor antagonist, angiotensin-II converting enzyme inhibitor, calcium channel blocker, an HMG-CoA reductase inhibitor, digoxin, an anticoagulant, a diuretic, a beta blocker, an ACE inhibitor, a steroid, combination thereof, or the like. In aspects, such an injection may be made into the lumen and/or into the organ. In aspects, the injection may be performed at least in part by a guidewire in accordance with the present disclosure.

In aspects the metric may be generated from recordings taken while the subject is awake or asleep, assessment while awake versus under anesthesia, before, during and/or after electrostimulation at one or more sites on the subject, combinations thereof, or the like.

In aspects, the stress test may include having the subject perform a physical activity, altering the blood volume of the subject, altering the heartbeat of the subject, injecting a quantity of saline into the subject, or a combination thereof.

In aspects, the method may include evaluating how the activity responds to the stress test, comparing the response to a previous stress test performed on the subject, comparing the response to a population average response to the stress test, comparing aspects within a single stress test, comparing the activity before and after a procedure, comparing the activity between a resting state and an active state, comparing activity between an awakened state and a sleeping state, or combinations thereof.

In aspects, the method may include neuromodulating one or more anatomical sites within the subject.

The method may include inserting a balloon catheter into a lumen coupled to the organ and temporarily blocking the lumen, applying a polarizing potential to one or more sites in the organ and/or the lumen wall, monitoring another physiologic parameter remotely from the lumen to generate a corrective signal and using the corrective signal to remove movement artifacts from the electrophysiological signals, stimulating one or more anatomical sites in the subject during the recording, and/or diagnosing a medical condition based at least in part upon the metric.

According to aspects there is provided, a method for determining the properties of one or more neurological features in the vicinity of one or more monitoring sites, including monitoring one or more of water concentration, tone, blood oxygen saturation of local tissues, evoked potential, stimulation/sensing of nervous activity, electromyography, temperature, blood pressure, vasodilation, vessel wall stiffness, muscle sympathetic nerve activity (MSNA), central sympathetic drive, tissue tone, blood flow (e.g. through an artery, through a renal artery), a blood flow differential signal, blood perfusion, pupil dilation, electrolyte levels in a biofluid, a blood analyte level, nerve traffic, or combinations thereof, at one or more of the monitoring sites to generate one or more physiologic signals, applying a stress test to the subject, and evaluating the physiologic signals obtained from each monitoring site to determine an anatomical map therefrom, a physiologic response to the stress test, or the like.

The method may include using the anatomical map or physiologic response to selectively ablate one or more of the sites.

The method may include determining if a monitoring site includes substantially more sympathetic or parasympathetic neurological features, and/or applying energy in the vicinity of the lumen so as to induce a neurological block in the vicinity thereof. In aspects, the method may include comparing the physiologic signals obtained before the neurological block to those obtained during the neurological block to determine the influence of the neurological block there upon, and optionally determining if the neurological block is favorable in terms of treating an underlying disease state in the body. In aspects, the method may include applying energy in the vicinity of the lumen so as to induce a substantially permanent neurological block in the vicinity of selected monitoring sites.

According to aspects there is provided, use of a method in accordance with the present disclosure for evaluation of the effectiveness of a neuromodulation procedure within a body.

BRIEF DESCRIPTION OF THE DRAWINGS

Several aspects of the disclosure can be better understood with reference to the following drawings. In the drawings, like reference numerals designate corresponding parts throughout the several views.

FIGS. 1a-d show aspects of a guidewire in accordance with the present disclosure.

FIGS. 3a-d show aspects of a sensing guidewire in accordance with the present disclosure coupled with a second surgical tool or system for monitoring locations in a body before, during and/or after a surgical procedure.

FIGS. 4a-c show devices in accordance with the present disclosure placed so as to monitor activity within an organ within a body.

FIGS. 6a-e show aspects of flexible multi-electrode guidewire tips in accordance with the present disclosure.

FIGS. 7a-b show a guidewire and surgical device each in accordance with the present disclosure, positioned within an organ within a body.

FIGS. 8a-c show aspects of a device in accordance with the present disclosure configured and dimensioned to interface with a carotid body.

DETAILED DESCRIPTION

Figure 2J:
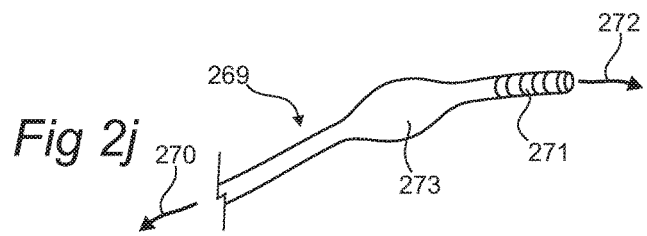
FIGS. 2a-p show aspects of guidewire tips associated with a guidewire in accordance with the present disclosure.

Particular embodiments of the present disclosure are described hereinbelow with reference to the accompanying drawings; however, the disclosed embodiments are merely examples of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

According to a first aspect there is provided a controlled nerve ablation system, which may include the capability to sense one or more physiologic parameters at one or more points in the vicinity of a surgical site or within an affected organ, as well as include the capability to stimulate and/or ablate tissues at one or more of the same points and/or an alternative point in the vicinity of a surgical site. The nerve ablation system may be configured so as to access vessels and/or surgical sites in the body. The non-limiting examples disclosed herein may be directed towards such configurations (e.g. to controllably provide neuromodulation procedures to an organ within a body, so as to controllably ablate renal nerves along a renal artery via an endoscopic or percutaneous procedure, etc.). Such non-limiting examples are meant to serve as guidance that may be applied to other treatment sites within a body, disease states, etc.

By surgery/surgical is meant, a surgical procedure, an interventional procedure, a minimally invasive procedure, and the like.

Some non-limiting examples of medical conditions that can be treated according to the present disclosure include genetic, skeletal, immunological, vascular or hematological, muscular or connective tissue, neurological, ocular, auditory or vestibular, dermatological, endocrinological, olfactory, cardiovascular, genitourinary, psychological, gastrointestinal, respiratory/pulmonary, neoplastic, or inflammatory medical conditions. Further, the medical condition can be the result of any etiology including vascular, ischemic, thrombotic, embolic, infectious (including bacterial, viral, parasitic, fungal, abscessal), neoplastic, drug-induced, metabolic, immunological, collagenic, traumatic, surgical, idiopathic, endocrinological, allergic, degenerative, congenital, or abnormal malformational causes.

The present systems and methods also encompass enhancing the therapeutic effects of other therapies, such as methods and systems working in conjunction with a pharmaceutical agent or other therapies to augment, enhance, improve, or facilitate other therapies (adjunctive therapies) as well as reducing/minimize and counteracting side effects, complications and adverse reactions for any therapies involved in treating the above-mentioned medical conditions.

In aspects, one or more functions of a liver may be augmented by a treatment and/or method, and may be monitored, examined, or evaluated (including response to a stress test, resting state, transient change in an analyte, etc.), and/or monitored in accordance with the present disclosure include glucose storage/release mechanisms, metabolic sensing/response (and related signal traffic to the brain related thereto), glucoregulatory function, afferent vagal activity reaching the brain, chemoreceptor function (or related signal traffic associated therewith), lipid sensing/synthesis, regulation of hepatic insulin sensitizing substance, afferent traffic augmentation associated with glucosensors (e.g. primarily in the region of the portal vein, etc.), protein sensing, GLP-1, leptin, CCK, FFA, PPAR alpha and gamma, glycogenolysis, gluconeogenesis, VLDL secretion, ketogenesis, hypoglycemia sensing, combinations thereof, or the like.

In aspects, one or more guidewires, surgical systems, methods, or the like each in accordance with the present disclosure may be used to influence, and/or treat cancer progression relating to a perineural invading cancer, such as cancer of the prostate, pancreas, breast, cervix, ovaries, bladder, or combinations thereof. Such treatments may be used to treat pain associated with cancer to slow, to reverse, and/or to prevent perineural invasion of a cancerous tumor into a surrounding neural microenvironment to interrupt, decrease, influence the microenvironment and/or inflammation of tissues in the state of a cancerous tumor, and/or stop neural communication to/from a cancerous tumor and/or the microenvironment surrounding the tumor to a remote site within a body.

In aspects, a system/surgical tool in accordance with the present disclosure may be used to access, monitor, and/or to treat one or more neurological pathways, ganglia, and/or sensory receptors within a body: Ampullae of Lorenzini (respond to electric field, salinity, temperature, etc.), baroreceptors, chemoreceptors, hydroreceptors, mechanoreceptors, nociceptors, osmoreceptors (osmolarity sensing), photoreceptors, proprioceptors, thermoreceptors, combinations thereof, and the like. Such receptors may be associated with one or more organs and/or physiologic processes within the body (e.g. a regulatory process, etc.).

In aspects, a surgical tool in accordance with the present disclosure may take the form of a guidewire. The guidewire may be dimensioned and configured for placement within a lumen of a body at and/or beyond a surgical site and/or anatomical site of interest, so as to monitor one or more physiologic signals near the tip thereof. In aspects, the guidewire may provide a pathway for delivery of a second surgical device to the surgical site.

In aspects, a guidewire in accordance with the present disclosure may include one or more energy delivery means for delivering energy to an anatomical site within and/or beyond the wall of a lumen into which the guidewire tip has been placed.

In aspects, a guidewire in accordance with the present disclosure may include one or more sensors (e.g. as located on a micro-tool-tip, a clamp, a hook, a wire element, an electrode in a matrix, etc.) near to the tip thereof. One or more sensors may include a pressure sensor, a tonal sensor, a temperature sensor, an electrode (e.g. to interact with a local tissue site, provide a stimulus thereto, measure a potential therefrom, monitor current to/from the tissues, to measure a bioimpedance, measure an evoked potential, an electromyographic signal [EMG], an electrocardiographic signal [ECG], an extracellular potential electrode, a mechanomyographic signal [MMG], etc.), an acoustic sensor, an oxygen saturation sensor, or the like.

In aspects, a guidewire in accordance with the present disclosure may include one or more analyte sensors, configured to measure one or more analyte concentrations or concentration trends before, during, and/or after a procedure within a body. Such analyte sensors may be provided in an electrochemical form, a fluorescent form, an electro-optical form, a swelling responsive gel, etc.

A sensing guidewire in accordance with the present disclosure may be advantageous for accessing very small anatomical sites within a body, accessing adjunct arteries and/or arteriole pathways along a blood supply to a target organ, accessing a plurality of vessels coupled to an organ, accessing the parenchyma of an organ, for highly localized interaction with a tissue site, for accessing otherwise challenging lumens (e.g. a lumen with substantially small diameter, with substantially tortuous shape, etc.). In aspects, a guidewire in accordance with the present disclosure may provide a means for directing one or more additional tools to a surgical site within a body. In aspects, a guidewire in accordance with the present disclosure may be configured to sense physiologic parameters from and/or to treat tissues within such miniature lumens as part of a procedure (e.g. a surgical procedure, a diagnostic procedure, an ablation procedure, etc.).

In aspects, one or more of the sensors included on the guidewire and electronics associated therewith may be configured to elucidate a range of key physiologic aspects during a procedure. The following description outlines some non-limiting approaches in this respect.

Bioimpedance between one or more electrodes situated on the surgical tool (and optionally a remote electrode), may be used to determine the degree of contact between one or more of the electrodes and an adjacent anatomical site, a tissue state near to one or more of the electrodes, water content of tissues in the vicinity of one or more of the electrodes, and/or potentially estimate the bias force between the electrode and the anatomical site. Additionally, alternatively, or in combination, bioimpedance measurements between one or more electrodes may be useful in determining when adequate contact has been made with the wall of lumen against which the sensor has been biased as well as how much current may be applied to an anatomical site during a surgical procedure (e.g. ablation, RF ablation, etc.). Additionally, alternatively, or in combination bioimpedance between one or more electrodes may be used to determine the status of tissue positioned there between. In aspects, the bioimpedance spectrum between two or more electrodes arranged along the surgical tool or between coordinating tools may be used to map the local tissue impedance. Such information may be useful to elucidate where such tissue has been completely ablated, where tissue has yet to be ablated, etc.

In aspects, bioimpedance measurements may be correlated with nerve damage data, obtained during prior surgeries, during development of the procedure, and/or obtained during specific testing procedures, such that changes in local bioimpedance data may be used during a surgical procedure to determine the extent of the ablation procedure. Such a configuration may be advantageous in the case that the surgical procedure itself overwhelms the local electrophysiological activity to the extent that neurological monitoring may be hindered for a prolonged period of time after the procedure has been completed.

Mechanomyographic information may be obtained from one or more sensing tips in accordance with the present disclosure during a procedure as determined by slight changes in an associated strain measurement, tip vibration, and/or contact force measurement (e.g. via direct force measurement between the tip and the local anatomy, and/or via changes in the deformation of the surgical tool tip as measured by an associated micro strain gage attached thereupon). Mechanomyographic information may be related to local nervous activity either naturally occurring or in response to a stimulus (e.g. optionally applied by one or more sensory tips, locally, remotely, during and/or via a local RF pulse, etc.). The tip of a surgical device in accordance with the present disclosure may be equipped with a piezoresistive strain gauge, a piezoelectric microtransducer, an interfacial pressure sensing membrane or the like to detect mechanomyographic signals. In aspects, the surgical tool tip may be coated with a micro or nano coating of a piezoresistive and or piezoelectric material (e.g. a piezoelectric polymer, an electret, a nano-particulate filled elastomer, etc.). In aspects, the mechanomyographic tip may be configured so as to measure one or more aspects of the tissue compliance of the local tissues (e.g. so as to identify calcified material, cancerous tissues, etc.).

In aspects, electrophysiological monitoring at or between one or more electrodes integrated into the surgical tool, may be used to monitor and/or to map nervous response, electromyographic response (EMG), evoked potential, single or multi-unit neural traffic, etc. along the wall of the local anatomy (e.g. vessel wall, the outside of a vessel wall, within an associated tubule, ureter, artery, vein, arteriole, venule, within the parenchyma of an organ, etc.). Such information may be advantageous for selecting tissues on which to perform a surgical procedure (e.g. an ablation procedure, a biopsy, a drug delivery procedure, a selective ablation procedure, etc.), to follow and/or map a nerve along the length of the surgical site (e.g. along the wall of an artery, a vein, a tubule, etc.), to monitor electrophysiological function before, during, and/or after a surgical procedure, or the like. In aspects, local electric field potentials (EFP) may be monitored before, during and/or after a surgical procedure as a means for monitoring local nervous activity. Thus EFP signals may be used as feedback for monitoring the extent of a denervation procedure.

In aspects, one or more electrodes may be configured to monitor local electrical fields during an ablation procedure in order to better determine the current flow path through the adjacent anatomy, connected to a warning system to indicate to an operator when the ablation field is insufficient for achieving the intended goal, etc. Such a configuration may be advantageous for avoiding unnecessary damage to the tissues during a misfired ablation session, etc.

In aspects, the tone (e.g. mechanical properties, wall stiffness, elastic spectral response, mechanical impedance, physiologic properties, etc.) of the adjacent tissues may be determined by combining strain and/or force measurement of sensors integrated into the surgical tool while applying movement (optionally cyclical or oscillatory movement) to one or more sensor tips while biased against the adjacent tissues. Such a surgical tool may include means for applying a local excitation (e.g. such as by a local piezoelectric transducer, a capacitive transducer, an electrochemical transducer, etc.) to one or more of the sensors or globally (e.g. such as by transverse oscillations, axial oscillations, general oscillations of the surgical tool tip, the clamp, the hook, the loop, etc.).

In aspects, one or more surgical tool tips may be interfaced with the associated tissues at an acute angle. By acute angle is meant such that the surgical tool tip approaches the associated tissue surface at an angle other than perpendicular thereto. A local excitation may be applied with relatively small amplitude so as not to generate substantial relative movement between the tissue and the tip during the excitation process (e.g. such that the transverse contact forces remain below the slip conditions between the tip and the tissue, such that they move together during excitation). By relatively small is meant an excitation that is sufficiently small in amplitude such that the sensing tip may not appreciably slide along the tissue surface. In aspects, a vibratory exciter included in the sensory tip, or in a structure attached thereto, may be configured to generate the excitation.

Such a tone monitor may be combined with interfacial contact sensing and/or sensor tip strain measurement in order to generate a wealth of local tissue information during a surgical procedure. In aspects, the local tissues may stiffen during an ablation procedure. By monitoring local tissue tone, a stiffness level may be used to characterize when a suitable degree of ablation has been applied so as to irreversibly damage the tissues. Monitoring of a local tissue tone at a monitoring site significantly removed from the surgical site such that the surgical procedure does not directly affect tissues in the vicinity of the monitoring site (e.g. does not directly cut, heat, ablate, abrade, the tissues, etc.) may also be advantageous for determining an effect of the surgical procedure on one or more physiologic parameters of a tissue (e.g. a vessel wall stiffness, change in nerve activity, change in local blood perfusion, etc.) adjacent to the monitoring site.

Such tone measurement may be useful in determining the local stiffness of tissues (and/or overall wall stiffness of an adjacent vessel, organ, etc.) in contact with an array of surgical tool tips (e.g. so as to determine the type of tissue adjacent to one or more tips, to locate transitions between one tissue type and another, to locate regions of excessive wall thickness, to locate a cancerous tumor, etc.). Tone measurement may further be used to characterize the type of tissue with which the tip is interfacing (e.g. muscle, nervous tissue, plaque, cancerous tissue, etc.). Such information, possibly in combination with bioimpedance data, may be used to determine how much RF energy to apply locally during an RF ablation procedure.

In aspects, relating to a method for RF ablating tissue, the local tissue tone may be measured before, during, between individual RF pulses, and/or after a train of RF pulses. As the local tissue tone changes during application of the RF pulses, the tonal changes may be used to determine the extent of the therapy. As the RF ablation process is applied to the adjacent tissues (via one or more sensing tips, an ablation electrode, etc.), the tonal measurements (as determined by one or more sensing tips, via the same tip through which the RF signal may be applied, etc.) may be monitored as the tonal measurements may not be significantly affected by the local RF currents.

Electrophysiological stimulation and/or sensing from one or more electrodes arranged along the surgical tool may be used to monitor and/or stimulate nervous and/or physiologic function within a local anatomical structure (e.g. a vessel wall, along a nerve, an organ wall, a duct, etc.). Such information may be used to hunt for target tissues (e.g. nerves), select tissues for a surgical procedure, to determine the degree of progression of a surgical procedure (e.g. a degree of ablation or neuromodulation during surgery, etc.). In aspects, directional stimulation and sensing may be used to selectively treat only nerves that are configured to send signals in the preferred direction (e.g. to selectively target primarily efferent nerve bundles, afferent nerve bundles, etc.).

In aspects, one or more of the electrodes may be configured to apply/receive an RF or microwave current to/from the surrounding tissue. The current may be provided locally between two or more electrodes, or alternatively between one or more electrodes and a macroelectrode placed elsewhere on the body (e.g. on a large skin patch over the surgical site, an electrode placed on another organ, as selected from multiple patches placed over the body, in an associated catheter electrode, etc.). In a non-limiting example where current is restricted to being applied between electrodes, the path for current flow may be well controlled, yet may be highly localized. Alternatively, in an example where current is passed between one or more electrodes and one or more remotely situated macroelectrodes, the current flow may be more challenging to control, but may be used to access tissues more remote from the surgical tool (e.g. farther into the adjacent tissues, etc.).

In aspects, network impedance measurements between one or more electrodes and one or more macroelectrodes (e.g. as attached to the body of the patient), may be monitored prior to and/or during application of an RF ablation current. Each surgical tool electrode and/or macroelectrode may include an impedance control circuit that may be adjustable such that the overall current flow through the network formed from all the elements is controlled there through. Such a configuration may be advantageous to better control the local ablation process, thus targeting the local tissues with more accuracy and confidence than less controlled approaches.

In aspects, a plurality of electrodes may be engaged with the flow of current during an ablation process. In such a non-limiting example, the local impedance of each pathway (i.e. through the surgical tool and each associated electrode) may be monitored and/or controlled so as to better optimize the current delivered thereto. Additionally, alternatively, or in combination, the local current flow through each electrode may be monitored so as to determine the path of the current flow, to ensure no leakage currents are detected, etc. Such information may be used to better control the delivery of ablation and/or stimulation currents to the local anatomy during an ablation/stimulation procedure.

Optionally, before, during and/or after the ablation or stimulation current is applied to the surrounding tissues, one or more sensors arranged on the surgical tool may monitor a physiologic parameter (e.g. water concentration, tone, blood oxygen saturation of local tissues, evoked potential, stimulation/sensing of nervous activity, EMG, temperature, analyte level, etc.) to determine the extent of completion of the intended surgical procedure.

In aspects, the tip of the surgical tool may be equipped with an optical microsensor (e.g. a micropackage including a light source and/or a complementary metal-oxide semiconductor (CMOS) photosensor). During a surgical procedure, the optical microsensor may be positioned against or near to the local tissues for analysis before, during and/or after an ablation procedure.

In aspects, an optically configured sensor (or group of tips) may be configured to locally assess blood perfusion, renin concentration, tissue colorimetric properties, and/or blood oxygenation in the tissues adjacent thereto. The system may be configured to automatically adjust and/or halt the surgical procedure based upon changes (or lack thereof) in this signal. Alternatively, additionally, or in combination, the system may alert a user (e.g. a surgeon, an attendant, etc.) to a change in this signal before, during, and/or after a surgical procedure. Such a configuration may be useful for assessing local tissue health before, during, and/or after a surgical procedure.

In aspects, one or more optically configured sensors may be configured to monitor for changes in the colorimetric properties of tissues adjacent thereto, such as during an ablation procedure. Such colorimetric property changes may be indicative of a change in tissue state caused by the procedure (e.g. local tissue damage, denervation, etc.).

In aspects, one or more optical sensors may be configured so as to be biased towards the tissues of the vessel in the vicinity of the surgical site or distally therefrom. The optical sensors may include one or more light sources (e.g. light emitting diodes, fiber optic tips, etc.) configured to delivery narrow, multiband, and/or wideband light to the adjacent tissues. The optical sensors may include one or more photodetectors (e.g. a photodetector, a phototransistor, OCT fiber bundle, a fiber optic tip, etc.) to receive and/or analyze the light reflected from the adjacent tissues. The received light may be related to that emitted by one or more of the light sources, or may be received from an ambient light source, located to the exterior of the vessel, or the exterior of the subject's body.

In aspects, one or more of the sources may be configured to emit light at predetermined wavelengths such that different absorption characteristics of the adjacent tissues, dependent on the wavelengths, may be observed during the surgical procedure. The photodetectors may be configured to receive at least a portion of this light, so as to assess the absorption characteristics with the system (e.g. via a pre-amplification system in accordance with the present disclosure, in an attached electronics unit, etc.). The photodetected signals may be used to determine an oximetry value or a signal related thereto.

In aspects, the optical sensors may be biased towards a site on the lumen wall before, during, and/or after the surgical procedure. Alternatively or in combination, the optical sensors may be held in a predetermined orientation with respect to the lumen wall (such as via being attached to a collar of known size, attached to a structure of known width, as part of a structure that is expanded to a known radius, onto the inner surface of a hook element, etc.). The bias between the sensors and the wall may be controlled by sensors and actuators both in accordance with the present disclosure. Changes in the optical signals detected by the photodetectors (due to changing bias force) before, during and/or after a surgical procedure may be related to changes in the bias force with which the sensors are held against the vessel wall. Such a configuration may be advantageous for determining a change in sympathetic tone and/or vasodilation before, during and/or after a surgical procedure.

In aspects, one or more of the optical sensors may be coupled with one or more strain and/or interfacial force measurement methods, to give a more precise reading of the bias force between the sensing tip(s) and the adjacent tissues.

In aspects, the optical sources may be selected such that the penetration of the light into the adjacent tissues may be controlled. In aspects, a blue wavelength and a red wavelength may be emitted into the tissues. The blue wavelength may provide information relating to the deformation and absorption near the to the surface of the tissues, while the red wavelength may penetrate more deeply into the adjacent tissues, providing a signal that changes in response to deformation of tissues farther from the contact site(s) between the sensor(s) and the tissue. The photodetectors or equivalent optical detection pathway may include filters, polarized windows, or the like to separately assess the different spectra during an analysis. Comparison between the photodetected signals in the blue spectrum with those obtained from the red spectrum may be used to determine tone and/or elastic modulus of the tissues of the vessel in the vicinity of the optical sensors. Such a configuration may be advantageous for assessing sympathetic tone and/or vasodilation, vessel wall stiffness, and/or local tissue stiffness before, during and/or after a surgical procedure. Changes in such properties may be indicative of the degree of completion of the surgical procedure.

In aspects, an externally placed (e.g. onto the body of the subject) energy source (e.g. infrared, near infrared, visible, microwave, radiation, etc.) may be directed into the body towards the surgical site. The energy source may optionally be modulated to provide a more easily detected signal within the subject. One or more optical sensors arranged upon the surgical tool may be configured to sense light emitted from the energy source. The mapping of received light may be used to locate anatomical features such as nerves near to one or more of the optical sensors.

One or more externally placed light sources may be used to help locate the anatomical sites of interest during the procedure. An external light source may include a narrow band light source, a broad band light source, light sources spaced apart from each other, and/or combinations thereof. The light sources may be modulated so as to be more easily detectable by sensors located in or near to the anatomy of interest. In one non-limiting example, a plurality of light sources may be aimed at the surgical site from distinct vantage points within the body (i.e. as accessed via an endoscopic procedure, etc.) or externally to the body (i.e. as positioned at locations on the body).

In aspects, an endoscopic camera may be placed near to the anatomy during a procedure to observe both the anatomy, as well as placement of the surgical tools in the vicinity of the anatomy. In one non-limiting example, the endoscopic camera and/or light source may provide a suitable macroelectrode for RF ablation processes performed during the surgical procedure.

In aspects, one or more optical sensors may be equipped with a corresponding micro-light source (e.g. an organic light-emitting diode (oLED), a light-emitting diode (LED), etc.). The micro-light source may be used to direct light into the adjacent tissues. One or more optical sensors may be configured to detect light emitted from the micro-light source as back scattered by the adjacent tissues. Such information may be used to detect anatomical features (e.g. nerves, tumors, etc.) in the adjacent tissues.

Such optical configurations may be advantageous for mapping the local tissues before, during and/or after a surgical procedure. They may also be advantageous for implementation into a nerve detection system (e.g. as input to a nerve hunting algorithm, etc.).

In aspects, the surgical tool may include one or more microcircuits interconnected with one or more of the sensors. Such a microcircuit may include signal processing circuitry, a local control circuit, multiplexors, communication hardware, power management, combinations thereof, or the like. In order to substantially reduce the number of signal wires that must be routed to the surgical site during the procedure, a networked array of electrodes arranged within the surgical tool may be multiplexed together with a locally placed control circuit (e.g. an application specific integrated circuit, distributed/interconnected circuit elements, a collection of flexible semiconducting circuit elements, etc.). The control circuit may communicate such signals with an extracorporeal system (e.g. a computer, a control system, an RF ablation controller, a data acquisition system, etc.). The control circuit may communicate with the extracorporeal system via analog and/or digital methods. In one non-limiting example, the communication may be of primarily digital means such that the control circuit may exchange data pertaining to any sensing tip in the array, as well as switch data, control data, RF pulse routing, etc.

In aspects, the networked array of electrodes may be interconnected with distributed electronic elements and flexible electrical interconnects (e.g. as applied to a clamp surface, a hook, a loop, as provided by structural wires, microfingers, wire mesh elements, etc.).

A surgical tool (e.g. a guidewire, a catheter, etc.) in accordance with the present disclosure may include one or more microfingers arranged such that each microfinger may move or interact with local anatomy substantially independently from other microfingers in the tool. Thus if an array of microfingers is placed against a rough or otherwise uncontrolled surface, each microfinger may be able to contact, and substantially maintain contact with the surface during use, even if the microfinger array is dragged along the surface during a procedure. Such independently adjustable microfingers may be advantageous so as to maintain a known interfacial pressure, especially while monitoring, stimulating and/or ablating the tissue with the microfingers.

By microfinger is meant a, potentially curved, finger like member (i.e. optionally with multi-axial curvature). Such microfingers may generally have a characteristic width (although may be of any cross sectional makeup). The microfingers may generally have characteristic widths on the order of approximately 1 mm, 0.5 mm, 0.1 mm, 0.05 mm, 0.01 mm, or the like. In aspects, one or more microfingers may include a nitinol structure (e.g. a wire, a ribbon, etc.) with characteristic width of approximately 50 µm.

In aspects, one or more of the microfingers may be selectively coated with an isolation layer (e.g. an oxide layer, a dielectric coating, a polymer layer, a lubricious layer, etc.). Such isolation may be selectively applied to regions of the microfingers (i.e. so as to create isolated regions and sensitive regions thereof).

The microfingers may be configured so as to bias against the adjacent tissues during a procedure and may be used to sweep the local anatomy, both sensing and ablating during a surgical procedure. The microfinger dimensions and structure may be designed so as to provide substantially uniform and predictable bias forces on the adjacent tissues over a wide range of movements and dimensional variation.

In aspects, one or more microfingers may include a spring-like wire element (e.g. nitinol, spring steel, etc.) or may include composite structures including a spring-like element to provide a bias force so as to push the tip of the microfinger towards the wall of a vessel, an organ, and/or a tissue site of interest.

In aspects, a microfinger may include a nitinol structure, optionally configured for passage of current flow, to and from the surrounding tissues. The nitinol structure may be configured such that, when an RF pulse is applied there through towards the surrounding tissues, the nitinol structure may retreat from the tissues after a predetermined amount of energy has passed there through. Thus the nitinol structure may provide an inherently controlled method for applying a bolus of RF energy to the surrounding tissues. Such a configuration may be adapted for use simultaneously, additionally, alternatively and/or in combination with the other aspects described in this disclosure.

In aspects, one or more of the microfingers may be formed slightly off axis, such that relative axial movement of an overlying sheath may be used to retract the microfingers into the sheath or deploy the microfingers outwards so as to interface with the anatomical site.

Such a configuration may be advantageous for simultaneously mapping and selectively ablating an anatomical site during a surgical procedure.

In aspects, one or more microfingers may be provided with highly miniaturized and flexible structure so as to more easily access hidden and/or difficult to access anatomical sites within the body.

In aspects, one or more of the microfingers may include a sensor in accordance with the present disclosure for capturing information from an adjacent anatomical site.

In aspects, a system in accordance with the present disclosure may include a coolant delivery system (e.g. a saline delivery system) in order to cool the microfingers and/or surrounding tissues during and/or after an ablation procedure. Such coolant delivery may be advantageous for minimizing char and excessive damage associated with an ablation procedure. In aspects, such a coolant may be provided to maintain one or more of the microfingers in a first state (i.e. a delivery state). When the coolant flow is stopped, the associated microfingers may transition to a second state (i.e. a deployed state). Such a configuration may be advantageous for delivering a guidewire tip in accordance with the present disclosure deep into a target lumen before deploying one or more zones of the guidewire so as to interface with the walls of the lumen as part of a procedure.

In aspects, one or more of the microfingers may include an exposed electrode area arranged so as to primarily interface with the walls of the adjacent anatomy upon deployment. Such a configuration may be advantageous for minimizing current flow into the adjacent tissues and to better control RF current flow in the vicinity of the electrodes, etc.

The microfingers may include one or more active material elements. Control signals delivered to the active material element may help to bias the microfingers towards the intended surgical site, actively control the contact forces between finger tips and the surgical sites, etc. Some non-limiting examples of active materials that may be suitable for application to one or more microfingers include shape memory materials (e.g. shape memory alloys, polymers, combination thereof), electroactive polymers (e.g. conjugated polymers, dielectric elastomers, piezoelectric polymers, electrets, liquid crystals, graft elastomers, etc.), piezoceramics (e.g. amorphous piezoceramics, single crystals, composites, etc.). In addition the active material may be used as a vibratory exciter and/or mechanical probe, for use in monitoring the tone of the adjacent tissues (see above), alternatively, in addition or in combination, to cause vibratory/ultrasonic ablation and/or local heating to the tissues. In aspects, such active material elements may be configured for simplified deployment of one or more aspects of an associated guidewire towards the walls of a lumen into which it is inserted during a procedure.

In aspects, one or more electrodes may include a conjugated polymer to interface with the adjacent tissues. Some non-limiting examples of suitable conjugated polymers include polyaniline, polypyrrole, polyacetylene, poly(3,4-ethylenedioxythiophene), and the like.

In aspects, one or more of the microfingers may include an electrical shield such that the associated microfinger tips are effectively shielded from other currents flowing through an associated surgical tool (such as a catheter), the body, etc. during a procedure.

In aspects, a surgical tool may include or interface with a bi-directional switching network, microcircuit amplifier array, etc. in order to amplify sensed signals as close as possible to the anatomical interface, as well as to switch the function of a microfinger tip between sensory, stimulatory, and/or ablation functions, etc.

A bidirectional switching network may be used to enable multi-functional stimulation/sense capabilities in one or more microfingers, tool tips, etc. The switching network may be included in a local amplifier array, included in a flexible circuit on one or more microfingers, attached along the surgical tool, as part of the electrical routing along a finger, etc. or alternatively as an extracorporeal element included in a surgical system in accordance with the present disclosure.

A micro amplifier array may be used to preamplify the signals obtained from one or more sensory aspects of the microfingers, so as to improve the noise signature, etc. during use.

In aspects, one or more of the microfingers may be provided such that they are sufficiently flexible so as to buckle, or change orientation during back travel (e.g. configured and dimensioned so as to prolapse), so as to prevent puncture of the local anatomy. A configuration as outlined in this example may be advantageous for providing contact with the local anatomy without significant risk of damaging the adjacent anatomy (e.g. puncturing a vessel wall, etc.) which may be a concern with stiffer, more traditional structures.

In aspects, one or more of the microfingers may be sufficiently hyper elastic (e.g. formed from a memory alloy material, a superelastic material, etc.) so as to effectively deploy from a very small deployment tube and expand outward to larger tissue areas over which to monitor. Such a configuration may be advantageous in so far as a small number of unit sizes may be suitable for treating a wide range of anatomical structures. In addition, the designed curvature and form of a microfinger may be substantially chosen so as to further enable a wide deployable range of movement.

In aspects, a surgical tool including a plurality of microfingers in accordance with the present disclosure may be employed so as to determine physiologic response more remotely from an intended surgical site than may be available within a single array. Any of the above concepts may be employed along the same lines by extending interactions between microfingers within an array, to inter-array interactions.

A system in accordance with the present disclosure may be used to monitor physiologic activity associated with a surgical site prior to, during and/or after a surgical procedure is applied thereto. In aspects, a system in accordance with the present disclosure may be configured to provide a surgical procedure, optionally in conjunction with the monitoring. Some suitable examples of surgical procedures include RF ablation, Argon plasma coagulation, laser ablation, water jet ablation, ultrasonic ablation, cryoablation, microwave ablation, abrasion, biopsy, delivery of a substance (e.g. a chemical, a drug substance, an acid, a base, a chemotherapy drug, etc.), etc. The local physiologic activity (e.g. nervous activity, blood perfusion, tonal changes, muscular sympathetic nerve activity, local field potentials, etc.) may be monitored with one more sensors and/or associated stimulators. Additionally, alternatively, or in combination, a technique for assessing the properties of an associated surgical site may be employed. Such techniques may include assessing values and/or trends in bioimpedance, blood pressure, tissue oxygenation, tissue carbon dioxide levels, local temperatures and changes thereof, etc.

In aspects, the system may be configured to deliver a substance such as a therapeutic agent (e.g. a neuroblocking agent, ethyl alcohol, botulinum toxin, etc.) to the anatomical site of interest or a treatment site.

In aspects, a system in accordance with the present disclosure may include a substrate onto which one or more sensors may be coupled. Such a substrate may be formed from a clamp face, a hook interface, a mesh, an interwoven ribbon array, a cloth, rolled film, etc. The substrate may include stretchable and/or flexible electronic materials.

In aspects, one or more electrical interconnects may be formed from carbon nanotubes (e.g. single-walled nanotubes (SWNTs), multi-walled nanotubes (MWNTs), etc.), nanowires, carbon fibers, metalized carbon fibers, metallic wires, composites, conductive inks, combinations thereof, or the like.

A portion, or all of the substrate and/or an associated substrate carrier film may be formed from polyurethane, a silicone, a general elastomer, silk fibroin materials, or the like and/or combinations thereof. Inclusion of microporous or fibrous substrates, may be advantageous to allow the substrate or substrate carrier film to adhere to the adjacent tissues via capillary effects (i.e. tendencies to wick fluid from adjacent tissues into the substrate). The thickness of films formed from the material may be less than 30 µm thick, less than 20 µm, less than 10 µm, less than 4 µm, less than 1 µm. Composites of somewhat stiffer materials (such as polyimide, polyethylene terephthalate (PET), polyethylene naphthalate (PEN), etc.) and somewhat softer materials (e.g. silicones, polyurethanes, thermoplastic elastomers, etc.) may be used to compromise between overall structural stiffness and conformal capabilities.

Patterned overcoats and/or composite layers may also be used to expose electrode materials and/or sensing tips to the surrounding tissues in the vicinity of measurement regions, etc.

In aspects, one or more regions of the substrate may be formed from a silk material (e.g. *Bombyx mori* cocoons). The material may be processed to remove sericin (which may cause undesirable immunological response) using methods known in the art. The resulting material can be solvent cast into shapes and crystallized to form self-supporting structures.

In aspects, adaptive temperature estimation may be used to better control the RF process. Modeling of changes in local bioimpedance may be related to local temperature changes during the ablation process. Such measurements as well as local thermoconductive properties, tissue thermoconduction, etc. may also influence the rates at which a local ablation process may take place (i.e. as related to a thermal ablation process).

The system may also include one or more sensors for monitoring nervous activity and/or related physiologic activity during the RF ablation process. Some examples of suitable monitoring techniques include evoked potentials, local field potentials (LFP), electromyography (EMG), muscule sympathetic nerve activity (MSNA), mechanomyography (MMG), phonomyography (PMG), and combinations thereof. Mechanomyography (MMG) measures the force created by local muscle contractions caused by associated neural activity. Phonomyography (PMG) measures low frequency sounds associated with movement generated by associated neural activity. Traditionally, techniques such as MMG and PMG have been employed on externally accessible nervous and muscular tissues. One advantage of such techniques as provided herein may be that they may not be as easily affected by local electrical noise as EMG and the effects of the nervous activity may be generally sensed farther from the associated nerve than with electromyographic techniques.

Alternatively, additionally or in combination the ascribed sensing techniques may be combined with stimulation from local sources. Such stimulation and sensing may be advantageous in determining functionality of local nerves without the need to listen to complex biologically generated nervous activity. Furthermore, combined stimulation and sensing may be advantageous for determining functionality of a local nerve in real-time during a denervation and/or ablation procedure (e.g. the successive stimulation and sensing may be used to determine the degree of neurological block and/or neuromuscular block there between). Such functionality as well as directionality of the nerve signal propagation (e.g. efferent, afferent, etc.) may be more easily determined through use of combined local stimulation and sensing.

Several patterns of nerve stimulation may be used to determine the function of the local nerve structures as well as any associated degree of neurological block and/or neuromuscular block that may be caused by the surgical procedure (e.g. ablation), anesthesia, abrasion, etc.

In aspects, a single stimulation pulse may be used to elicit maximal response from the associated nerve at frequencies of less than 10 Hz, less than 1 Hz, less than 0.1 Hz. The downstream response as measured by any of the described techniques will depend on the frequency with which the stimuli are applied. In order to allow for complete recovery of the nerve between stimulations, a frequency of less than or equal to 0.1 Hz may be advantageous.

During RF ablation of an associated nervous structure, the evoked electrical and/or muscular responses may be dramatically affected. Such changes in the response may be useful in determining the state of the denervation procedure. Thus they may be advantageous to determine the exact degree of RF energy that must be applied to a given structure in order to cause sufficient denervation as desired by a surgical procedure. Such an approach may be advantageous to limit damage to surrounding tissues caused by the denervation procedure, to ensure suitable denervation has been achieved, to determine which nerves are affected by the procedure, etc.

Another technique for stimulation and sensing of the nervous response includes applying a rapid succession of pulses followed by a period of inactivity. Pulse trains may be used to gradually force a nerve into a blocked state. The rate at which a nerve enters a blocked state and later recovers therefrom may be a suitable indicator of the overall health and functionality of the nerve (i.e. as a suitable metric for determining how a procedure has affected that nerve).

Note that the sensing of the nervous response may not need to be local to a surgical site, but rather downstream (in the sense of the flow of an associated nervous signal) from the site. In aspects, a guidewire in accordance with the present disclosure may be configured to sense neurological activity caused by a stimulation event substantially upstream therefrom (i.e. the guidewire may be placed within the boundaries of the end organ).

Various mapping techniques may be applied to the surgical site, before, optionally during and after a surgical procedure. Some mapping techniques as used in cardiac interventions include pace mapping, activation mapping, entrainment mapping, and substrate mapping. It may be feasible to adapt at least some aspects of these techniques for use in the intended application. In general, these techniques may complement each other in localizing where amongst a surgical site to target the ablation procedure.

Additionally, or in combination to the aspects described herein, the surgical system may be configured to monitor one or more physiologic parameters at one or more locations in the body remote from the surgical site. Some non-limiting examples of what may be monitored include water concentration, tone, blood oxygen saturation of local tissues, evoked potential, local field potentials (LFP), stimulation/ sensing of nervous activity, electromyography, temperature, blood pressure, vasodilation, vessel wall stiffness, muscle sympathetic nerve activity (MSNA), central sympathetic drive (e.g. bursts per minute, bursts per heartbeat, etc.), tissue tone, blood flow (e.g. through an artery, through a renal artery), a blood flow differential signal (e.g. a significantly abnormal and or sudden change in blood flow within a structure of the body, a vessel, an organ, etc.), blood perfusion (e.g. to an organ, an eye, etc.), pupil dilation, electrolyte levels in a biofluid (e.g. an exudate, blood, urine, pancreatic fluid, bile salt, etc.), a blood analyte level (e.g. a hormone concentration, norepinephrine, catecholamine, renin, angiotensin II, an ion concentration, hemoglobin A1C, a water level, blood sugar levels, an oxygen level, etc.), nerve traffic (e.g. post ganglionic nerve traffic in the peroneal nerve, celiac ganglion, superior mesenteric ganglion, aorticorenal ganglion, renal ganglion, and/or related nervous system structures), combination thereof, and the like.

A surgical system in accordance with the present disclosure may include one or more elements to monitor physiologic activity and/or analyte levels (e.g. a hormone level), in and/or near to one or more portions of a gland, an endocrine gland (e.g. an adrenal gland, an adrenal medulla, etc.), etc.

In aspects, a multi tool surgical system may be employed, each tool in accordance with the present disclosure. In aspects, one or more first tools may be used to probe and/or ablate tissues at a first surgical site (e.g. an artery, a renal artery, a left renal artery, etc.), while one or more second tools may be configured to monitor one or more physiologic parameters elsewhere in the body (e.g. in an alternative artery, a vein, in an organ, at a lymph node, at a ganglion, etc.), to determine the effect of the surgical procedure there upon, etc. In aspects, the tools may be inserted into the same or closely positioned entry points into the body (e.g. a surgical port, an introducer, etc.). Such a configuration may be advantageous for providing a minimally invasive surgical tool to perform the surgical procedure (e.g. a sympathectomy, a renal sympathectomy, a parasympathectomy, a neuromodulation, etc.) with monitoring performed at multiple, remote locations within the body.

Some further aspects relating to systems and methods for adjusting (temporarily and/or permanently) nerve function, while substantially minimizing collateral damage to adjacent structures via endoscopic tools and methods are now discussed. References made to ablation may be considered to refer to a general surgical procedure (to cut, heat, cool, excise, etc.) on a tissue.

In aspects, a tool in accordance with the present disclosure may include an array of electrodes and/or sensors. The array of electrodes and/or sensors may be arranged as to interface with one or more anatomical sites within the body (e.g. along the walls of a lumen, walls of a renal artery, within an organ, a prostate, a pancreas, a liver, a kidney, etc.). The array of electrodes may be used to interface circumferentially and/or axially with the local tissues, so as to select ablation sites, validate ablation success, sense local neural activity, stimulate and sense, etc.

In aspects, one or more electrodes in the array may be used to stimulate, sense, and/or ablate local tissues and/or monitor nervous activity before, during and/or after a related surgical procedure or ablation process.

The tool may include a switch array in accordance with the present disclosure, optionally with one or more amplifiers such that one or more electrodes could be configured for stimulation, ablation, and/or sensing as part of a procedure. The tool may include electronics to monitor bioimpedance between one or more electrodes (e.g. so as to determine when the tool is adequately biased towards the intended anatomical structure, etc.).

The tool may include electronics for automatically terminating an ablation signal when a change in the sensed nervous activity is detected. In aspects, a pulsatile stimulation may be applied to one side of the ablation zone, during the ablation process and/or between ablation pulses (and/or intermixed with the ablation pulses). Another electrode may be placed to the opposing side of the ablation zone so as to monitor nervous response before, during and/or after the ablation procedure, during the pulsatile stimulation, or the like.

In aspects, individual electrodes in the array may be preconfigured so as to provide a particular signal conditioning function: sense, stimulate and/or ablate.

One or more electrodes in the array may be a monopolar electrode or part of a bipolar pair. In aspects, two or more electrodes may be arranged into pairs, multi-polar interconnects, etc.

In aspects, a tool in accordance with the present disclosure may include one or more shielding elements placed in proximity to one or more electrodes in the array or to an interconnecting lead (e.g. a lead wire, an interconnection site, a switch, etc.). In the case of electrodes, the readings from these electrodes may be used to balance and/or cancel out macroscopic or environmental action potentials and/or noise from the local micro-electrode readings taking place at the clamp-tissue interface. This approach may be used to lower the effective noise floor and improve the sensitivity of one or more of the micro-electrodes.

In aspects, one or more of the electrodes may be configured so as to protrude from the surgical tool (e.g. via emboss, plating, filament, matted morphology, etc.). Any of the microelectrodes may be embossed so as to better bias the interfacing aspects towards the tissue during a procedure. This may be advantageous to ensure that each electrode applies adequate pressure to the adjacent tissues and/or to improve the chances of tissue contact with a plurality of the electrodes In aspects, a method for treating a surgical site with a surgical tool in accordance with the present disclosure includes locating the surgical site of interest; deploying the surgical tool near to the surgical site or at a physiologically linked site within the body; monitoring electro activity (e.g. neurological activity, MSNA, local field potentials, etc.) using one or more of the electrodes included in the surgical tool to determine a reference biosignal; applying a neuromodulation and/or denervation signal (e.g. ablation, abrasion, current, light, etc.) to the surgical site for a predetermined timeframe; monitoring electrophysiological activity using one or more electrodes to determine an updated biosignal; and comparing at least a portion of the reference biosignal or a metric derived therefrom with the reference biosignal or a metric derived therefrom in order to determine the extent of the denervation.

In aspects, the method may include monitoring with different electrodes for determining the reference and the updated signals, determining a bioimpedance between electrodes during and/or after the neuromodulation procedure, or the like.

In aspects, the method may include the application of multiple pulses, monitoring other physiologic signals, algorithmically combining such signals to generate the updated signal, extracting a metric from the neural activity and/or additional physiologic signals, confirming a change in the electrophysiological activity, combinations thereof, or the like.

According to aspects there is provided, a method for determining the activity levels of, directionality, location of and/or the extent of nerve traffic and/or receptor functionality before, during and/or after a surgical procedure may include stimulating a range of nerves located at a proximal and/or distal location on or within an organ (e.g. a kidney, a renal artery, a gland, an adrenal gland, a ganglion, etc.) in a body; monitoring an evoked response at a location distal and/or proximal to the location of the stimulation; evaluating the signal quality, spectral content, etc. related to the evoked response and/or changes in the evoked response during and/or after the surgical procedure.

In aspects, the method may include applying a stimulus to the body (e.g. an injection of a neuro-blocker, a neuro-stimulant, tilting the body, a shock, inducing a vascular spasm, etc.) and monitoring functionality, directionality, location of and/or the extent of nerve traffic and/or receptor activity before, during and/or after the stimulus near one or more nerves and/or at a site located on or within an organ (e.g. a kidney, a gland, a ganglion, etc.), or a lumen (e.g. a renal artery, a renal vein, a ureter wall, etc.) in the body.

In aspects, one or more of the methods in accordance with the present disclosure may include electrically stimulating tissues at a stimulation location (e.g. one or more nerves, one or more receptors, etc.) with one or more electrical pulses, thus forming a pulse train. A pulse train may include a plurality of pulses with a predetermined spectral content (e.g. pulses centered around 10 Hz, 50 Hz, 100 Hz, 500 Hz, etc.) at one or more locations proximal and/or distal to the surgical site.

In aspects, the pulse train may be applied locally to a neurological structure, with an amplitude of generally 1.5× the voltage required to obtain a maximal amplitude compound action potential (CAP), with pulse duration of generally between 0.05 and 0.5 ms and interval of between 2 ms (for 500 Hz spacing) to 10 s (for 100 mHz spacing). The overall pulse train may include one or more pulse types, evenly spaced with alternative timing over the application of the pulse train (so as to scan through a frequency range of interest). The corresponding nervous response may be monitored at another location on the vessel or in the body. Such response may be monitored with a gain of generally 500 to 5 k and generally over a frequency band of 0.01 Hz to 10 kHz. This configuration may be used to evaluate the overall health and/or capability of the nervous structure connecting the stimulating location and the monitoring location.

In aspects, the local field potential may be monitored with pass band content preserved at relatively low frequencies in order to determine the near direct current (DC) changes in field potentials caused by the stimulus and/or surgical procedure. Such information may be reflective of changes in local analyte concentrations (i.e. as will affect the local Nernst potential formed by electrodes within the monitoring site), structural changes in the local anatomy (e.g. local tone, water content, low frequency movement, etc.), or the like. Such information may be a suitable surrogate for changes in sympathetic activity and/or neurological connection between the monitoring site and remote yet otherwise connected regions within the body.

During a surgical procedure, early indication of functional alteration to the nerve structure may be determined by monitoring for a change in the properties of the sensed signal (e.g. a change in latency, amplitude, conduction velocity, spectral content, etc.). In one non-limiting example, an ablation pulse may be applied to the nerve between the stimulatory and monitoring locations. A change in the properties of the sensed signal (e.g. a decrease in high frequency content therefrom, a change in latency, change in amplitude, etc.) may be an early indicator that the ablation pulse is being applied properly to the nervous structure situated there between. In addition, more pulses can be applied and the response monitored in order to observe the nerve response through to a sufficient state of functional alteration, such as desired as part of the neuromodulation procedure.

Monitoring may continue during a follow up period immediately after the surgical procedure, and/or during a longer term period (e.g. hours, days, weeks, etc.). Such follow up may be used to determine the success of and/or prognosticate on the longevity of the surgical intervention. Such measurements may be advantageous in determining if a surgical procedure was properly applied in a seemingly non-responding patient.

In aspects, the technique may be used to identify the particular neurons of interest to ensure that the correct neurons are being treated surgically (as well as to ensure that the extent of the treatment is acceptable). Such identification may involve monitoring a level of neurological activity on the sensed nerve(s) to determine if the levels are outside of a normal range (e.g. as compared with other sites in the body, an activity metric for the patient population or a subset thereof, previously recorded measurements, etc.).

A method for generating a follow up schedule following a surgical procedure may involve monitoring the neurological activity of the site within the body for a period of time (e.g. hours, days, weeks, etc.) after the surgical procedure; trending the neurological activity to create a metric relating to changes therein over the period of time; and predicting recurrence data (e.g. probability of recurrence, a timeframe of recurrence, etc.) therefrom; and generating a follow up schedule dependent upon the recurrence data.

In aspects, a surgical tool and/or guidewire in accordance with the present disclosure may include a hook-like tip (with one or more sensors or electrodes arranged thereupon) to make consistent and controlled contact with the anatomy (so as to maintain a reliable contact with the intended monitoring site over a period of time). A soft hook-like structure with tissue interfaces (electrode arrays, sensor arrays, etc.) fashioned towards the inner and/or outer surface of the hook may be used to delicately contact the key anatomy during a surgical procedure (e.g. such as contact a region within the renal cortex of a kidney during a procedure, to interface with a wall of a vessel, to interface with an adipose tissue, etc.). The hook may include a quick release (e.g. a mechanical quick release, an electroactive material quick release, etc.) for simple removal from and/or positional correction in the vicinity of the monitoring site (e.g. around the cortex, within a vessel wall, within a tissue volume, etc.) during and/or at the conclusion of a surgical procedure.

In aspects, soft interfacing structures and/or hook-like structures may be used to controllably interface with the tissues, applying contact pressures that are just suitable for sensing, stimulating, and/or ablation procedures while minimizing the changes of unnecessary pressure induced neural blockage during an associated procedure.

In aspects, a method for searching for a nerve of interest on the wall of a vascular vessel may include applying a point pressure on the wall of the vessel while monitoring distal and/or proximal nervous activity (e.g. monitoring, and/or stimulation and sensing on either side of the point pressure probe). Changes in the observed signals may be indicative of pressure induced neural block due to the applied point pressure (i.e. thus identifying the location of the neural anatomy in question).

Relating to nerve compression syndrome, acute nerve compression studies have shown some loss of nerve function through application of acute transverse pressure above 40 mmHg, and loss of all nerve function at pressure application above 50 mmHg. Other studies have shown functional block under transverse compression when a pressure of 30 mmHg less than diastolic pressure is applied and 45 mmHg less than the mean arterial blood pressure is applied to the nerve. Thus one or more components of the system (e.g. a clamp, an electrode element, a point pressure applicator, etc.) may provide pressure variation above and/or below these ranges in order to assess nerve function, location, etc. as described herein.

In aspects, a point pressure applicator in accordance with the present disclosure may be configured to operatively provide an oscillating pressure to the test site, to synchronize pulsatile pressure application with an array of probes, etc. so as to better orient a pair or array of probes for an ablation procedure.

In aspects, the holding force of one or more surgical elements (e.g. a clamp, a hook, a loop, a point pressure applicator, etc.) may be controlled by various means including bioimpedance measurements, interfacial pressure sensors, micro-pulse oximetry based through flow and/or local perfusion measurements via optically equipped sensing tips, and the like. It may be desirable to control the application of force for various reasons such as causing signal inhibition via mechanical compression (nerve compression); for imposing a temporary nerve block during an associated procedure; to mask the underlying nervous activity during surgical site selection; to control one or more contact pressures and/or impedance for performing an associated ablation and/or monitoring procedure.

In aspects, the surgical tool may include a means for applying a vacuum at sites in and around the electrodes. Such vacuum attachment may allow for very intimate yet gentle contact between the adjacent tissue surface and the electrodes during a procedure.

In aspects, a soft flexible structure may be used in conjunction with a surface enhancement and/or wicking function (a hydrophilic material, a porous material, etc.) so as to draw fluid out from the vessel surface and use the resulting capillary forces and surface tension to form a tight, intimate contact between the tool and the tissue suitable for neurovascular monitoring. This may be an option for long term placement (e.g. placing of an implantable component during a procedure for follow up, etc.). Silk structures included into the flexible structure may be suitable for providing this functionality, optionally with a first layer that can dissolve quickly and a second layer that may dissolve over the course of hours, days, weeks, etc.

In aspects, the flexible structure may include a medicament (e.g. a neural blocking agent, an anesthetic, lidocaine, epinephrine, a steroid, a corticosteroid, an opioid, alcohol, phenol, etc.).

In aspects, the structure may include a thin degradable support structure. In aspects, the support structure may quickly dissolve in the presence of liquid (saline) such that it may be placed beside the vessel and wetted, so as to cause the remaining structure to change shape and bias against the vessel walls.

Such soft configurations may be useful to establish a reliable, yet gentle contact to a vessel surface or within an organ element, intimately contouring to the surface of the vessel or local anatomy without applying excessive pressure thereto. Intimate yet soft contact may be advantageous for reading sensitive neurological signals without interfering mechanically with signal transmission thereof. Such soft contact may also be advantageous in reducing the relative movement between elements of the tool and the anatomy of interest.

A surgical tool in accordance with the present disclosure may include one or more whiskers extending from a tool surface so as to reliably contact an adjacent tissue structure during a surgical procedure. The whiskers may include electrodes, and the like.

Whisker penetration into an adjacent nerve bundle may be used to achieve more intimate contact thereto, as well as to better isolate electrodes from other macroscopic signal interference, etc.

Whiskers may be formed from microfibers, nanofibers, microneedles, nanoneedles, etc. In one aspect, one or more whiskers may be formed from a carbon structure, e.g. a carbon fiber, a carbon nanotube, etc. The whiskers may be insulated along a portion of their length, with an electrically exposed region at the tip there upon.

In aspects, a boundary method for monitoring a surgical site during a surgical procedure may be employed. During this approach a plurality of sensor tips may be arranged in contact around a perimeter of a surgical region on a tissue surface, whereby the electrophysiological signals measured at locations along the surface may be used to determine the state of the tissues within the boundary. For purposes of discussion, the boundary may be effectively the distal and proximal ends of the vessel or the extents of the surgical area, when applied to a tubular organ of interest.

In aspects, a visual detection approach may be used in combination or coordination with one or more surgical approaches in accordance with the present disclosure. Visual assessment may be used to at least partially guide the surgical procedure. The feedback may be in the form of a visible, a near infrared, infrared spectroscopic, or similar camera system, used in conjunction with the surgical tools, so as to better visualize the vessel/organ structure, identification of target anatomy (e.g. a nerve, nerve bundle, etc.) on the target organ (e.g. an artery, kidney, an adrenal gland, etc.), placement of tools onto the target anatomy, etc.

In aspects, a backlit vessel lighting system may be used to assist with visualizing the anatomy, locating target anatomy, etc.

In aspects, the system may include a feature enhancing medium, to highlight targeted tissue species (e.g. highlight nerve tissues, etc.). The medium may include molecular binding species to selectively bind with surface receptors on the intended target tissue, changing one or more visual (chromatic) properties in the process and/or including a visual marking moiety. Some non-limiting examples of suitable molecular binding species are peptides and aptamers. Suitable peptides and aptamers may be selected for target tissue (e.g. nerve tissue, fat, etc.) and may be selected as known in the art.

Inclusion of molecular binding species that have been selected for the target cells may be advantageous to assist with anatomical visualization during a surgical procedure. The molecular binding species may be provided suspended in a delivery vehicle, such that it may be conveniently delivered to the target tissues during a procedure. The delivery vehicle may be a gel material, a 1 part curing gel, elastomer, etc. that may be conveniently delivered to the target tissues. A fully curable vehicle may be advantageous for providing a simplified method for completely removing the medium from the body after the surgical procedure and/or targeting process has been completed.

Molecular binding species may include a visual marking moiety that is configured to improve visibility thereof. Thus the molecular binding species will bind to the target tissue sites (e.g. nerve tissue, etc.), and will be highlighted by the visual marking moiety for visualization with an appropriate visualization system. Some non-limiting examples of visual marking moieties include: 5-carboxyfluorescein; fluorescein-5-isothiocyanate; 6-carboxyfluorescein; tetramethyl-rhodamine-6-isothiocyanate; 5-carboxytetramethylrhodamine; 5-carboxy rhodol derivatives; tetramethyl and tetraethyl rhodamine; diphenyldimethyl and diphenyldiethyl rhodamine; dinaphthyl rhodamine; rhodamine 101 sulfonyl chloride; Cy3, Cy3B, Cy3.5, Cy5, Cy5.5, Cy 7, indocyanine green, IR800CW or combinations thereof.

This visualization approach may be advantageous to identify the key tissues for surgical procedures (e.g. neuromodulation procedures, sympathectomy, renal sympathectomy, etc.). By providing the material in a form suitable for surgical delivery and complete removal post operatively, the resulting system may be safer compared to approaches that require systemic application of the material.

A surgical system in accordance with the present disclosure may include additional functionality including: angiographic die delivery, saline delivery, temperature monitoring, intra and extra vascular coordination between devices, through wall imaging, through wall current flow, saline provision for internal arterial cooling, and the like.

FIGS. 1*a-d* show aspects of a sensing guidewire 100 in accordance with the present disclosure. The guidewire 100 is shown placed within an organ 1 (such as a kidney) of a body. The guidewire 100 includes a sensing tip 110 which is positioned within a region 3 (i.e. in this case the renal cortex 3) of the organ 1. A volume 111 defined in the vicinity of the sensing tip 110 may be coupled with the sensing tip 110 during a procedure (e.g. for purposes of monitoring, stimulating, treating, ablating, delivering a substance to, etc. tissues in the vicinity of the volume 111). The guidewire 100 has been inserted endovascularly, percutaneously, etc. into a lumen in the body (e.g. a femoral artery, a femoral vein, a radial artery or vein, etc.) and directed to the monitoring site within the organ 1 shown. In the example shown, the guidewire 100 has been directed along the renal artery 5 (alternatively along a renal vein 7 or a ureter 9, via an aorta 11, a radial access site, a femoral access site, or the like, etc.) such that the tip 110 of the guidewire 100 is placed in intimate contact with one or more electroactive anatomical sites there within. In aspects, the guidewire 100 may be placed such that the tip 110 is oriented within the lumen of a vessel (e.g. an artery, a vein, a ureter, a renal artery, etc.) for obtaining physiologic information therefrom.

An alternative access point 125 is shown along the ureter 9, which would provide access to the pelvic wall. In such a situation, the guidewire 100 may be delivered such that one or more sensors located in the tip 110 thereof may interface with the pelvic wall, thus monitoring one or more activities associated with the sensory receptors (i.e. renal mechanosensory nerves) located therein.

In aspects, a guidewire 100 placed within the renal pelvis may be arranged so as to monitor electrophysiological activity during an associated stimulus event, surgical procedure/event, follow up procedure, stress test, etc. Such events may include a change in renal pelvic pressure (e.g. as induced by a change in posture, introduction of bolus of fluid, altering blood pressure systemically, etc.), introduction of a vasodilator (e.g. bradykinin, etc.), locally to the renal pelvis, inducing a thermal change (e.g. changing a room temperature, introducing a hand into cold or warm water, cooling or warming the blood, etc.), performance of a surgical procedure in accordance with the present disclosure, combinations thereof, or the like. The local electrophysiological response to such stimulus may be an indicator of the health of the kidney, may help to quantify the state of the sympathetic nervous system in the subject, may be used to determine or predict the extent that a subject may respond to a procedure, etc. In aspects, the stimulus may cause a change in afferent signal activity from nerves innervating the renal pelvis, renal cortex, adrenal gland, etc. Such activity may be monitored at a second location near a neural plexus along the renal artery or elsewhere in the body. The presence, change in, or absence of such signals at the second location may be indicative of the health of the neurological interconnection there between (e.g. the state of the nerves located between the two sites, the extent of a neuromodulation procedure, etc.).

The guidewire 100 may be connected to a controller 120 (not explicitly shown) for purposes of capturing signals from the tip 110 thereof. The guidewire tip 110 may include one or more sensors and/or electrodes, each in accordance with the present disclosure. The guidewire 100 may include one or more electrical interconnects (not explicitly shown) at the proximal end for interfacing with the controller 120.

Such a configuration may be advantageous for monitoring key physiologic information relating to a neuromodulation stimulus, a stress test, a surgical outcome, disease state, a surgical follow up, a neuroendocrine diagnostic, a neurological response to one or more of the above, etc. In aspects, such information may be used for purposes of diagnosing a disease within a subject, for determining the outcome of a stimulus or surgical procedure, for predicting the outlook of a subject after a surgery or a procedure, for predicting a subject's response to or suitability for a neuromodulation therapy, etc.

FIG. 1b shows a schematic of a sensing guidewire 100 in accordance with the present disclosure. The guidewire 100 includes a sensing tip 110 at the distal end thereof. The sensing tip 110 may include one or more sensors and/or electrodes each in accordance with the present disclosure. The guidewire 110 may also include one or more connectors 140 located at the proximal end thereof. The connectors 140 may be dimensioned and configured to interface with an interconnection module 135 or a controller 120. Although shown separately, the interconnection module 135 and the controller 120 may be integrated into a single unit. In aspects, a system in accordance with the present disclosure may include both an interconnection module 135 and a controller 120 coupled together by a cable 145.

The guidewire 100 may include one or more leadwires and/or fibers to connect elements in the sensory tip 110 to the connectors 140 thereof. In aspects, such leadwires may be constructed from one or more materials known in the art. In aspects, the leadwires and/or fibers may be constructed from MRI compatible materials (e.g. resistive wires, carbon fibers, etc.) so as to minimize heating during use in MRI guided surgical procedures.

In aspects, the optional interconnection module 135 may include one or more preamplifiers, multiplexers, switching networks, etc. each in accordance with the present disclosure. Such a configuration may be advantageous to minimize the length of leadwires between the sensing tip 110 and the first signal amplification stage (i.e. a preamplifier in the interconnection module 135).

In aspects, the guidewire 100 may include one or more microcircuits 130 embedded therein. The microcircuits 130 may be coupled with one or more elements within the sensing tip 110 as well as coupled to the connectors 140. The microcircuits 130 may be dimensioned and configured to provide suitable preamplifier functionality, multiplexing operations, digital communication hardware, etc. in order to improve signal integrity from one or more elements within the sensing tip 110, to reduce lead wire count, etc. In aspects, the microcircuits 130 may be coupled to elements of the sensing tip 110 using an ultra-high density interconnect technology as known in the art and in accordance with the present disclosure.

In aspects, the microcircuit 130 may be implemented in an application specific integrated circuit, as one or more bare die chipsets, flip chips, ultrafine pitch ball grid array mounted chipsets, chip scale packages, ultra-fine blind via attachment, flexible HDI interconnects, wire bonded bare die, combinations thereof, or the like. In aspects, the microcircuit 130 may be formed from a thinned silicon die, thinned to a thickness of less than 100 µm, less than 50 µm, less than 10 µm, less than 5 µm. In aspects, the microcircuit 130 may be provided in an ultralow profile flip-chip, chip scale package, with pitch scaling in the range of 10-50 µm.

In aspects, an array of microcircuits 130 may be arranged upon a substrate in accordance with the present disclosure to facilitate interconnection with the sensing tip 110. The array of microcircuits 130 may be arranged along the substrate and dimensioned so as to maintain the small diameter aspects of the guidewire 100 (i.e. arranged in a single file linear pattern along a predetermined length of the guidewire 100). In aspects, the microcircuit 130 may be encapsulated in a polymer bead, inserted into a protective tube, inserted into the core of a guidewire spring shank, etc.

In aspects, the microcircuit 130 may be coupled with one or more strengthening members so as to minimize the risk of damage to the coupling between the microcircuit 130 and the sensing tip 110 or the connectors 140. In aspects, the strengthening members may be configured to as to allow for compression, tension, and/or torque transfer through the region of the guidewire 100 that includes the microcircuit 130.

In aspects, the controller 120 may include one or more user inputs (e.g. buttons, foot pedals, sliding mechanisms, touch screen displays, etc.) for providing the controller with user guided input so as to adjust signal gain, deploy an aspect of a surgical tool, adjust a stimulation parameter, apply a stimulation, combinations thereof, or the like. In aspects, the controller 120 may include a display for providing a user with information relating to the physiologic signals, outcome of a procedure, an electrophysiological map, combinations thereof, or the like.

FIG. 1c shows aspects of methods for using a guidewire 100 in accordance with the present disclosure. Although the methods describe accessing the parenchyma of an organ, they could be equally adapted to measuring electrophysiological activity in vessels within a body (e.g. within arteries, veins, a ureter, a urethra, etc.), for accessing a miniature lumen within the body, etc. A first method 160 for diagnosing a medical condition is described that includes accessing the parenchyma of an organ. By accessing the parenchyma of an organ is meant coupling a sensor or electrode in accordance with the present disclosure with one or more anatomical sites within the parenchyma of an organ, so as to measure one or more physiologic signals therefrom. The first method 160 further includes recording physiologic activity from the parenchyma of the organ (e.g. with a sensor or electrode, a guidewire, a surgical tool, etc. each in accordance with the present disclosure), and monitoring a trend in the physiologic signal (e.g. during a stimulation event, during a stress test, etc.), and/or making a diagnosis or prognosis based upon the recorded signal (e.g. a diagnosis of a disease state associated with local physiologic activity in the parenchyma of the organ, making a prognosis relating to an outcome of a disease state associated with activity in the parenchyma of the organ, etc.).

In aspects, the first method 160 may include one or more additional steps in accordance with the present disclosure. In aspects, the first method 160 may include placing an additional tool including one or more sensors and/or electrodes at a remote location (with respect to the organ) in the body and stimulating the local anatomy at either the remote site or within the parenchyma of the organ and monitoring an evoked response within the parenchyma of the organ or at the remote site respectively. Such a configuration may be advantageous for elucidating information about the connectivity between the two sites (i.e. relevant to determining if a neuromodulation procedure applied there between has been successful, etc.).

A second method 170 is shown including accessing the parenchyma of an organ in accordance with the present disclosure. The second method 170 may further include recording physiologic activity from the parenchyma of the organ, performing a treatment on the body, recording a change in physiologic activity, and determining if the treatment was successfully applied. In aspects, the second method 170 may include one or more additional steps in accordance with the present disclosure.

A third method 180 is shown including accessing the parenchyma of an organ (alternatively an anatomical site of interest, a vessel, an artery, a vein, an arteriole, a venule, etc.), and mapping the electrophysiological activity in the vicinity of the anatomical site of interest. The mapping may be provided by sweeping a sensory tip in accordance with the present disclosure over the anatomical site of interest, inserting and then withdrawing the sensory tip, deploying the sensory tip and then dragging and/or rotating the deployed tip along/around the lumen wall, combinations thereof, and the like. In aspects, the third method 180 may include displaying the mapped physiologic information for a user, constructing an anatomical model therefrom, directing a surgical robot to perform a treatment therefrom, comparing the map with a previously determined map (e.g. as a means for monitoring the outcome of a procedure, tracking a therapy, etc.), combinations thereof, or the like. In aspects, the method may include providing one or more directions to a surgeon and/or a surgical robot to access one or more regions of the mapped anatomy, overlaying the present map with previously generated maps (so as to evaluate changes in functionality, activity, etc.), combinations thereof, and the like.

A fourth method 190 is described including accessing an anatomical site of interest within the parenchyma of an organ, stimulating one or more physiologic systems in the body, and monitoring the evoked response at the anatomical site of interest. The fourth method 190 may include assessing the functionality of the anatomical site of interest, the site of stimulation (i.e. if the stimulation is of a localized type), or an anatomical site there between.

In aspects, the method may include ablating one or more anatomical sites within the body.

In aspects, one or more methods in accordance with the present disclosure may be completed, at least in part, with a guidewire 100 in accordance with the present disclosure.

FIG. 1d shows a schematic of a sensing guidewire 102 in accordance with the present disclosure. The guidewire 102 may include one or more zones such as a sensing tip 112, a sensing/ablation/stimulation zone 114, and/or a second sensing zone 132 each located towards the distal end thereof. One or more of the zones may include aspects for sensing, ablating, stimulating, biasing against adjacent tissues, etc. In aspects, the sensing tip 112 may include one or more sensors and/or electrodes each in accordance with the present disclosure. In aspects, a second zone 114 may be configured to bias 137 one or more aspects of the guidewire 102 against an adjacent lumen wall for purposes of coupling thereto (such as to perform a procedure in accordance with the present disclosure, etc.). In aspects, a third zone 132 is shown, configured so as to interface with an adjacent lumen wall for purposes of sensing, ablation, stimulation, combinations thereof, or the like.

In aspects, the guidewire 102 may also include one or more connectors 142 in accordance with the present disclosure located at the proximal end thereof. The connectors 142 may be dimensioned and configured to interface with an interconnection module 138 or a controller 122. Although shown separately, the interconnection module 138 and the controller 122 may be integrated into a single unit. In aspects, a system in accordance with the present disclosure may include both an interconnection module 138 and a controller 122 coupled together by a cable 147.

In aspects, the optional interconnection module 138 may include one or more preamplifiers, multiplexers, switching networks, etc. each in accordance with the present disclosure. Such a configuration may be advantageous to minimize the length of leadwires between the sensing tip 112 and the first signal amplification stage (i.e. a preamplifier in the interconnection module 138).

In aspects, the guidewire 102 may include one or more microcircuits embedded therein (herein embedded within one or more of the zones 112, 114, 132). The microcircuits may be coupled with one or more elements within the sensing tip zone 112 as well as coupled to the connectors 142. The microcircuits may be dimensioned and configured to provide suitable preamplifier functionality, multiplexing operations, digital communication hardware, etc. in order to improve signal integrity from one or more elements within the sensing tip zone 112, to reduce lead wire count, etc. In aspects, the microcircuits may be coupled to elements of the sensing tip zone 112 using an ultra-high density interconnect technology as known in the art and/or in accordance with the present disclosure.

In aspects, one or more of the zones 112, 114, 132 may be configured so as to interface with an adjacent anatomical feature along which a treatment is desired. Information and/or treatment provided by each zone may be used to determine effective delivery of treatment to a region along the anatomical feature (i.e. physiologic sensing and/or stimulation provided at sites within zones 112, and 132 may be used to determine the effectiveness of a neuromodulation therapy provided to the adjacent tissues in the vicinity of zone 114). In aspects, a therapeutic, stimulatory, and/or sensing configuration may be coupled between zones 112, 114, 132.

In aspects, one or more steps of a method in accordance with the present disclosure may be performed with one or more zones 112, 114, 132 of a guidewire 102 in accordance with the present disclosure.

The connectors 142 may be dimensioned and configured to interface with an interconnection module 138 or a controller 122. Although shown separately, the interconnection module 138 and the controller 122 may be integrated into a single unit. In aspects, a system in accordance with the present disclosure may include both an interconnection module 138 and a controller 122 coupled together by a cable 147.

In aspects, the optional interconnection module 138 may include one or more preamplifiers, multiplexers, switching networks, etc. each in accordance with the present disclosure. Such a configuration may be advantageous to minimize the length of leadwires between the sensing tip 112 and the first signal amplification stage (i.e. a preamplifier in the interconnection module 138).

Figure 2K:
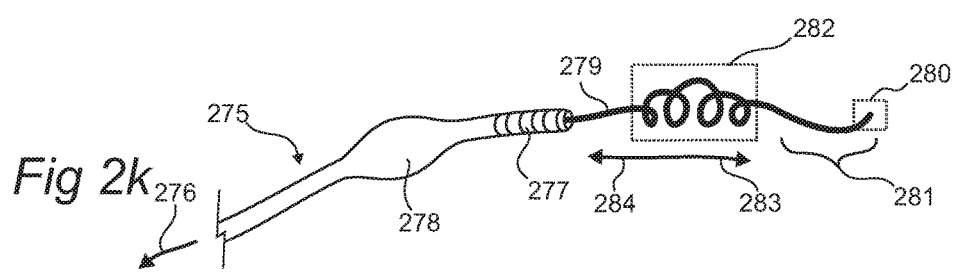
Figure 2L:
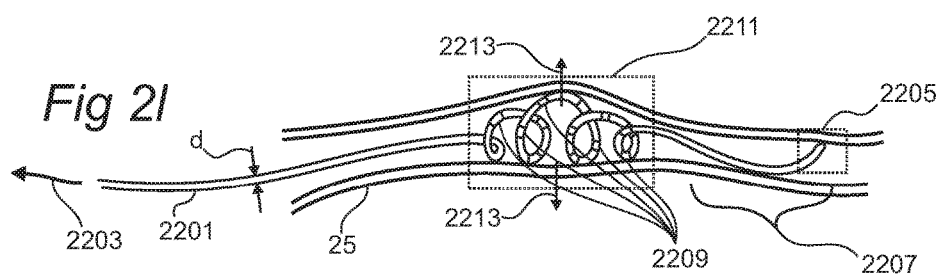
Figure 2M:
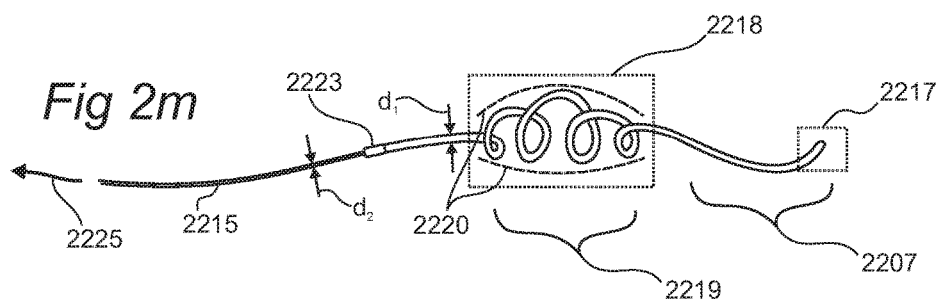
Figure 2N:
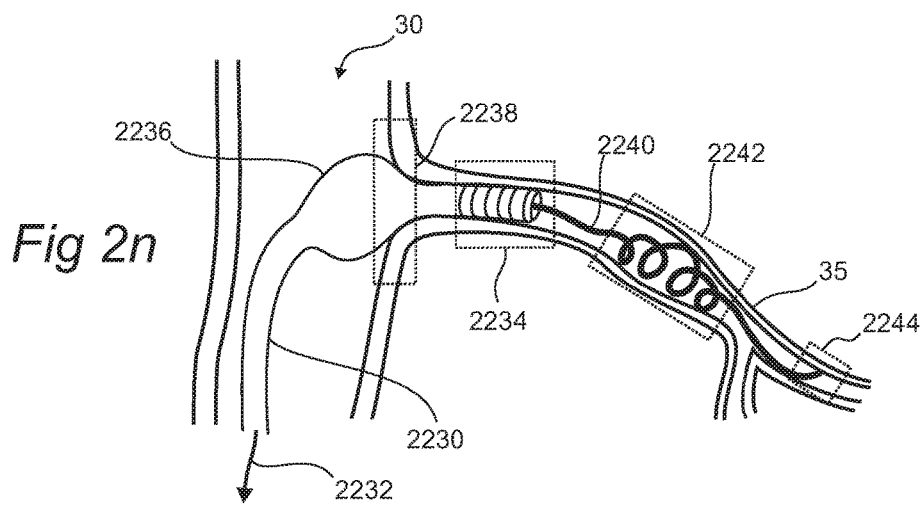
Figure 2O:
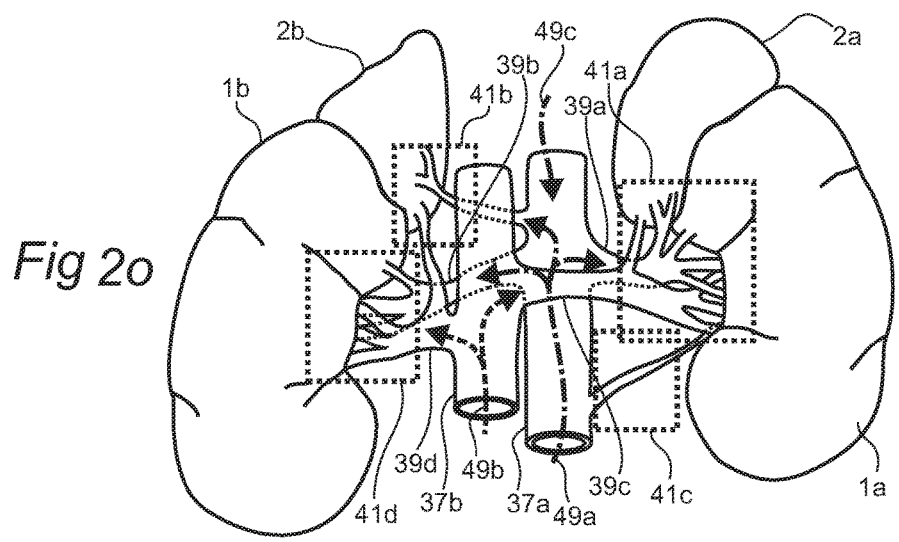
Figure 2P:
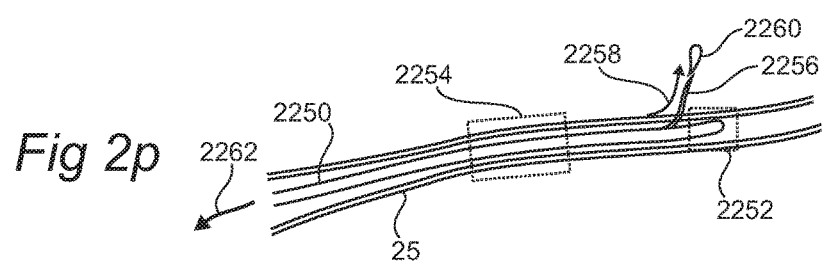

FIGS. 2a-p show aspects of sensing tips 110, and/or zones 112, 114, 132 associated with a sensing guidewire 100, 102 in accordance with the present disclosure. FIG. 2a shows a sensing guidewire 201 including one or more sensors or electrodes 202 located at the distal tip thereof. In aspects, the electrodes 202 may be arranged in patterns around the circumference of the tip so as to contact a lumen wall if the guidewire 201 is introduced deep enough into the lumen so as to bottom out (i.e. as the lumen diameter shrinks distally heading into the organ). The electrodes 202 may be connected to a controller 205, a preamp, a microcircuit, a connector, or the like in accordance with the present disclosure. Such interconnection may be provided by one or more leadwires 204 arranged along the length of the guidewire 201. In aspects, one or more of the leadwires 204 may be integrated into the walls or jacket of the guidewire 201. In such configurations, the leadwires 204 may be helically integrated, and/or braided into the walls or jacket, or equivalently threaded, coextruded, plated, shrink wrapped, or pultruded within the walls of the guidewire 201 (i.e. or equivalently threaded through one or more microlumen within the wall of the guidewire 201).

The electrodes 202 may be formed in accordance with the present disclosure. In aspects, the electrodes 202 may be formed directly from the tips of the one or more leadwires 204. The tips of the leadwires 204 may be formed into microelectrode elements, with predetermined exposed areas and tip profiles, suitable for monitoring electrophysiological activity at the site of interest. In aspects, the predetermined exposed areas may be designed so as to lean towards single unit recordings (e.g. electrode area less than 250 $\mu m^2$, less than 150 $\mu m^2$, less than 100 $\mu m^2$), multi-unit recordings (e.g. electrode area of greater than 500 $\mu m^2$, greater than 1000 $\mu m^2$, greater than 2000 $\mu m^2$), and large area or reference field recordings (e.g. electrode area greater than 10,000 $\mu m^2$, or the like). In aspects, the electrodes 202 may be treated so as to alter the impedance thereof, during use. In aspects, the electrodes may be processed so as to increase the capacity thereof such as via conversion to, plating of, or augmentation with an electric energy storage (EES) material, an intercalating material, surface area increasing process, a plating process, combinations thereof, or the like. In aspects, each electrode 202 may be configured with a profile suited for accessing the anatomy of interest (e.g. a needle-like structure, an embossed structure, a whisker like structure, a dendritic structure, etc.).

FIG. 2b illustrates aspects of a sensing tip of a guidewire 206 with a deployable tip array 208 arranged near to or at the distal tip thereof. Optionally, the guidewire 206 may include a jacket 207 arranged along the length thereof. The jacket 207 may be configured so as to slide along a core structure, the core structure supporting the deployable tip array 208. Thus, retraction of the jacket (or equivalently protrusion of the core structure) may be used to deploy the elements of the deployable tip array 208 once the tip of the guidewire 206 has been delivered to an anatomical site of interest. The deployable tip array 208 may include one or more microfingers 210 in accordance with the present disclosure. Each microfinger 210 may include one or more sensors or electrodes in accordance with the present disclosure. In FIG. 2b, a guidewire 206 is shown with an array of microfingers 210, each equipped with a microelectrode 209 upon the distal tip thereof. The microelectrodes 209 and microfingers 210 may be configured so as to bias towards a lumen wall upon deployment, or configured so as to penetrate the lumen wall upon deployment or during a penetrating maneuver (e.g. pushing the deployed tip array 208 forward along the lumen wall, etc.). In aspects, the microfingers 210 may be actuated so as to facilitate deployment (e.g. via an electroactive, electrochemical, mechanical, and/or thermomechanical activation means). In aspects, the microfingers 210 may be one-time deployable via a biodegradable mechanism (e.g. dissolution of an adhesive binding element, a thermally activated material, etc.).

In aspects, one or more of the microfingers 210 may be shaped such that it forms the desired shape upon deployment (subject to the dimensions of the local anatomy). In aspects, the microfingers 210 may be configured to form an umbrella like structure, a basket like structure, a helical structure, a star like structure, a porcupine like structure, etc.

One or more elements of the sensing tip may be interconnected with a controller 211, preamp, microcircuit, circuit, a connector, or the like in accordance with the present disclosure.

FIG. 2c shows aspects of a sensing tip of a guidewire 215 in accordance with the present disclosure. The sensing tip includes a j-curved segment 216 which may be configured with a subminiature bend radius. In aspects, the j-curved segment 216 may be formed with a radius of less than 4 mm, less than 3 mm, less than 1 mm. The sensing tip may include one or more electrodes 217, 218. As shown in FIG. 2c, the sensing tip may include one or more microelectrodes 217 and one or more reference electrodes 218 (optional). The microelectrode 217 may be exposed to the surroundings over a subset of the overall tip area (e.g. over an area most likely to bias against a lumen wall during insertion, over a region facing away from the axis of the j-curve segment 216, etc.). In aspects, the reference electrode 218 may be formed by exposing and/or processing a segment of the guidewire 215 (e.g. removing an insulating coating therefrom, plating a material thereto, swaging a tube onto the guidewire segment, etc.). The electrodes 217, 218 may be coupled to a connector and/or a controller 220, preamp, microcircuit, circuit, a connector, or the like in accordance with the present disclosure.

The j-curved segment 216 may be advantageous to maintain contact with the walls of a lumen during a placement procedure. In aspects, the j-curved segment 216 may be dimensioned with a predetermined radius and configured with a predetermined stiffness such that the electrodes 217, 218 may consistently contact the walls of vessels with a characteristic diameter within a predetermined range (e.g. 2-8 mm, 1-4 mm, 0.5-2 mm, etc.). The j-curved segment 216 may also be configured so as to bias 219 the electrodes against the wall of a lumen during a study.

In aspects, the j-curved segment 216 may include one or more strain measuring elements (e.g. a strain gauge, a piezoresistive material, etc.) configured to measure the diameter of the lumen into which the guidewire 215 has been placed.

FIG. 2d illustrates aspects of a sensing tip of a sensing guidewire 221 in accordance with the present disclosure. The guidewire 221 includes a pushable core 222 or equivalently a retractable sheath 223 configured so that the core can be deployed once the guidewire 221 has been directed to an anatomical site of interest. In aspects, one or more of the tip configurations disclosed herein may be attached to the pushable core 222 in order to construct a sensing guidewire 221 with a deployable 222a tip structure (e.g. with a deployable tip array, a basket arrangement, etc.). The pushable core 222 is also illustrated in a deployed position 224 to illustrate interfacing one or more electrodes there upon with a nearby anatomical site.

In aspects, the core 222 may be coupled with a controller 225, preamp, microcircuit, circuit, a connector, or the like each in accordance with the present disclosure.

FIG. 2e shows aspects of a sensing tip of a guidewire 226 in accordance with the present disclosure. The guidewire 226 includes a microbasket electrode array 227 including an array of microfingers 229, each arranged in a bowed shape so as to extend out from the axis of the lumen into which the device is placed. Aspects of a single microfinger 229 in the array is shown in the detailed view A. The microfinger 229 includes one or more sensors or electrodes 228, each in accordance with the present disclosure. In the example shown in FIG. 2e, the electrode 228 is shown patterned so as to face radially outwards from the center of the lumen into which the sensing tip is deployed. The electrode 228 may be formed in accordance with the present disclosure. One or more regions of the microfinger 229 may be isolated from the surroundings with an insulating layer (e.g. a passivated layer, a dielectric layer, a polymer, PTFE, parylene, etc.). In aspects, the microfinger 229 may be configured so as to deploy to reach the shape shown in FIG. 2e during a predetermined procedure (e.g. actuation, sheath retraction, core extension, biodegradation of a restraint, etc.). In aspects, the microbasket array 227 may be deployed during use so as to interface with the walls of a lumen, in accordance with the present disclosure. One or more microfingers 229 and/or sensors or electrodes 228 may be coupled with a connector or a controller 230, preamp, microcircuit, circuit, a connector, or the like each in accordance with the present disclosure.

FIG. 2f illustrates aspects of a sensing tip of a sensing guidewire 231 in accordance with the present disclosure. The guidewire generally includes one or more lumens and a microporous tip 232 which includes one or more ports 238 through which one or more protruding microneedle elements 234 may pass upon deployment. The guidewire 231 is shown in a retracted state 236 which may be suitable for accessing a target anatomical site in accordance with the present disclosure, as well as in a deployed state 237 which is suitable for interfacing one or more sensors or electrodes with the target anatomical site as part of a procedure. One or more of the protruding microneedle elements 234 may include a sensor or an electrode on the exposed tip 233 thereof. One or more of the microneedle elements 234 may include one or more features 235 such as bumps, step changes in insulation, etc. configured so as to limit the penetration depth of such exposed tips 233 into the adjacent tissues. One or more aspects of the guidewire 231 or aspects of the exposed tips 233 may be coupled to a controller 239, preamp, microcircuit, circuit, a connector, or the like each in accordance with the present disclosure.

FIG. 2g shows aspects of a sensing tip of a sensing guidewire 241 in accordance with the present disclosure. The sensing guidewire 241 includes a plurality of deployable tines 242, each tine 242 including one or more sensors and/or electrodes each in accordance with the present disclosure. The deployable tines 242 may be held together during storage and delivery to a surgical site of interest by a restraint mechanism 243 (such as a biodegradable adhesive, a water soluble matrix, a thermally stabilized shape set, etc.). Upon delivery to the anatomical site, upon contact with a fluid, etc. the restraint mechanism 243 may release the tines 242 so as to deploy 244 them to form a deployed state. In the deployed state, the tines 242 may be significantly biased 247 towards the walls of a lumen into which the sensing tip has been placed, etc. One or more aspects of the guidewire 241 or aspects of the tines 242 may be coupled to a controller 246, preamp, microcircuit, circuit, a connector, or the like each in accordance with the present disclosure.

FIG. 2h shows aspects of a sensing tip of a sensing guidewire 251 in accordance with the present disclosure. The sensing tip includes one or more microfingers 252 in accordance with the present disclosure. The microfingers 252 shown in FIG. 2h are equipped with a plurality of sensing points 253, each including a sensor or electrode in accordance with the present disclosure. The sensing guidewire 251 is shown placed within a lumen 25 within a body and the microfingers 252 have been deployed such that the sensing points 253 may interface with the walls of the lumen 25. One or more of the sensing points 253 may be coupled with a controller 254, preamp, microcircuit, circuit, a connector, or the like each in accordance with the present disclosure in order to record signals therefrom during a monitoring session. In aspects, the sensing guidewire 251 may be retracted while in the position shown so as to drag 255 the sensing points 253 along the walls of the lumen 25, so as to map the physiologic signals there upon. In aspects, such a configuration may be advantageous for mapping electrophysiological information along the lumen wall, for generating an anatomical map, for evaluating the location of active neuromuscular sites, evaluating the type and/or direction of neurological traffic in the vicinity of each sensing point 253, etc.

FIG. 2i illustrates aspects of a sensing tip of a sensing guidewire 260 in accordance with the present disclosure. The sensing tip includes a jacket 262 and a shaped tip 264, the jacket 262 dimensioned with a diameter 270 sufficiently small so as to access an anatomical site of interest within a body. The sensing tip further includes one or more sensors 266 each nested into an access port. The guidewire 260 also includes one or more lead wires 268 interconnected with the sensors 266 and the proximal end of the guidewire 260 (e.g. a connector, a microcircuit, a controller 272, a preamp, microcircuit, circuit, a connector, etc.).

In aspects, one or more of the sensors may be configured to monitor a local analyte concentration (e.g. a hormone concentration, norepinephrine, catecholamine, renin, angiotensin II, an ion concentration, a water level, an oxygen level, etc.), a pH level, etc.

FIG. 2j illustrates aspects of a delivery catheter 269 in accordance with the present disclosure. The delivery catheter 269 may provide a sheath through which one or more additional elements may be guided 272 to an anatomical site within the body and/or to interconnect a distal portion thereof with a controller 270, preamp, microcircuit, circuit, a connector, or the like. The delivery catheter 269 may include one or more electrodes 271 configured for purposes of sensing, stimulation, stress test analysis, neuromodulation, surgical procedural outcome, changes in traffic associated therewith, as reference electrodes, or the like. In aspects, the delivery catheter 269 may include a bulbous feature 273 sized and dimensioned so as to provide a stop gap for entrance into a target lumen, for providing hemostasis within a target lumen, etc.

FIG. 2k illustrates aspects of a delivery catheter 275 with a hollow lumen configured along the length thereof, including one or more sensors 277, a bulbous feature 278 each in accordance with the present disclosure. The delivery catheter 275 is shown with an associated guidewire 279, deployed from the tip thereof. The guidewire 279 includes one or more zones 280, 281, 282 each in accordance with the present disclosure. The guidewire 279 includes a sensing tip 280 attached to a soft guiding tip 281 configured so as to measure one or more physiologic aspects of an adjacent tissue when positioned within a lumen of a body. The guidewire 279 includes a biasing zone 282 including one or more electrodes and/or sensors, each in accordance with the present disclosure. In aspects, the biasing zone 282 may be configured to deploy upon protrusion of the guidewire 279 tip beyond the delivery catheter 275, upon retraction of the delivery catheter 275, upon actuation of an element within the biasing zone 282, upon adjustment of a repositionable core within the guidewire 279, or the like. The guidewire 279 may be configured so as to advance 283 or retreat 284 along the length of a lumen into which it is placed during a procedure.

In aspects, the guidewire 279 may include a repositionable core in order to construct a sensing guidewire 279 with a deployable tip structure (e.g. with a deployable tip array, a basket arrangement, helical biasing zone 282, etc.).

In aspects, one or more sensors and/or electrodes (i.e. included within 282, 280) on the guidewire 279 may be configured to communicate with one or more sensors and/or electrodes 277 on the delivery catheter 275.

FIG. 2l illustrates aspects of a guidewire 2201 in accordance with the present disclosure coupled with a lumen wall 25 into which it has been deployed (i.e. as part of a procedure). The guidewire 2201 may be coupled with a controller 2203 in accordance with the present disclosure. The guidewire 2201 may include one or more sensing tips 2205 for interfacing with the lumen wall 25. The guidewire 2201 may include a soft tip 2207 for assisting with delivery of the guidewire 2201 into the lumen. In aspects, the guidewire 2201 may include one or more electrodes 2209 positioned near to the distal tip of the guidewire 2201 within a biasing zone 2211 in accordance with the present disclosure. The biasing zone 2211 includes a helically shaped region (i.e. such as formed in a shape setting procedure, etc.), so as to bias the electrodes 2209 against the lumen wall 25 upon deployment.

In aspects, the guidewire 2201 may be configured with a characteristic diameter d, of less than 1.5 mm, less than 1 mm, less than 0.75 mm, less than 0.5 mm, less than 0.25 mm, or the like. The shape set aspects of the biased zone 2211 may be configured so as to transition from a disconnected region along the lumen wall 25 into a zone of contact, so as to provide consistent contact with the lumen wall 25 during a procedure. In aspects, the guidewire 2201 may be configured so as to transition from a substantially elongate shape to a deployed shape (e.g. a helical electrode arrangement, etc.), upon deployment into the lumen of a vessel within a body.

In aspects, the guidewire 2201 may be configured for placement within a vessel, for delivery to or within the parenchyma of an organ into which the vessel extends, or the like as part of a surgical procedure. In aspects, the guidewire 2201 may be configured for nerve monitoring, electrophysiological monitoring, stimulation, and/or ablation procedures in accordance with the present disclosure.

In aspects, the guidewire 2201 may be configured to provide a path, over which a second surgical tool may be delivered to the vessel, the guidewire sensing tip 2205 configured to monitor one or more physiologic functions relevant to the operation and/or evaluation of a procedure performed by the surgical tool.

In aspects, one or more of the zones 2205, 2211, etc. may be configured for sensing local electrophysiological activity, stimulating local neural anatomy, delivering a substance to local tissues, and/or neuromodulating local neural anatomy (e.g. ablating, denervating, etc.) in accordance with the present disclosure. In aspects, a guidewire in accordance with the present disclosure may include a sensing zone 2205 located at the distal tip thereof, an ablating/stimulating zone 2211 located along the length of the guidewire proximally to the distal tip, and a second sensing zone 132 shown in FIG. 1d located along the length of the guidewire proximally to the ablating/stimulating zone. In aspects, functions performed within each zone 112, 114, and 132 shown in FIG. 1d, 2201 and 2211 shown in FIG. 2l, etc. during a procedure may be coordinated by a controller in accordance with the present disclosure for purposes of diagnosis, determining the extent of a procedure, performing a neuromodulation procedure, denervating a neural structure, combinations thereof, or the like.

In aspects, the guidewire 2201 may be configured with a shape set region 2211, configured to bias 2213 one or more regions 2211 of the guidewire against a wall of a lumen 25 into which it has been placed. In aspects, the guidewire 2201 may include a wire basket, a helical region, a balloon, etc. in order to provide such bias 2213 against an adjacent lumen wall 25. In aspects, the shape set region 2211 may be retractably collapsible into a delivery sheath (i.e. a sheath provided over the guidewire sized and dimensioned for delivery thereof to an anatomical site of interest). In aspects, the shape set region 2211 may be deployed so as to bias against a wall of a lumen 25 into which it is placed by an actuation procedure, retraction of a delivery sheath, protrusion of the guidewire distal tip beyond the distal tip of a delivery sheath, etc.

In aspects, the biasing region 2213 may be deployed via actuation of an actuator element embedded therein. In aspects, such an actuator element may include an active material transducer in accordance with the present disclosure. In aspects, the actuation may be provided by a shape set shape memory alloy, such as may be introduced into the lumen at a temperature substantially below a threshold transition temperature, and undergo a deployment so as to bias against the lumen wall 25 upon increasing temperature to substantially above the threshold transition temperature (e.g. such as via natural heating from adjacent tissue structures, via active heating, via current flow associated with a stimulation and/or ablation procedure, etc.). In aspects, such deployment may be achieved by other forms of actuation such as but not limited to electroactive material expansion, retraction of a central core, pulling of a tendon core, retraction of a sheath, dissolution of a constraining element, etc.

In aspects, a guidewire in accordance with the present disclosure may include a bulbous feature located within the vicinity of the distal tip thereof. The bulbous feature may be configured to bottom out the guidewire within a lumen (e.g. when the lumen diameter approaches that of the bulbous feature, between a step between a feeding lumen and a treatment lumen, etc.) as it is advanced there along during a placement procedure. Such a feature may be advantageous to position the distal tip of the guidewire within a treatment lumen (e.g. a vessel, an artery, a vein, a tubule, etc.), to provide hemostasis to the treatment lumen, etc.

FIG. 2m illustrates aspects of a guidewire 2215 in accordance with the present disclosure. The guidewire 2215 may be coupled with a controller 2225 in accordance with the present disclosure. The guidewire 2215 may include one or more sensing tips 2217 for interfacing with a local anatomical site during a procedure. The guidewire 2215 may include a soft tip 2217 for assisting with delivery of the guidewire 2215 into a lumen within a body. In aspects, the guidewire 2215 may include one or more electrodes 2219 positioned near to the distal tip of the guidewire 2215 within a biasing zone 2218 in accordance with the present disclosure. The biasing zone 2218 shown in FIG. 2m includes a helically shaped region (e.g. such as formed in a shape setting procedure, etc.), so as to bias the electrodes 2219 against an adjacent wall during a procedure. In the biasing zone 2218 may take a deployed form 2220 during placement, or as part of a placement procedure. In aspects, the deployed form 2220 may take on a bulbous shape, an expanded region with tapered ends, a cylindrical profile, or the like.

In aspects, the biasing zone 2218 may include a shape set aspect, configured so as to transition from a first shape that is not sufficiently biased so as to contact an adjacent lumen wall, to a region over which the biasing is sufficient to provide consistent contact with an adjacent lumen wall during a procedure. In aspects, the biasing zone 2218 of the guidewire 2215 may be configured so as to transition from a substantially elongate shape to a deployed shape (e.g. a helical electrode arrangement, etc.), upon deployment into the lumen of a vessel within a body.

In aspects, the guidewire 2215 may be configured with one or more diameters along the length thereof. In aspects, a distal characteristic diameter d1, for the guidewire 2215 may be arranged such that d1 is less than 1.5 mm, less than 1 mm, less than 0.75 mm, less than 0.5 mm, less than 0.25 mm, or the like. In aspects, a proximal characteristic diameter d2 may be arranged such that d2 is less than 1.0 mm, less than 0.75 mm, less than 0.5 mm, less than 0.025 mm, or the like. In aspects, the proximal diameter d2 may be sized so as to provide a sufficiently miniature profile over which an additional catheter and/or surgical tool may be deployed within the body. In aspects, the distal characteristic diameter d2 may be configured so as to accommodate an embedded microcircuit 2223 and/or interconnections thereto.

In aspects, a guidewire 2215 in accordance with the present disclosure may include a microelectronic circuit 2223 embedded within or coupled to the distal tip 2217 thereof, as well as coupled to an interconnect and/or controller 2225 coupled to the proximal end thereof, configured to control signal flow to/from one or more zones 2218, 2217, etc. of the guidewire 2215 for purposes of performing a procedure in accordance with the present disclosure.

In aspects, a guidewire in accordance with the present disclosure may include one or more electrodes, each electrode configured to sense, stimulate, and/or ablate a local anatomical site within a body. In aspects, the guidewire may include a plurality of ablation electrodes configured to interface with a wall of a lumen into which the guidewire is placed, so as to provide coupling for delivery of radiofrequency, and/or microwave frequency energy into the wall of the lumen and/or tissues surrounding the lumen, as part of a procedure in accordance with the present disclosure. In aspects, the guidewire may be configured to monitor one or more physiologic aspects in conjunction with the energy delivery process (e.g. before, during, after, etc.).

In aspects, a system in accordance with the present disclosure may include a delivery catheter including one or more electrodes, and a guidewire including one or more electrodes, the system configured to pass energy between the catheter electrode(s) and the guidewire electrode(s) as part of a procedure. In aspects, the system may be configured to monitor electrophysiological activity between the guidewire electrode(s) and the catheter electrode(s) as part of a procedure.

In aspects, a guidewire in accordance with the present disclosure may include a drug eluting region (e.g. over an electrode, at the distal tip, etc.), configured so as to elute a drug into the vicinity of the region during a procedure (e.g. so as to minimize clotting, minimize damage to adjacent structures, etc.).

In aspects, a guidewire in accordance with the present disclosure may include a thrombus net coupled to the distal tip thereof. The thrombus net may be configured so as to bridge a cross section of a lumen into which the guidewire is placed during a procedure. The thrombus net may be configured to capture debris generated at a site along the system, guidewire, associated catheter, etc. during a procedure in accordance with the present disclosure. The thrombus net may be configured so as to withdraw any captured debris along with the guidewire during withdrawal from the body.

FIG. 2n illustrates aspects of placement of a delivery catheter 2230 and a guidewire 2240 each in accordance with the present disclosure placed within a body. The delivery catheter 2230 may include a bulbous feature 2236 to assist with placement thereof within a feeder lumen 30 and/or a treatment lumen 35 within the body. The delivery catheter 2230 may include a hollow core to facilitate delivery of an associated guidewire 2240 into the treatment lumen 35. In aspects, the guidewire 2240 may include a plurality of zones, such as a biasing zone 2242 for interfacing one or more electrodes/sensors, and/or a sensing tip zone 2244 with a wall of the target lumen 35. The delivery catheter 2230 and/or the guidewire 2240 may be interconnected with a controller 2232 in accordance with the present disclosure. In aspects, the delivery catheter 2230 may include one or more sensing, stimulation, and/or ablation zones 2234, 2238 in accordance with the present disclosure. In aspects, such a zone 2238 may be coupled to a bulbous feature 2236.

FIG. 2o shows non-limiting examples of aspects of a feeder lumen 37a,b, a main lumen 39a-d, and a variety of additional lumens 41*a-d*, which may be considered in the treatment of a disease state, analysis of traffic thereby during a stress test, a diagnostic procedure, a treatment, or the like. Such lumens may be accessed via one or more approaches 49*a-c* (e.g. via one or more access points into the body, a vascular access point, a venous access point, an arterial access point, etc.). In aspects, the main lumen 39*a-d* may be interconnected with one or more additional lumens 41*a, d*. In aspects, the feeder lumen 37*a,b* may be interconnected with one or more additional lumens 41*b, c*.

In aspects, one or more additional lumens 41*b,c* may not be easily accessed via the main lumen 39*a-d*. As such, an alternative approach (e.g. via an interconnected lumen, etc.), may be used to deliver a device in accordance with the present disclosure to the additional lumens 41*b,c*.

In aspects, a system, device, or method in accordance with the present disclosure may be used to treat a plurality of organs 1*a,b*, 2*a,b* (e.g. a kidney 1*a,b*, a adrenal gland 2*a,b*). A method in accordance with the present disclosure may include inserting at least a portion of a system or guidewire in accordance with the present disclosure into a main lumen 39*a-d*, or one or more additional lumens 41*a-d* and treating one or more regions there within. The method may include monitoring one or more physiologic signals, local electrophysiological signals, etc. to assess completion of the treatment, and/or to determine if further treatment sites are necessary to complete the intended procedure (such as a complete sympathectomy, controlled sympathectomy, etc.). In aspects, a method in accordance with the present disclosure may include withdrawing a portion of a system or guidewire in accordance with the present disclosure from a first lumen 39*a-d*, 41*a-d*, and delivering it into an alternative lumen and continuing with a procedure in accordance with the present disclosure.

In aspects, a method in accordance with the present disclosure may include treating one or more regions within or within the vicinity of one or more additional lumens 41*a-d* so as to ensure treatment has been completed.

In aspects, a method for treating hypertension is provided including treating neurological tissues running in the vicinity of a main lumen 39*a-d* and additional lumen 41*a-d* so as to substantially denervate all sympathetic and/or parasympathetic nerves coupled with the organ 1*a,b*, 2*a,b*. In aspects, the method may include treating the nerves coupled with the adrenal glands 2*a,b*.

In aspects, a method in accordance with the present disclosure may include locating one or more additional lumens 41*a-d*. In aspects, such locating may be performed with an imaging system (e.g. with a computed tomography system, HRCT, MRI, fMRI, positron emission tomography, ultrasound, OCT, combinations thereof, or the like) to produce one or more images (e.g. 2D images, 3D images, etc.) thereof and guiding a guidewire, device, etc. into one or more of the additional lumens 41*a-d*.

In aspects, the additional lumens 41*a-d* may be accessed by a guidewire and/or system in accordance with the present disclosure as part of such a procedure. In aspects, the additional lumens 41*a-d* may have a diameter of less than 2 mm, less than 1 mm, less than 0.5 mm, or the like. In aspects, a method may include delivering the tip of a guidewire in accordance with the present disclosure into one or more of the lumens 37*a,b*, 39*a-d*, 41*a-d* and assessing physiologic activity associated therewith, treating the nerves within the vicinity of the lumen(s) 37*a,b*, 39*a-d*, 41*a-d*, and assessing the extent of the treatment.

Such aspects may be applied to the treatment of one or more alternative disease states, or organs within the body. In aspects, a method, system, or guidewire, in accordance with the present disclosure may be used to assess the completion, response to, predict the response to, diagnose a disease state, etc. associated with neural traffic or neuroendocrine functions associated therewith in accordance with the present disclosure.

FIG. 2*p* illustrates aspects of a guidewire 2250 in accordance with the present disclosure placed within a lumen 25. The guidewire 2250 may include one or more zones 2254, 2252 in accordance with the present disclosure. The guidewire 2250 includes a sensing zone 2254 located along the length thereof for interfacing with the lumen wall proximally to a treatment site. The guidewire 2250 includes a sensing tip 2252 located at the distal tip thereof for interfacing with the lumen distally to a treatment site. The guidewire 2250 includes one or more microneedles 2256, which may be advanced from the body of the guidewire 2250 into the wall of the lumen 25 into which it has been placed as part of a procedure. Such needle advancement or retraction 2258 may be coordinated by an operator, a controller 2262, etc. In aspects, the microneedles 2256 may provide a means for delivering a chemical agent 2260 into the tissues surrounding the lumen 25. In aspects, the microneedles 2256 may include one or more electrodes to monitor and/or interface (e.g. stimulate, ablate, etc.) the local tissues upon deployment therein. In aspects, the guidewire 2250 may be configured so as to deliver the microneedles 2256 into the adventitia of the lumen 25, or optionally directly into the parenchyma of an organ to be treated. Such a configuration may be advantageous to provide a neurotoxin, a cancer treating agent, a neuroblocking agent, a neurostimulating agent, etc. into the target tissues as part of a treatment procedure in accordance with the present disclosure.

FIGS. 3*a-d* show aspects of a sensing guidewire in accordance with the present disclosure coupled with a second surgical tool or system for monitoring locations in a body before, during and/or after a procedure (e.g. surgical procedure, diagnostic procedure, signal assessment, etc.). FIG. 3*a* shows a sensing guidewire 301 with a sensing tip 303 each in accordance with the present disclosure. The sensing guidewire 301 is shown placed within the parenchyma of an organ 1 (in this case, a kidney), having been routed to the organ 1 via a lumen 5 (e.g. for purposes of discussion a renal artery 5, a vein 7, a ureter 9, etc.). The guidewire 301 may provide a path for the delivery of a second surgical tool, in this case a balloon catheter 309. The balloon catheter 309 may include a balloon with one or more energy delivery elements, electrodes 311 or the like, configured so as to provide stimulation and/or ablation to one or more anatomical sites adjacent to the lumen 5. Such stimulation and/or ablation processes performed by the catheter 309 may be coupled with one or more recording events (or stimulation events) performed with the guidewire 301.

In aspects, the balloon catheter 309 may be inserted into the body following the guidewire 301 until the balloon is placed within the lumen 5. The balloon may be inflated so as to bias one or more energy delivering elements 311 towards the wall of the lumen 5 as part of a treatment, a monitoring session, a stress test, etc.

In aspects, a balloon equipped with one or more electrodes 311 may be configured to deliver a stimulating and/or ablating current into the adjacent anatomy between one or more of the electrodes on the balloon and a remote electrode patch (not explicitly shown), so as to form a substantially radial current 313, or between two or more electrodes on the balloon to form substantially circumferential current 315, or longitudinal current 317. In aspects, physiologic response to the current 313, 315, 317 may be monitored by the guidewire 301. In aspects, the guidewire 301 may contribute current to the stimulation and/or ablation process. In aspects, the balloon may be used to ablate the surrounding anatomical sites and then to stimulate/sense with one or more of the proximally oriented electrodes, in conjunction with a sensing/stimulating event at the sensing tip of the guidewire 301. Such information may be used to determine the effectiveness of the ablation procedure, the functionality of the neurological structures between the guidewire 301 sensing tip 303 and the balloon electrodes 311, etc.

The guidewire 301 and/or the balloon catheter 309 may be coupled with a single controller 305, separate controllers, connectors, etc. so as to perform the intended tasks within the body.

The guidewire 301 may be configured such that the sensing tip 303 is placed along a region of interest 304 along the delivery route (e.g. such as near to the organ 1, within the parenchyma of the organ 1, along a vessel 5, 7, 9 coupled to the organ 1, etc.). In aspects, an alternative delivery route 312 is shown providing access to the renal pelvis for monitoring, ablation, etc. as part of a procedure in accordance with the present disclosure.

FIG. 3b illustrates a sensing guidewire 321 in accordance with the present disclosure having been advanced along a lumen 5 within a body to an anatomical site of interest 325 (in this case within the parenchyma of an organ 1). The guidewire 321 includes a sensing tip 323 in accordance with the present disclosure for acquiring one or more physiologic signals from the anatomical site of interest 325 during a procedure (e.g. surgical procedure, diagnostic procedure, signal assessment, etc.). The guidewire 321 may be placed along the path in site 325 as shown in order to capture signals relevant to the intended procedure. The guidewire 321 may be used to guide an ablation/stimulation tool 327 into the lumen 5 so as to properly position it to perform one or more stimulation and/or ablation events along the lumen 5 in accordance with the present disclosure. In aspects, the guidewire may include a stylet core, a stiffened element, etc. over which the second tool 327 may be advanced during placement. Retraction of the stylet may be used to alter the local stiffness of the guidewire 321 thus allowing the second tool 327 to take on a deployed shape (in this case a helical shape). Thus the second tool 327 may be deployed so as to interface one or more electrodes 329, needle delivery ports, included thereupon etc. with the tissues of the lumen wall 5 and the surrounding anatomy. As with the other coupled devices in accordance with the present disclosure, operation of the guidewire 321 and the second tool 327 may be coordinated so as to elucidate function of the local anatomy, the state of a surgical procedure, completion of a surgical procedure, diagnosis of a functional response to a stress test, etc.

The guidewire 321 and/or the second tool 327 may be coupled with a single controller 331, separate controllers, etc. so as to perform the intended tasks within the body. In aspects, the second tool 327 may be configured to deliver energy and/or a chemical substance to the adjacent tissues. Such energy delivery may be considered between elements on the second tool 327 or to a remotely coupled element, so as to apply energy radially 326 to, circumferentially 328 around, axially 322 along, the target region, lumen 5, etc. as part of a procedure (e.g. a stimulation procedure, stress test, surgical procedure, etc.).

The guidewire 321 may be configured such that the sensing tip 323 is placed along a region of interest 325 along the delivery route (such as near to the organ 1, within the parenchyma of the organ 1, along a vessel 5, 7, 9 coupled to the organ 1, etc.). In aspects, an alternative delivery route 324 is shown providing access to the renal pelvis for monitoring, ablation, etc. as part of a procedure in accordance with the present disclosure.

FIG. 3c shows a sensing guidewire 341 in accordance with the present disclosure having been advanced along a lumen 5 within a body to an anatomical site of interest 344 (in this case within the parenchyma of an organ 1). The guidewire 341 may include one or more sensing tips 343 in accordance with the present disclosure for acquiring one or more physiologic signals from the anatomical site of interest 344 during a procedure (e.g. surgical procedure, diagnostic procedure, signal assessment, etc.). The guidewire 341 has been positioned within the body of a subject and a needle catheter 345 has been directed along the guidewire 341 to a surgical site within the lumen 5. The needle catheter 345 may include one or more delivery needles 347, which may be deployed so as to interface with the anatomy in the vicinity of the lumen wall 5. In aspects, the delivery needles 347 may be hollow so as to administer a substance 350 (e.g. a fluid, a solid powder, or gel, a medicament, etc.) to the anatomy in and around the lumen wall 5. Such medicament 350 may be configured to alter functionality of the tissues in the vicinity of the lumen wall 5, to chemically ablate one or more neurological structures, etc. As with the other coupled devices in accordance with the present disclosure, operation of the guidewire 341 and the needle catheter 345 may be coordinated so as to elucidate function of the local anatomy, the state of a surgical procedure, extent of an ablation process, etc.

In aspects, the guidewire 341 may be left in place and the needle catheter 345 removed after delivery of the bolus of substance 350 to the walls of the lumen 5. After removal of the needle catheter 345, the guidewire 341 may be used to monitor for a prolonged period of time in order to identify if the substance 350 was properly delivered to the intended tissues (i.e. to determine if the neurological function returns after the intervention, or if the change in function has been relatively permanent in scope).

In aspects, the needle catheter 345 may include features 351 so as to limit the depth with which the delivery needles 347 may enter into the lumen wall 5 during deployment, as well as to gauge the depth at which a medicament 350 is delivered into the tissues. In aspects, the needle catheter 345 may include a plurality of delivery needles 347 so as to both stabilize the catheter 345 as well as to deliver medicament 350 to a plurality of locations within the adjacent tissues.

In aspects, the delivery needles 347 may include one or more electrodes 349 configured for stimulation, ablation, and/or sensing with each function being suitable for coordinating with the guidewire 341 during an interventional procedure.

The guidewire 341 and/or the needle catheter 345 may be coupled with a single controller 353, separate controllers, connectors, etc. so as to perform the intended tasks within the body.

The guidewire 341 may be configured such that the sensing tip 343 is placed along a region of interest 344 along the delivery route (such as near to the organ 1, within the parenchyma of the organ 1, along a vessel 5, 7, 9 coupled to the organ 1, etc.). In aspects, an alternative delivery route 342 is shown providing access to the renal pelvis for monitoring, ablation, etc. as part of a procedure in accordance with the present disclosure.

FIG. 3d shows a sensing guidewire 361 in accordance with the present disclosure having been advanced along a lumen 5 within a body to an anatomical site of interest 364 (in this case within the parenchyma of an organ 1). The guidewire 361 may include one or more sensing tips 363 in accordance with the present disclosure for acquiring one or more physiologic signals from the anatomical site of interest 364 during a procedure (e.g. surgical procedure, diagnostic procedure, signal assessment, etc.). The guidewire 361 has been positioned within the body of a subject and an ultrasound catheter 365 has been directed along the guidewire 361 to a surgical site within the lumen 5.

The ultrasound catheter 361, may include a balloon (as shown) or an energy directing element, configured so as to delivery and/or direct the delivery of ultrasonic energy 367 to one or more tissue sites surrounding the lumen 5 during a surgical procedure. In aspects, such ultrasonic energy 367 may be used to disrupt the regular neurological traffic there along, and/or to ablate the neurological anatomy located in the vicinity of the lumen 5.

In aspects, the ultrasound catheter 365 may include one or more electrodes configured for stimulation, ablation, and/or sensing with each function being suitable for coordinating with the guidewire 361 during an interventional procedure.

The guidewire 361 and/or the ultrasound catheter 365 may be coupled with a single controller 370, separate controllers, connectors, etc. so as to perform the intended tasks within the body.

As with the other coupled devices in accordance with the present disclosure, operation of the guidewire 361 and the ultrasound catheter 365 may be coordinated so as to elucidate function of the local anatomy, the state of a surgical procedure, extent of an ablation process, etc.

The guidewire 361 may be configured such that the sensing tip 363 is placed along a region of interest 364 along the delivery route (such as near to the organ 1, within the parenchyma of the organ 1, along a vessel 5, 7, 9 coupled to the organ 1, etc.). In aspects, an alternative delivery route 362 is shown providing access to the renal pelvis for monitoring, ablation, etc. as part of a procedure in accordance with the present disclosure.

FIGS. 4a-c show devices 400, 420, 440 in accordance with the present disclosure placed so as to monitor activity within an organ 1 within a body. FIG. 4a illustrates aspects of a monitoring device 400 including a sensing guidewire 401 with a sensing tip 403 each in accordance with the present disclosure. The sensing guidewire 401 may be configured and dimensioned for percutaneous placement (i.e. through the skin 11 of the subject) of the sensing tip 403 thereof into an organ 1 (i.e. in this case into the renal cortex 3 of the kidney 1) for monitoring one or more physiologic signals therefrom during a procedure (e.g. a monitoring procedure, a surgical procedure, etc.). In aspects, the guidewire 401 may be delivered through a cannula 405 (e.g. a polymer cannula, a hollow needle, etc.). In aspects, the cannula 405 may be inserted through the skin 11 using procedures similar to those used to place an intravenous cannula, an infusion set, or the like. In aspects, the placement procedure may be guided by an imaging system, an ultrasound probe, etc.

In aspects, the guidewire 401 may be coupled to an interconnection module 407 (e.g. a module including interconnects, and/or microcircuitry), thus providing electrical and/or optical communication between one or more sensors and/or electrodes in the sensing tip 403 with a controller 409 each in accordance with the present disclosure.

In aspects, one or more elements of the sensing tip 403 may be deployable once inserted within the organ 1. Such deployable aspects (e.g. deployable tines, microfingers, etc.) may be advantageous for maintaining the position of the sensing tip 403 within the organ 1 during use. In aspects, the sensing tip 403 may include a plurality of sensors or electrodes for capturing physiologic information from the organ 1 during the monitoring procedure.

FIG. 4b shows a device 420 for prolonged monitoring of physiologic parameters from an organ 1 in a body. The device 420 may be delivered percutaneously with the help of a delivery needle, biopsy needle, via a cannula, etc. The device 420 may include a sensing guidewire 421 with a sensing tip 423 each in accordance with the present disclosure. In aspects, the sensing guidewire 421 may be sufficiently flexible and/or stretchable so as to provide minimal stress at the anatomical site of interest during the monitoring period. In aspects, the sensing tip 423 may include one or more electrodes, microfingers, and/or sensors in accordance with the present disclosure. In aspects, one or more of the microfingers or electrodes may be hooked, anchored, and/or include one or more retaining aspects so as to maintain the position of the sensing tip 423 within the organ 1 during the monitoring period.

As shown in FIG. 4b, the guidewire 421 may be interconnected with a signal recording module 425. The signal recording module 425 is shown attached to the skin 11 with an adhesive 427. The signal recording module 425 may include one or more microcircuits configured to interface with the sensing tip 403 and generate one or more signals therefrom, suitable for transfer to an external unit (e.g. an interconnected controller, a wirelessly connected device, a network, a LAN, a WAN, a memory module for storage and later recall, etc.). In aspects the signal recording module 425 may be configured to translate the captured physiologic signals into a wireless signal 429 to communicate with a phone, a surgical control system, a hospital network, etc.

In aspects, one or more of the deployable and or retaining aspects of the sensing tip 423 may be reversible and/or biodegradable, such that the device 420 may be easily removed from the body after the monitoring period has been completed.

FIG. 4c illustrates aspects of a device 440 including an implantable module 441 and a signal recording module 445. The implantable module 441 may include one or more sensors and/or electrodes 443 each in accordance with the present disclosure. The implantable module 441 may include one or more microcircuits configured to accept power from an incoming energy source 451 or to harvest power from the surroundings (e.g. via kinetic, thermal gradient, pH gradient, enzymatic fuel cell, etc.) so as to power a preamplifier circuitry and to relay a wireless signal 449 back to the signal recording module 445, the wireless signal 449 relating to one or more physiologic aspects of the anatomical site of interest (e.g. within the organ 1, or within the body). In aspects, the energy source 451 may be transmitted by the signal recording module 445 in to the body for use in the monitoring process. In aspects, the signal recording module 445 may be secured to the skin 11 of the body with an adhesive interface 447.

In aspects, the implantable module 441 may be placed with a needle, a biopsy needle, via a cannula, optionally inserted through the skin 11 with ultrasound guidance, etc. In aspects, a plurality of implantable modules 441 may be placed at various sites within the body (e.g. within an organ 1, along a lumen wall 5, etc.) so as to capture spatially dependent information from the subject during the monitoring session.

In aspects, one or more of the devices 400, 420, 440 in accordance with the present disclosure may be used to monitor one or more physiologic parameters during a stress test in accordance with the present disclosure.

In aspects, the implantable module 441 may include one or more sensing tips in accordance with the present disclosure and a tether. The tether may include a fibrous cord to mechanically connect the interfacing portion to a location on the body (such as an entry port, a site on the skin 11, etc.). The tether may include means for electrically communicating between an externally placed device and the interfacing portion and/or sensing tips included therein. The tether may include a lubricous coating to substantially limit bonding between the tether and adjacent tissues during the placement period. The interfacing portion may be equipped to monitor one or more physiologic parameters of the adjacent anatomical structure for a prolonged period following placement.

The signal recording module 445 may include one or more microcircuits configured to interface with implanted module 441 and generate one or more signals therefrom, suitable for transfer to an external unit (e.g. an interconnected controller, a wirelessly connected device, a network, a LAN, a WAN, a memory module for storage and later recall, etc.). In aspects the signal recording module 445 may be configured to translate the captured physiologic signals into a wireless signal 452 to communicate with a phone, a surgical control system, a hospital network, etc.

FIGS. 5a-d illustrate aspects of a fiber based sensing guidewire 501 in accordance with the present disclosure. The guidewire 501 may include one or more fibers 503, arranged so as to form an array. In aspects, the fibers 503 may be semiconducting or conducting structures, suitable for electrically communicating between the tips thereof and a more proximally placed microcircuit, or connector suitable for coupling the fiber tips 507 to a controller 509 in accordance with the present disclosure. In aspects, the fibers 503 may be packed into a jacket 505. The jacket 505 may be biased towards the fibers 503 so as to provide the desired packing, but yet provide for longitudinal movement between the fibers 503 and the jacket 505 so as to allow for deployment of the fibers 503 as well as for maintaining a highly flexible guidewire 501. In aspects, one or more segments of the fibers 503 may be bonded together so as to provide structural rigidity, maintain unified movement of the bundle during deployment, provide tight seals along the jacket 505, etc.

In aspects, the jacket 505 may be formed from a microspring, an insulated microspring, a polymer sheath, an elastomer sheath, a shrink tube, a braided thin walled tube, etc.

In aspects, each fiber 503 may be electrically isolated from the others, so as to provide a series of sites (i.e. at fiber tips 507) in contact with the local anatomy for sensing one or more physiologic parameters. In aspects, the fibers 503 may be formed sufficiently small such that single through to multi-unit recordings may be made from the local anatomy within the subject.

Such a configuration may be advantageous for accessing very small anatomical sites of interest within the body but yet provide suitable mapping capability, or improve the prospects of obtaining viable signals from heterogeneously distributed neurological features given a high fiber tip 507 count.

In aspects, each fiber 503 may be held in close proximity to the other fibers 503 yet be only slidingly coupled thereto (i.e. so as to allow for movement of adjacent fibers with respect to each other). Such a configuration may be advantageous to improve the flexibility of the overall guidewire 501.

In aspects, such a configuration may provide improved magnetic field compatibility (for use within MIll guided surgical procedures), reduce heating of local tissues under a strong magnetic field, etc.

In aspects, the fibers 503 may be interfaced with an ultrahigh density interconnect, suitable for interfacing directly with each element of the bundle.

Figure 5A:
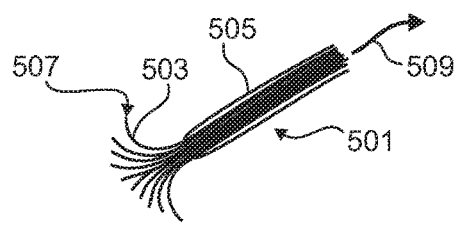
FIGS. 5a-d show aspects of a fiber based sensing guidewire in accordance with the present disclosure.
Figure 5B:
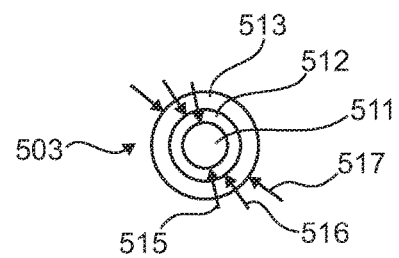

FIG. 5b shows aspects of a cross section of a fiber 503 in accordance with the present disclosure. The fiber 503 may include a conducting, resistive and/or semi-conductive core 511 (e.g. platinum, carbon, titanium, stainless steel, nickel titanium, silver, gold, spring steel, etc.). In aspects, the core 511 may be dimensioned with a diameter 515 of less than 25 µm, less than 12 µm, less than 7 µm, less than 5 µm, less than 2 µm, etc. In aspects, one or more segments of the core 511 may be covered with a clad layer 512. The clad layer 512 may include a passivating material, a highly conducting material, a bioactive material, etc. configured so as to isolate the core 511 from the surroundings, to improve the longitudinal conductivity of the core 511 (i.e. in the case of a metallic clad layer 512), provide unique analyte identification means (i.e. in the case of a bioactive clad layer 512, an enzymatic layer, etc.). In aspects, the clad layer 512 may result in a clad diameter 516 of less than 100 µm, less than 25 µm, less than 12 µm, less than 6 µm, less than 4 µm, etc. In aspects, the clad layer 512 may be thinner than 1 µm, thinner than 0.5 µm, thinner than 0.1 µm, etc. In aspects, the clad layer 512 may provide improved optical transmission down an optically oriented fiber 503.

In aspects, one or more segments of the clad layer 512 or the core 511 may be coated with an insulating layer 513. The insulating layer 513 may include a dielectric material, a thick walled polymer material, a ceramic, etc. The insulating layer 513 may be configured to enhance electrical isolation and/or reduce cross talk between fibers 503 over segments of the guidewire 501. In aspects, the insulating layer 513 may have a diameter 517 of less than 200 um, less than 100 um, less than 50 um, less than 25 um, less than 10 um, etc. In aspects, the insulating layer 513 may be provided with differing thickness (i.e. different overall fiber diameter 517) along alternative segments thereof. In one non limiting example, the insulating layer 513 is relatively thin near to the distal region of the guidewire 501 but increases in thickness in the proximal direction thereof.

In aspects, the clad layer 512 and/or the insulating layer 513 may be removed and/or otherwise not present over one or more segments of the fiber 503. Such a configuration may be advantageous for altering the flexibility, altering the intercommunication of the fibers 503, allow for interconnects between fibers 503, etc. over a particular segment of the guidewire 501.

In aspects, the clad layer 512, and/or the insulating layer 513 may be applied electrochemically to the core 511. In aspects, one or more of the layers 512, 513 may be applied via electrodeposition, a self-assembly process, a cataphoretic process, etc. In aspects, such a process may be used to form a highly uniform layer 512, 513 on the core 511.

Figure 5C:
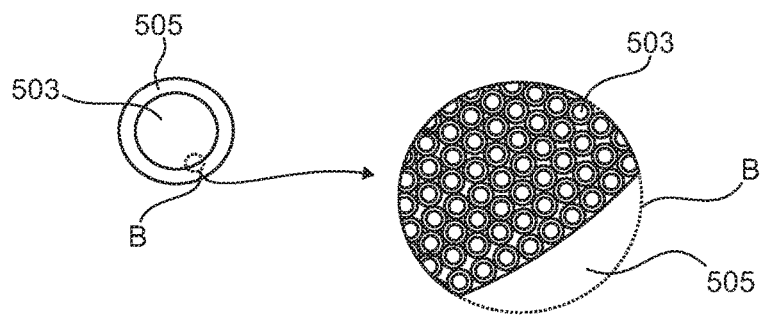

FIG. 5c shows aspects of a bundle of fibers 503 in accordance with the present disclosure configured near to the wall of the jacket 505 of the guidewire 501 in accordance with the present disclosure. A detailed image B is shown to highlight the arrangement within the guidewire. In aspects, such a configuration may provide for a highly flexible guidewire 501 including hundreds to thousands of fibers 503 for interfacing with the anatomical site of interest while maintaining an overall diameter and flexibility that allows for access to small vessels within a body (e.g. access into an organ parenchyma, small arteries, veins, large arterioles, large venules, etc.).

In aspects, the packing density of the fibers 503 may be provided so as to more easily interface with the fibers 503 near to the proximal end of the guidewire 501.

Figure 5D:
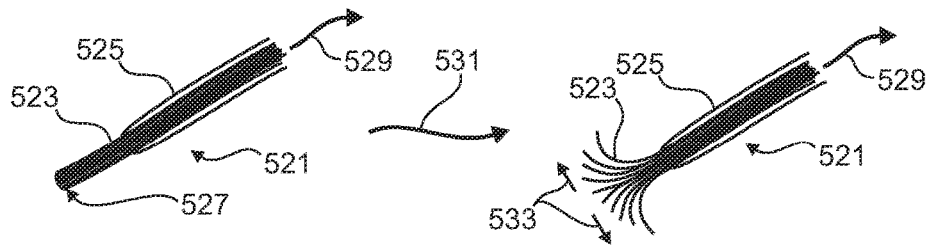

FIG. 5d shows aspects of a deployment mechanism for a fiber guidewire 521. The fiber guidewire 521 may include one or more fibers 523 and/or a jacket 525 each in accordance with the present disclosure. The fibers 523 may be configured into a bundle, representing the interior aspects of the guidewire 521. The jacket 525 may help to insulate and/or shield the fibers 523 from the surroundings during placement within a body. In aspects, the guidewire 521 and fibers 523 may be coupled with a connector, a microcircuit, a preamplifier, and/or a controller 529 in accordance with the present disclosure.

In aspects, the fibers 523 or a segment there along may be bonded together with temporarily restraining matrix 527 (e.g. a biodegradable matrix, an electrochemically degradable matrix, a water soluble matrix, etc.). Such a configuration may be advantageous for assisting with deployment 533 of the fibers 523 once the guidewire 521 has been placed near to the anatomical site of interest. Alternatively, additionally, or in combination, the jacket may be dimensioned and configured so as to be retractable for deployment of the fibers after placement (i.e. retractable so as to expose the fibers after delivery to the site of interest).

In aspects, the restraining matrix 527 may include a bolus of a stressing medicament (e.g. a neurostimulant, a neurodepressant, a vasodilator, a vasoconstrictor, a neuroblocking agent, glucose, insulin, etc.). In aspects, the bolus may be delivered into the organ 1 of the subject while the guidewire 521 monitors the associated physiologic response thereto at the site of interest.

FIGS. 6a-e show aspects of flexible multi-electrode guidewire tips 601a,b, 621, 661 in accordance with the present disclosure. FIG. 6a shows monolithic guidewire tips 601a,b including one or more tines 603a,b, each tine including one or more sensors and/or microelectrodes 605a,b each in accordance with the present disclosure configured for interfacing with an anatomical site of interest within a body. The guidewire tip 601a,b may be at least partially formed from a flexible substrate 607a,b in accordance with the present disclosure configured and dimensioned to form tines as well as provide electrical interconnection of components placed there upon, or integrated into the substrate 607a,b.

In aspects, the substrate 607a,b may include a flexible polymer, polyimide, PET, PEN, an elastic material, a silicone, an elastomer, an electroactive polymer, or the like known in the field of flexible electronics.

In aspects, the guidewire tip 601a,b may include one or more microcircuits 611a,b in accordance with the present disclosure. The microcircuits 611a,b may be configured to perform one or more functions such as signal routing, multiplexing, demultiplexing, preamplification, signal amplification, filtering processes, differential coupling to a reference electrode, signal conditioning function, analog to digital conversion, communication, power management, combinations thereof, and the like. The substrate 607a,b may include one or more conducting traces 609a,b placed so as to interconnect the sensors and/or electrodes 605a,b with the microcircuits 611a,b.

In aspects, one or more of the conducting traces 609a,b may include a metal, a meandering metal trace (i.e. so as to improve the flexibility or stretch capability thereof), an organic conductor, a printed structure, a physically deposited structure, or the like.

In aspects, one or more microelectrodes 605b may be formed at the extreme tip of a tine 603b. Such formation may be achieved by routing one or more traces 609b to the tip and severing the tip so as to expose only the most distal part of the trace 609b so as to form the interconnect for the microelectrode 605b. The interconnect may be plated with an interfacing material, such as a metal, platinum, a composite, a conjugated polymer, etc. so as to form the microelectrode 605b and so as to enhance coupling between the microelectrode 605b and a surrounding anatomical site of interest.

The substrate 607a,b may include interconnects for coupling with power and signal lead wires 613a,b. The microcircuit 611a,b may be configured to communicate with an outside communication module, a controller, or the like (not explicitly shown). In aspects, communication may be in the form of a bus protocol such as $I^2C$, 1-wire, SPI, serial, etc. In aspects, the lead wires 613 a,b may be configured and interconnected to power management hardware configured so as to provide power and signal communication along the same leads. Such a configuration may be advantageous to minimize the number of lead wires 613a,b within the guidewire.

After attachment of components (e.g. sensors, microcircuit(s) 611a,b, lead wires 613a,b, etc.) the substrate 607a,b may be rolled 615 to form a completed guidewire tip 617. FIG. 6b shows a completed guidewire tip 617 with an integrated jacket 619 coupled to the tip so as to reinforce the electrical interconnection of the substrate 607a,b, the lead wires 613 a,b, and/or the microcircuits 611a,b. In aspects, the jacket 619 may also provide increased electrical isolation between the microcircuits 611a,b, the traces 609a,b, the lead wire 607a,b interconnects, and the surroundings.

FIG. 6c illustrates a non-limiting example of a guidewire tip 621 with deployable tines 603. The tines 603 may be deployed from within a jacket 623 by retraction 625 of the jacket 623, advancement 627 of the tines 603 or a combination thereof. Such action will lead to deployment 629 of the tines 603 so as to monitor a physiologic parameter during a procedure in accordance with the present disclosure.

Two non-limiting examples of deployed configurations are shown in FIG. 6c, a configuration where the tips of the tines 603 are free and the set shape of the tines 603 results in a flower like formation upon deployment from the jacket 623. In aspects, the interconnects 631 on the substrate 607 may be dimensioned and/or encapsulated so as to form a soft seal against the jacket 623. Such a configuration may be advantageous to minimize fluid ingress to the guidewire during a procedure.

In aspects, the lead wires 603 may be coupled with a controller 630 in accordance with the present disclosure.

Another example of a deployed configuration is shown in FIG. 6c, a configuration where the tips of the tines 603 are held together with a restraining tip 635 so as to form a basket shape upon deployment 625. The basket may be retained in a jacket 639 of the device before deployment 625. In aspects, the restraining tip 635 may include an additional pull wire 632 configured such that relative movement of the pull wire may provide the forces necessary to deploy 625 the tines 603 (i.e. to convert the tines 603 from a collapsed shape to a basket-like shape).

In aspects, one or more of the tines 603 may be coupled with a microcircuit 637 in accordance with the present disclosure. The microcircuit 637 may be embedded into the device substantially near to the tines 603, within 400 mm thereof, 100 mm thereof, within 20 mm thereof, within 5 mm thereof, etc.

FIG. 6*d* illustrates a close up view of a tine 603 in accordance with the present disclosure. The tine 603 includes a plurality of electrodes 605 arranged along the tine 603 with a predetermined spacing 642. The tine 603 is constructed with a predetermined width 641, which may be tapered and/or otherwise shaped along the length of the tine 603. The tine 603 may include one or more traces 609 to interconnect the electrodes 605 with one or more microcircuits. The tine 603 may be generally constructed from a substrate 607 in accordance with the present disclosure. In aspects, the substrate 607 may be constructed from a laminate composite structure, including a base substrate, the traces, overcoats, etc. In aspects, the electrodes 605 may be configured so as to extend beyond the height of the substrate 607 such as by forming the electrodes 605 as bumps, generating whisker like features on the electrodes 605, plating the electrodes 605, etc.

FIG. 6*e* shows aspects of a guidewire tip 661 in an unraveled and a wrapped configuration. In the unraveled configuration the guidewire tip 661 may include one or more tines 651 formed from a substrate 652 shaped so as to form a tine envelope 655. One or more components on the tines interconnected with one or more chipset(s) 653 located at the root of the substrate 652. In aspects, the rolling process 657 may be used to arrange the tines 651 into a completed guidewire tip 661. Based upon the shape of the tine envelope 655, the tips and/or electrodes associated with the tines 651 may be positioned so as to interface with an elongate span of a lumen into which the guidewire tip 661 is placed. In aspects, the guidewire tip 661 may be formed into a guidewire with the addition of a jacket and/or a coil 663, etc.

FIGS. 7*a-b* show aspects of a guidewire 701 and surgical device 705 each in accordance with the present disclosure, positioned within an organ 1 within a body. FIG. 7*a* shows a guidewire 701 in accordance with the present disclosure. The guidewire 701 includes a sensing tip 703 in accordance with the present disclosure. The guidewire 701 is shown positioned such that the sensing tip 703 is coupled with an anatomical site of interest 13 (i.e. one or more sites along the renal pelvic wall, etc.). In aspects, the guidewire 701 may be configured to monitor afferent nerve traffic associated with the receptors lining the renal pelvic wall 13. An additional surgical device 705 is shown having been delivered to the organ 1 via the guidewire 701.

In FIG. 7*a* the surgical device 705 is a fluid exchange catheter, configured with a plurality of lumens so as to deliver fluid 709 and return fluid 711 to an external unit (not explicitly shown). The external unit may include a heating element so as to provide a warm fluid to be circulated through the surgical device 705 to the intended surgical site (in this non-limiting example, the renal pelvic wall). In aspects, the fluid delivery may be used to increase the temperature of the wall of the renal pelvis to more than 40° C., more than 50° C., more than 60° C. or the like. Such an operation may be advantageous for blunting the activity of the afferent nerves within the wall of the renal pelvis. In aspects, alternative surgical tools, ablation techniques, etc. may be implemented as part of the surgical procedure (i.e. an RF or microwave ablation instead of a hot fluid lavage). In aspects, the fluid delivery catheter may be configured to deliver a bolus of a neuroblocker, a neurostimulant, a neurodepressant, etc. In aspects, the fluid delivery catheter may be configured so as to provide a portion of a stress test for the organ 1 in accordance with the present disclosure.

In aspects, the surgical device 705 may include a balloon 707 to facilitate positioning, block off other regions of the body from a saline lavage, facilitate intimate contact with a lumen during a surgical procedure, combinations thereof, or the like.

In aspects, the guidewire 701 and/or surgical device 705 may be coupled with a controller 713, microcircuit, preamplifier, connector, or the like each in accordance with the present disclosure.

FIG. 7*b* illustrates aspects of a method for modulating afferent nerve traffic in accordance with the present disclosure. The method includes monitoring the afferent nerve activity, treating the afferent nerves and/or receptors, and evaluating the afferent nerve activity post treatment to determine if the traffic has been modulated. In aspects, the evaluation may be performed by comparing a nerve activity metric before and after treatment (e.g. a change in integrated activity level, a change in phasic response, a change in action potential firing rate, a change in the spectral content of the firing, etc.). In aspects, the method may include varying the pressure applied to the afferent nerves and/or receptors and monitoring afferent nerve activity during such changes.

Additionally, alternatively, or in combination with the monitoring of electrophysiological activity, the method may include monitoring one or more physiologic parameters in accordance with the present disclosure and assessing changes in the parameters before, during, or for a period of time following application of a procedure to the target tissues.

One or more of the steps may be completed with a guidewire or surgical tool in accordance with the present disclosure.

FIGS. 8*a-c* show aspects of a device in accordance with the present disclosure configured and dimensioned to interface with neural body (i.e. as shown in this non-limiting example, a carotid body 15). FIG. 8*a* shows a method for modulating functionality of, neural activity from, afferent activity from, or the like of a carotid body 15 of a subject, the method includes accessing the carotid body 15 and optionally monitoring activity at one or more sites 811 within or in the vicinity of the carotid body 15. In aspects, the method may include accessing regions near the surface of the carotid body 15, deep within the carotid body 15, etc. In aspects, the method may include selectively stimulating and/or stressing one or more regions of the carotid body 15 and monitoring the physiologic response at the sites 811 and/or systemically to the stimulus/stress. In aspects, the stimulus/stress response may be used to identify regions of the carotid body 15 that are suitable for neuromodulation to treat a particular condition. In aspects, the method may include selectively treating one or more sites 811 within or in the vicinity of the carotid body 15. In aspects, the method may include monitoring activity and/or local physiologic response to the treatment at one or more of the sites 811 to determine the extent of the procedure, to evaluate when the procedure has been completed, to decide whether or not to continue with the procedure, etc. The method may include ablating a portion of the carotid body 15, or a neurological structure coupled thereto, in accordance with the present disclosure. In aspects, the method may include using a guidewire and/or surgical device in accordance with the present disclosure to perform one or more of the above steps.

In aspects the method may include dragging one or more electrode arrays in accordance with the present disclosure along a lumen in the vicinity of the carotid body 15 in order to locate the body, locate neurological features of interest associated with the body, locate one or more baroreceptors, map activity thereof, map functional changes thereof due to application of a treatment or stress thereto, evaluate the function thereof, and/or treat one or more such structures.

FIG. 8*b* shows aspects of a surgical device 801 in accordance with the present disclosure. The surgical device 801 may be delivered to the carotid bifurication 19 within a subject through the common carotid artery 17 and positioned within the carotid bifurication 19, or along either of the external carotid artery 21 or the internal carotid artery 23 so as to access the carotid body 15 with one or more components thereof. The surgical device 801 may be configured so as to deploy one or more sensors and/or electrodes each in accordance with the present disclosure onto the wall of the artery 17, 21, 23 or through the wall of the artery 17, 21, 23 into the carotid body 15 or the tissues in the vicinity thereof. In aspects, the surgical device 801 may include one or more microneedle electrodes, fluid delivery needles, etc. each in accordance with the present disclosure so as to penetrate through the wall of the artery 17, 21, 23 and gain access to the carotid body 15. One or more elements within the surgical device 801 may be coupled with a connector and/or controller 802 at the proximal end thereof. The surgical device 801 may include a landing region 810 configured so as to retain a position along a wall of an adjacent lumen 17, 21, 23 during deployment, monitoring, etc.

During use of a surgical device 801 in a method in accordance with the present disclosure, the deployed tips 804 may be dragged 806 along the walls of the lumen 17, 21, 23 so as to map, locate, monitor, stress, stimulate, and/or treat one or more target tissues within the vicinity thereof.

FIG. 8*c* illustrates aspects of a surgical device 801 interfaced with the carotid body 15. The surgical device 801 includes a plurality of needle-like microfingers 804 in accordance with the present disclosure, each microfinger 804 may be tipped with a sensor and/or electrode each in accordance with the present disclosure. The microfingers 804 may be advanced 809 into the tissues around the carotid bifurication so as to couple one or more of the sensors and/or electrodes with the carotid body 15 thus creating one or more monitoring sites 811*a-e* within or around the carotid body 15. The device 801 may include a jacket 807 to alter the stiffness of one or more segments of the device 801, to protect the microfingers 804 of the sensing tip, etc. In aspects, the device 801 may include one or more stabilizing members 805 or balloon, configured so as to stabilize and/or orient one or more regions of device 801 near to the intended surgical site. Once stabilized, the microfingers 804 may be advanced towards the carotid body 15. In aspects, the device 801 may include one or more radiopaque markers, or may be constructed with one or more radiopaque materials in order to assist a surgeon with visualization of the surgical site during the procedure. In aspects, the stabilizing members 805 may be configured to limit relative motion between the microfinger tips (i.e. the electrodes) and the carotid body 15 during one or more surgical procedures performed thereon.

In aspects, the surgical device 801 may be used to monitor sites 811*a-e* within and around the carotid body 15 to assist in selectively ablating only a region of the carotid body (e.g. an outer layer, a surface, etc.). In aspects, the surgical device 801 may be used to both sense and selectively ablate regions of the carotid body 15. In such procedures, the sensing may be performed with or without stimulation/stress to determine the ideal locations within the carotid body 15 to perform neuromodulation. Upon determining the ideal locations, an RF current, a microbolus of neurotoxin, etc. may be injected into key sites amongst the monitoring sites 811*a-e*. Such a procedure may be advantageous for neuromodulating the carotid body 15 while limiting damage to surrounding structures, or to regions of the carotid body 15 that are to be spared in the procedure.

As shown in FIG. 8*c*, the neural body 15 (such as, in this non-limiting example, a carotid body) may be located in the vicinity of a main carotid artery 17, an internal carotid artery 21, or an external carotid artery 23. The surgical tool 801 may be configured for placement in a lumen 17, 21, 23 in the vicinity of the neural body 15 (i.e. in this case a carotid body), neurons coupled thereto 58*a,b*, and/or receptors 26 (i.e. in this case baroreceptors lining wall 25 of the internal carotid artery 21). In aspects, one or more elements of the tool 801 may be configured so as to be actuate-ably advanced 809 into the wall of the lumen 17, 21, 23, or into contact therewith so as to be advanced towards a target tissue 811*a-e* (e.g. one or more regions of the neural body 811*a*, a region adjacent to the neural body 811*d*, nerves and/or nerve plexuses coupled to the neural body 811*b,c*, and/or regions including receptors 811*e* in the vicinity of the neural body 15 and/or the walls 25 of the adjacent lumens 17, 21, 23, etc.

In aspects, one or more of the sensing tips 804 may be configured to stimulate, and/or treat one or more regions of the carotid body 15, and/or one or more target tissues 811*a-e* as part of a surgical procedure. The region of treatment as well as the extent of treatment may be monitored and/or controlled by a circuit coupled with one or more electrodes on one or more of the sensing tips 804.

In aspects, a probe or array of tips 804 in accordance with the present disclosure, including a plurality of electrodes may be configured to expandingly and/or sequentially treat regions 811*d* of the neural body 15, and/or surrounding target tissues 811*a-e*. In such a configuration, the treatment zone may be extended, starting from a first location as determined by the position of a first electrode and/or electrode pair, and may be simultaneously monitored by one or more surrounding electrodes on one or more of the tips 804, and/or an additional probe (not explicitly shown, alternatively placed within or near to the neural body 15, coupled to a neural structure attached to the neural body 15, etc.). As the neural activity changes in the vicinity of one or more of the alternative electrodes (as determined by simultaneous and/or sequential monitoring therefrom), the extent of an affected region as formed during the treatment may be tracked and the treatment may be halted at the appropriate time based upon the desired surgical extent of the process. In aspects, one or more of the electrodes may be incorporated into the treatment of the target tissues.

In aspects, one or more electrodes and/or sensing tips 804 may be configured to monitor, to stimulate, and/or to alter (e.g. deaden or block neural traffic, ablate the nerves, etc.), neurological activity in one or more nerve bundles 811*a,b* extending from the neural body 15. Changes in neural traffic after a surgical procedure, in response to a stimulus, or the like may be used to assist in controllably treating one or more regions of target tissue 811*d* in the neural body 15, or other target tissues 811*a-e* in the vicinity thereof.

Figure 9:
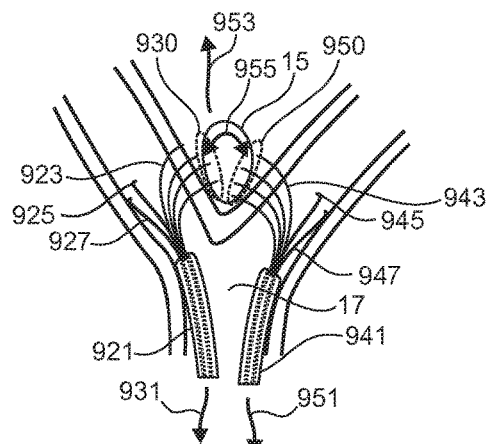
FIG. 9 shows aspects of a multi-tool based approach to monitoring and/or surgically interacting with a carotid body, in accordance with the present disclosure.

FIG. 9 shows aspects of a multi-tool based approach to monitoring and/or surgically interacting with a neural body (e.g. a carotid body 15), in accordance with the present disclosure. FIG. 9 shows a plurality of surgical tools 921, 941 after having been delivered to the carotid bifurcation via the common carotid artery 17 and positioned in the external and internal carotid arteries respectively. The surgical tools 921, 941 include stabilizing anchors 927, 947 which may be deployed first in order to orient the tools 921, 941 near to the carotid body 15. Once stabilized, one or more microfingers 923, 943 in accordance with the present disclosure may be advanced from the devices 921, 941 and onto/through the wall of the carotid bifurcation towards the carotid body 15. In aspects, one or more of the microfingers 927, 947 may include a sensor and/or electrode 925, 945 configured so as to interface with one or more monitoring sites 930, 950 within or in the vicinity of the carotid body 15. The surgical tools 921, 941 may be coupled with one or more controllers 931, 951 in accordance with the present disclosure to capture signals, provide fluids and/or current to one or more microfingers 923, 943, etc. as part of the surgical procedure.

In aspects, an RF current may be applied to one or more of the electrodes 925, 945 in order to treat the carotid body 15. In such aspects, the current may be passed between one or more of the electrodes 925, 945 and a remotely located electrode (not explicitly shown) or between 955 two or more of the electrodes 925, 945. Such a method may be advantageous for selectively controlling the current flow to the regions of the carotid body 15 in need of treatment. In aspects, the remotely located electrode may be a gel electrode placed upon the skin 11 of the body, a needle electrode, an electrode placed within a nearby vein, or the like.

Figure 10:
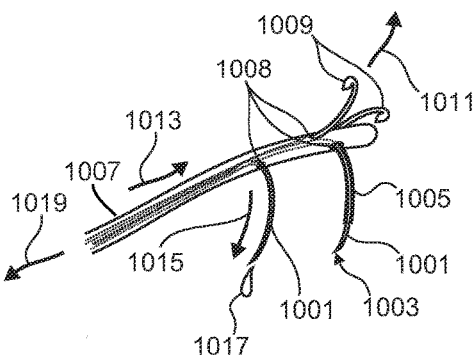
FIG. 10 shows aspects of a tool tip for use in a surgical tool in accordance with the present disclosure.

FIG. 10 shows aspects of a tool tip for use in a surgical tool in accordance with the present disclosure. The tool tip includes a jacket 1007 including a plurality of ports 1008 through which a plurality of microfingers 1001 and/or anchors 1009 in accordance with the present disclosure may pass through in order to couple with a local anatomical site of interest, to stabilize the tool tip, etc. The microfingers 1001 may include one or more electrodes 1003 and/or sensors at the tip thereof in order to interface with the local anatomical site of interest. In aspects, the microfingers 1001 may include an insulating layer 1005 configured so as to isolate one or more aspects of the microfinger 1001 from the surroundings. In aspects, the insulating layer 1005 may include a varying thickness, optionally arranged so as to form one or more step transitions along the length of the microfingers 1001. Such steps may be advantageous for limiting the depth of penetration of the microfingers 1001 into the local tissues.

In aspects, the microfingers 1001 may include a lumen through which to deliver 1017 a chemical substance, a medicament, etc. to the site of interest. Such microfingers 1001 may include one or more electrodes 1003 in order to monitor local electrophysiological activity before during and/or after the procedure.

In aspects, the stabilizing anchors 1009 may be shaped so as to bias against a lumen wall, to controllably position the tool tip within a lumen, etc. The tool tip may include a balloon for providing similar functionality. In aspects, the stabilizing anchors 1009 may be deployed in multiple directions (e.g. towards 1015, away from 1011, a site of interest, etc.).

In aspects, the microfingers 1003 and/or anchors 1009 may be slidingly coupled with the jacket 1007 such that they may be advanced 1013 as part of a deployment procedure. In aspects, the microfingers 1001 may be shaped such that, once stabilized with the anchors 1009, the microfingers 1001 may be advanced towards 1015 the surgical site of interest.

In aspects, the microfingers 1001 and/or stabilizing elements may be coupled with a connector, actuator, and/or a controller 1019 generally situated at the proximal end of the surgical tool.

Figure 11:
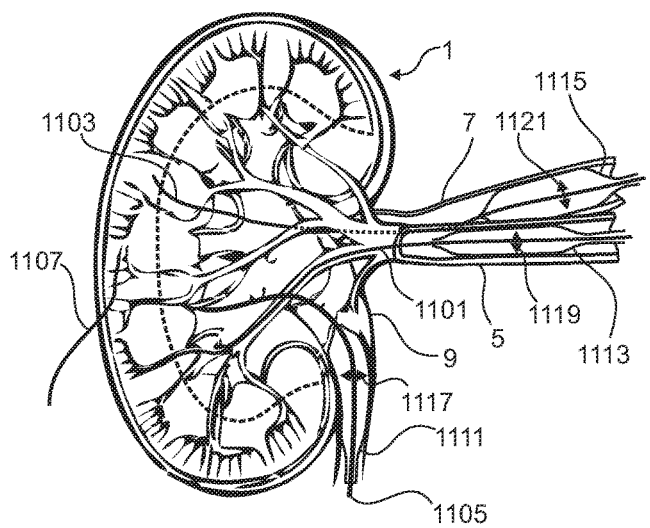
FIG. 11 illustrates aspects of coordinated multi-tool procedures being applied to an organ as well as highlights placement options for stressing an organ during a procedure in accordance with the present disclosure.

FIG. 11 illustrates aspects of coordinated multi-tool procedures being applied to an organ 1 as well as highlights placement options for stressing an organ 1 during a procedure in accordance with the present disclosure. FIG. 11 demonstrates placement of a sensing guidewire 1101, 1103, 1105 into a lumen 5, 7, 9 (e.g. an artery, a vein, a vessel, etc.) within a body so as to access an organ 1 as part of an interventional procedure (e.g. a transurethral procedure, a percutaneous procedure, etc.). The guidewire 1101, 1103, 1105 may include a sensing tip in accordance with the present disclosure. The sensing tip may be deployed as part of a monitoring/stimulating procedure, or the like. In aspects, the guidewire 1101, 1103, 1105 may be used in conjunction with an additional surgical device 1111, 1113, 1115 so as to couple multi-site monitoring and treatment modalities for the organ 1. Although FIG. 11 shows the additional surgical device 1111, 1113, 1115 as including a balloon, they may be of any variety of devices suitable for stimulating, stressing, and/or ablating tissues in the vicinity of the associated lumen 5, 7, 9.

In aspects, a sensing guidewire 1103 may be placed within a first lumen 7 (i.e. here shown as a renal vein), while an additional surgical device 1113 may be placed in a second lumen 5 (here shown as a renal artery). Coordinated procedures may be carried out with the dual devices in order to assess functionality of local neurological anatomy, treat local anatomy, determine if treatment has been completed successfully, etc.

In aspects, the additional device 1111, 1113, 1115 may be placed within the lumen 5, 7, 9 in order to apply a stress to the organ 1. In aspects, stress may be caused by blocking 1117, 1119, 1121 the lumen 5, 7, 9. In one non-limiting example, a balloon catheter 1115 placed into the lumen 7 in order to establish back pressure on the organ 1 during a monitoring procedure (e.g. with devices 1101, 1103, and/or 1105 monitoring sites of interest related to the organ 1). In aspects, a blocking procedure 1117, 1119, 1121 may be used in an artery 5 to relieve pressure on an organ 1, in a vein 7 to increase pressure in an organ 1 (i.e. to simulate vascular overloading) or within a function-related vessel 9 (i.e. a ureter) to alter pressure seen by receptors within the organ 1. Such combined stress testing and monitoring may be particularly useful in mapping function of the neurologically active tissues coupled to the organ 1, in selectively treating tissues coupled to the organ 1, etc.

Figure 12:
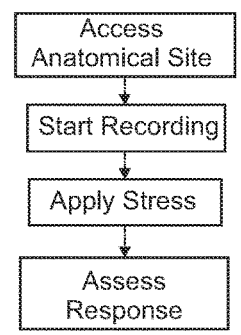
FIG. 12 shows aspects of a method for assessing an anatomical site within a body.

FIG. 12 shows aspects of a method for assessing an anatomical site within a body. The method includes accessing the anatomical site of interest within a body (e.g. neuroanatomical features extending to/from an organ, a parenchyma of an organ, a kidney, a liver, a pancreas, a spleen, etc.). The method includes recording one or more physiologic signals from the site and applying a stress test to the organ. In aspects the recording may be performed by one or more surgical tools and/or sensing guidewires in accordance with the present disclosure.

In aspects, the stress test may include releasing a medicament into the organ (i.e. from the blood supply thereto). Such a step may be performed by one or more sensing guidewires and/or surgical tools in accordance with the present disclosure.

The recording may be compared against a population norm, a response before/after a surgical procedure, a response between recording sites (i.e. so as to differentiate regions of sympathetic and parasympathetic innervation), etc.

In aspects, one or more stress tests may be applied to the organ or the subject in order to better evaluate and/or differentiate functionality at the monitoring sites.

Some non-limiting examples of stress tests that may be applied in a clinical and/or research setting include a valsalva maneuver, a tilt table test, elevating the legs of a subject, transient sitting to standing exercises, a change in posture, a movement from a prone position to a sitting or standing position, a breath hold technique, assessment while awake or asleep, assessment while awake versus under anesthesia, electrostimulation, combinations thereof, and the like. In aspects, the stress test may include infusion of a vasodilator (e.g. EDHF, potassium, nitric oxide, β-2 adrenergic receptors, histamine, prostacyclin, prostaglandin, vasoactive intestinal peptides, adenosine, ATP, ADP, L-arginine, bradykinin, substance P, niacin, $CO_2$, etc.), or a vasoconstrictor (e.g. ATP, muscarinic agents, acetylcholine, NPY, adrenergic agonists, epinephrine, norepinephrine, dopamine, thromboxane, endothelin, angiotensin II, asymmetric dimethylarginine, antidiuretic hormone, vasopressin, etc.), a neuroblocker, a neurostimulant, a diuretic, insulin, glucose, beta-adrenergic receptor antagonist, angiotensin-II converting enzyme inhibitor, calcium channel blocker, an HMG-CoA reductase inhibitor, digoxin, anticoagulants, diuretics, beta blockers, ACE inhibitors, one or more steroids (e.g. diflorasone, betamethasone, dexamethasone, clobetasol, prednisolone, mometasone, methylprednisolone, Deprodone, difluprednate, fluocinonide, amcinonide, triamcinolone, difluprednate, hydrocortisone, etc.), testosterone, or the like, into the body, into the organ, into one or more of the monitoring sites, etc.

In aspects, the stress test may involve the subject performing a physical activity (such as walking, running, etc.).

In aspects, the stress test may include altering the blood volume of the subject such as by infusion of a bolus of saline. In aspects, the stress test may include injecting a quantity of saline in to the body, such as 50 cc, 100 cc, 200 cc, more than 400 cc, etc. Such a technique may be advantageous for evaluating how the organ responds to the stress state, to assist with the diagnosis of a disease state, to evaluate the degree of stress-response in the local neurological features in the organ, etc. Such monitoring may be advantageous for evaluating the organ response under a moderate yet controlled state of stress, so as to evaluate how the central nervous system adapts to the stress state. In aspects, the peak activity during stress, the duration of elevated activity after a stress test, a comparison between baseline activity versus stressed activity, etc. may be useful for assisting with a diagnosis or to highlight abnormal function of a neurological system associated with the organ. In aspects, the blood volume may be altered by having the subject drink a bolus of fluid (e.g. water, electrolytes, etc.) and monitor response as the body processes the fluid load.

In aspects, the method may include comparing a result to that of a subject population, a previous test result, aspects within a single stress test, before and after a procedure, between a resting state and an active state, between an awakened state and a sleeping state, etc.

In aspects, the stress test may include altering the heartbeat of the subject, such as by pacing the heart out of sync with natural pacing centers (e.g. so as to lower blood pressure, to cause desynchronization of the tricuspid valve, etc.), or the like.

In aspects, the stress test may include inserting a balloon catheter into a lumen that serves the organ and blocking the lumen so as to alter the blood pressure, nutrient delivery, etc. to the organ while monitoring the organ response to such stresses.

In aspects, the stress test may include applying a polarizing potential to the anatomy in one or more vessels (e.g. so as to temporarily block traffic along the neurological features within the vicinity of the vessel, etc.). In aspects, the stress test may include applying a tension to the lumen wall.

In aspects, there is provided a system for assessing the local functionality of individual nerves in accordance with the present disclosure. The system includes a plurality of electrodes configured to interface with one or more vessels coupled with an organ of interest (e.g. a blood supply, lymph supply, general waste drainage tubes, an artery, a vein, etc.). The electrodes may be arranged so as to capture one or more physiologic signals from sites around the circumference of the walls of the lumen before, during, and/or after an organ stress test, so as to determine the local functionality of the neurological anatomy in the vicinity of each electrode. A stress test may include any of the ones listed above, delivery of a chemical to the organ via the placed device, etc. During the stress response, particular neurological features may exhibit distinct responses to the stress test (e.g. increased activity, decreased activity, changes in spectral response, changes in biorhythm synchronization, etc.), thus distinguishing the local function of the neurological features in the vicinity of the electrodes (i.e. to determine the degree of functionality related to a disease state near to each of the electrodes). Once determined, such information may be used to selectively ablate such tissues, so as to affect highly differentiated function (e.g. sympathetic or parasympathetic function, neurological features with responsiveness to particular stimulants, depressants, etc.) thereof. Such selective ablation may be advantageous for controllably modulating the innervation of the organ, adjusting the balance between contrasting neurological traffic (e.g. reduce traffic of a particular type, etc.).

Such a configuration may be advantageous for mapping and/or tracking a nerve structure in accordance with the present disclosure. A surgical tool in accordance with the present disclosure may be configured to interface with a nerve plexus. Based on monitoring and/or stimulation and sensing information, the surgical tool may be directed along the lumen wall to better target an overactive nerve. Such a configuration may be advantageous for tracking an overactive nerve along an organ, a vessel, etc. in order to find a more ideal location at which to ablate it. In the non-limiting example shown, a more distal location may be ideal for the ablation procedure, as less damage may be caused to surrounding nerves in the nerve bundle. Other relevant methods are highlighted throughout the present disclosure and may become apparent through reading of the present disclosure.

According to another aspect there is provided methods for performing aspects of a surgical procedure in accordance with the present disclosure including monitoring a physiologic signal at a first monitoring location (e.g. on an organ, on the wall of a vessel, etc.) to generate a first signal set, and monitoring a physiologic signal at a second monitoring location (e.g. on the organ, on the wall of the vessel, elsewhere in the body, etc.) and/or the first monitoring location to generate a second signal set. The method includes analyzing the signal sets to generate a result (e.g. a difference between the signal sets, a change in a set compared with a previous result, a patient population, etc.). The result may be compared against criteria to determine if a procedure should be performed or not. The procedure may be a surgical procedure, at least a portion of an ablation, stimulation, further monitoring, etc. The first comparison may be used to determine if the surgical procedure is having the intended effect on the tissues. The method may include another comparison to determine if the overall procedure is finished or not finished. In the case that the overall procedure is finished the method may include moving to another surgical site, stimulating an alternative tissue site, cleanup and/or removal of a surgical tool from the body, or the like. In the case that the procedure is not finished a procedure may be performed.

In aspects, the method may be performed with a surgical tool in accordance with the present disclosure.

In aspects, there is provided a method for locating a suitable surgical site on a body and performing a surgical procedure thereupon. The method may include stimulating a tissue location; monitoring one or more physiologic parameters at the tissue location or another location in the body; analyzing the stimulation and/or the monitoring to generate a result set (e.g. one or more parameters determined from the data sets associated with either the stimulation, and/or the monitoring, etc.). The method may include assessing the result set to decide if the location is suitable for performing a surgical procedure, if it is not then the system may move and/or assess an alternative location in the body. If the location is suitable for a surgical procedure then the method may include performing at least a portion of a surgical procedure thereupon and potentially repeat the overall process. The method may include determining from the result set if the surgical procedure has been completed, if so finalize the procedure, if not perform another procedure and/or move to a new location.

In aspects, the method may include moving to another surgical site, stimulating an alternative tissue site, cleanup and/or removal of a surgical tool from the body, or the like.

In aspects, steps of the method may be performed with a surgical tool in accordance with the present disclosure.

In aspects, the method may include performing at least part of a surgical procedure (e.g. ablation, chemical delivery, etc.), and monitoring at a location (e.g. the first location, an alternative location, etc.) to determine if the surgical procedure was successful.

Some non-limiting methods for performing a surgical procedure in accordance with the present disclosure are discussed herein.

In aspects, a method for addressing a surgical site on an organ in a body (e.g. a bowel wall, a stomach, a bladder, a liver, a spleen, a kidney, a gland, an artery, a vein, a renal artery, etc.) is considered. The method includes, monitoring one or more local physiologic signals (e.g. an evoked potential, extracellular activity, a neurological activity, MSNA, EMG, MMG, sympathetic tonal change, etc.) in accordance with the present disclosure at one or more measurement locations along an outer wall of the organ to determine one or more reference signals; performing at least a portion of a surgical procedure (e.g. an ablation, an excision, a cut, a burn, an RF ablation, an abrasion, a biopsy, delivery of a substance, etc.) in accordance with the present disclosure at or near to one or more surgical locations (e.g. proximal, distal, remotely therefrom, and/or collocated with one or more of the measurement locations); monitoring one or more local physiologic signals at one or more of the measurement locations to determine one or more updated signals; and comparing one or more reference signals with one or more updated signals to determine an extent of completion for the surgical procedure.

In aspects, the extent of completion may include a change, reduction and/or substantial elimination of at least a portion of one or more of the local physiologic signals (e.g. reduction in amplitude of a frequency band, reduction in responsiveness, a change in a lag between measurement locations, a change in cross-talk between measurement locations, substantial elimination of the signal, etc.).

The step of monitoring to determine an updated signal may be performed before, during, and/or after the step of performing at least a portion of the surgical procedure.

In aspects, the step of performing at least a portion of the surgical procedure may be repeated. Thus the method may be incrementally applied, so as to head towards completion in a stepwise process without excessive application of the surgical procedure.

In aspects, the method may include waiting after performing at least a portion of the surgical procedure. Monitoring may be performed during the waiting procedure, so as to determine a recovery period for the local physiologic signal (i.e. a time period over which the local physiologic signal recovers). Such a recovery period may be an indication of the extent of completion.

In aspects, the method may include stimulating one or more stimulation locations (proximal, distal, remotely therefrom, and/or collocated with one or more of the measurement locations and/or the surgical locations). The step of stimulating may be coordinated with the step of performing at least a portion of the surgical procedure, and/or with the step of monitoring to determine a reference and/or updated signal. The stimulation may be provided in any form in accordance with the present disclosure. In one non-limiting example, the stimulation may include one or more current pulses, one or more voltage pulses, combinations thereof, or the like. The step of stimulation may be advantageous for assessing the updated signal at one or more measurement locations and/or between two or more measurement locations in the presence of background noise and/or local physiologic activity.

The method may include monitoring one or more remote physiologic parameters in accordance with the present disclosure at a remote location (e.g. an alternative vessel, an organ, a ganglion, a nerve, etc.) substantially removed from the immediate vicinity of the vessel to determine an updated remote physiologic signal and/or reference remote physiologic signal.

Some non-limiting examples of remote physiologic parameters that may be monitored include water concentration, tone, blood oxygen saturation of local tissues, evoked potential, stimulation/sensing of nervous activity, electromyography, temperature, blood pressure, vasodilation, vessel wall stiffness, muscle sympathetic nerve activity (MSNA), central sympathetic drive (e.g. bursts per minute, bursts per heartbeat, etc.), tissue tone, blood flow (e.g. through an artery, through a renal artery), a blood flow differential signal (e.g. a significantly abnormal and or sudden change in blood flow within a structure of the body, a vessel, an organ, etc.), blood perfusion (e.g. to an organ, an eye, etc.), pupil dilation, a blood analyte level (e.g. a hormone concentration, norepinephrine, catecholamine, renin, angiotensin II, an ion concentration, a water level, an oxygen level, etc.), nerve traffic (e.g. post ganglionic nerve traffic in the peroneal nerve, celiac ganglion, superior mesenteric ganglion, aorticorenal ganglion, renal ganglion, and/or related nervous system structures), combinations thereof, and the like.

In aspects, the updated remote physiologic signal and/or reference remote physiologic signal may be combined and/ or compared with one or more reference signals, and/or one or more updated signals in order to determine the extent of completion.

In aspects, the method may include selecting a suitable site for performing a surgical procedure. The step of selection may depend upon one or more monitoring steps, proximity to an alternative surgical location (e.g. a previously treated surgical location, etc.).

According to aspects there is provided, a method for treating an anatomical site within a body, including imaging the anatomical site (e.g. with an computed tomography system, HRCT, MM, fMRI, positron emission tomography, ultrasound, OCT, combinations thereof, or the like) to produce one or more images (e.g. 2D images, 3D images, etc.) thereof, guiding a guidewire, device, and/or aspects of a system in accordance with the present disclosure to within the vicinity of the anatomical site (optionally in combination with the images), and performing a procedure, and/or treating the anatomical site (e.g. via ablation, chemical delivery, energy delivery, etc.). In aspects, the procedure may include sensing one or more physiologic aspects of the anatomical site and/or a bodily process related thereto, stimulating the anatomical site, etc.

In aspects, a method in accordance with the present disclosure may include advancing a guidewire in accordance with the present disclosure until it "bottoms out" against the walls of the lumen including and/or coupled to the anatomical site.

In aspects, a method in accordance with the present disclosure may include releasing a chemical substance in accordance with the present disclosure into, through the wall of, and/or into the adventitia around a lumen coupled with the anatomical site, and/or associated organ.

In aspects, a method in accordance with the present disclosure may include monitoring one or more physiologic processes with the distal tip of a guidewire in accordance with the present disclosure, before, during, and/or after the release of the chemical substance. The method may include assessing the efficacy of a procedure (e.g. ablation, chemical release, chemical ablation, RF ablation, ultrasound ablation, hypothermic ablation, microwave current ablation, radiosurgical ablation, etc.). In aspects, the method may include inducing a temporary neural block, monitoring the effects of the temporary neural block, and/or creating a substantially long term neural block depending on the monitoring.

In aspects, the steps of monitoring may be completed sequentially. Alternatively, additionally, or in combination, the steps of monitoring may be effectively continuously applied through the procedure. The comparison may be made using one or more data points obtained from one or more steps of monitoring. The comparison may be made via algorithmic combination of one or more measurements, a time averaged comparison, a convolution, or the like.

In aspects, the method may include determining a topographical map from the one or more measurements (e.g. from one or more of the signals). The method may include determining a topographical map of physiologic functionality in the vicinity of the surgical site derived from one or more of the physiologic signals. The method may include updating the topographical map after the step of performing at least a portion of the surgical procedure.

In aspects, the method may include placement of a plurality of surgical tools, one or more surgical tools (e.g. a procedural tool) placed so as to access one or more of the surgical locations, and one or more surgical tools (such as a monitoring tool) placed so as to access one or more of the monitoring locations. In one non-limiting example, a procedural tool may be placed upon a first organ (e.g. a bowel wall, a stomach wall, a kidney, a gland, a renal artery, a left renal artery, a renal vein, a ureter, etc.) and a monitoring tool may be placed upon or within a second organ (e.g. an opposing renal artery, a right renal artery, renal vein, a femoral artery, an iliac artery, etc.). Thus, the monitoring tool may be used to monitor one or more of the measurement locations on the second organ. The procedural tool may be used to surgically treat one or more surgical locations on the first organ. Additionally, alternatively, or in combination, the procedural tool may monitor one or more monitoring locations on the first organ, in combination with monitoring performed on the second organ by the monitoring tool, etc.

In aspects, one or more steps of the method may be performed with one or more surgical tools and or sensing guidewires in accordance with the present disclosure.

One or more steps of monitoring may be performed with one or more sensing tips in accordance with the present disclosure.

One or more steps of performing at least a portion of the surgical procedure may be performed with one or more sensing tips in accordance with the present disclosure.

In aspects, a method for RF ablating tissue in accordance with the present disclosure may include measuring the local tissue tone before, during, between individual RF pulses, and/or after a train of RF pulses. As the local tissue tone changes during application of the RF pulses, the tonal changes may be used to determine the extent of the therapy. As the RF ablation process is applied to the adjacent tissues (via one or more sensing tips), the tonal measurements (as determined by one or more sensing tips, the same tip through which the RF signal may be applied, etc.) may be monitored to determine an extent of completion of the procedure. Such an approach may be advantageous as the tonal measurement techniques may not be significantly affected by the local RF currents associated with the RF ablation procedure. The tonal measurements may be made at monitoring locations sufficiently far from the RF ablation zone that the local tissues under measurement are not directly affected by the RF ablation process but may undergo a change in tone as a consequence of the RF ablation process.

It will be appreciated that additional advantages and modifications will readily occur to those skilled in the art. Therefore, the disclosures presented herein and broader aspects thereof are not limited to the specific details and representative embodiments shown and described herein. Accordingly, many modifications, equivalents, and improvements may be included without departing from the spirit or scope of the general inventive concept as defined by the appended claims and their equivalents.

What is claimed is:

1. A guidewire, comprising:
   an elongate body dimensioned for insertion into a lumen within a body; and
   a sensing tip electrically and mechanically coupled to the elongate body, configured to interface with the wall of the lumen, the sensing tip configured to convey one or more electrophysiological signals associated with an electrophysiological activity in the vicinity of an anatomical site of interest within the vicinity of the lumen;
   wherein the guidewire is configured to monitor the electrophysiological activity;
   wherein the sensing tip comprises:
     a flexible substrate dimensioned to form a base and two or more tines extending from the base;
     a plurality of electrodes formed on the two or more tines of the flexible substrate;

one or more microcircuits formed on the base of the flexible substrate;

one or more conducting traces formed on the flexible substrate providing electrical interconnection between the one or more microcircuits and the plurality of electrodes; and one or more interconnects for coupling at least one of the one or more microcircuits formed on the base of the flexible substrate with one or more power and signal lead wires; and wherein the flexible substrate is rolled to form the sensing tip.

2. The guidewire in accordance with claim 1, wherein the plurality of electrodes are dimensioned and configured to interface with the anatomical site of interest upon placement thereby.

3. The guidewire in accordance with claim 1, wherein the plurality of electrodes are configured to measure one or more electrophysiological signals related to one or more of water concentration, tone, evoked potential, remote stimulation of nervous activity, an electromyographic signal, a mechanomyographic signal, a local field potential, an electroacoustic event, vasodilation, vessel wall stiffness, muscle sympathetic nerve activity, central sympathetic drive, tissue tone, nerve traffic, or combinations thereof.

4. The guidewire in accordance with claim 1, wherein the sensing tip is dimensioned and configured for placement into a parenchyma of an organ coupled with the lumen.

5. The guidewire in accordance with claim 4, wherein the sensing tip is dimensioned and configured for placement into at least one of a renal cortex of a kidney, an adrenal gland, an adrenal medulla, an adrenal cortex, and a renal pelvis of a kidney.

6. The guidewire in accordance with claim 1, wherein the sensing tip is configured such that at least one of the plurality of electrodes comprised therein is substantially isolated from a fluid within the lumen upon deployment of the sensing tip within the lumen by an isolation layer selectively applied to one or more regions of the sensing tip.

7. The guidewire in accordance with claim 1, wherein the sensing tip is configured such that at least one of the plurality of electrodes comprised therein maintains contact with a wall of the lumen during a procedure upon deployment of the sensing tip within the lumen.

8. The guidewire in accordance with claim 1, wherein at least one of the plurality of electrodes substantially maintains contact with the wall of the lumen while the sensing tip is dragged along the interior thereof, after deployment of the sensing tip within the lumen.

9. The guidewire in accordance with claim 1, wherein the sensing tip is configured such that at least one of the plurality of electrodes is embedded into a wall of the lumen upon deployment of the sensing tip within the lumen.

10. The guidewire in accordance with claim 1, wherein the guidewire is coupled to a second surgical device, the second surgical device configured to perform at least one of an ablation procedure and a stimulation procedure within the body.

11. The guidewire in accordance with claim 10, wherein the second surgical device provides a reference electrode electrically coupled with at least one of the plurality of electrodes comprised within the guidewire.

12. The guidewire in accordance with claim 1, wherein at least one of the microcircuits is configured to convey one or more sensed physiologic signals to a proximal end of the guidewire via the one or more power and signal lead wires.

13. The guidewire in accordance with claim 12, wherein at least one of the microcircuits is configured to condition one or more of the sensed physiologic signals measured by one or more of the plurality of electrodes prior to conveying the one or more sensed physiologic signals to the proximal end of the guidewire.

14. The guidewire in accordance with claim 12, wherein at least one of the microcircuits is configured to perform a digital conversion of one or more of the sensed physiologic signals measured by one or more of the plurality of electrodes prior to conveying the one or more sensed physiologic signals to the proximal end of the guidewire.

15. The guidewire in accordance with claim 12, wherein at least one of the microcircuits is configured to multiplex sensed physiologic signals from two or more of the plurality of electrodes comprised within the guidewire prior to conveying the sensed physiologic signals to the proximal end of the guidewire.

16. The guidewire in accordance with claim 1, wherein the guidewire further comprises one or more additional electrodes electrically and mechanically coupled with the elongate body, configured to deliver energy to the anatomical site of interest upon placement thereby.

17. The guidewire in accordance with claim 1, wherein the guidewire comprises one or more microneedles slidingly coupled with the elongate body, configured so as to be deployed beyond the elongate body into the anatomical site of interest upon placement thereby.

18. The guidewire in accordance with claim 17, wherein at least one of the one or more microneedles comprises a lumen through which a substance may be delivered to the anatomical site of interest upon deployment of the microneedle there into.

19. The guidewire in accordance with claim 18, wherein the substance is one of a neurotoxin, a cancer treating agent, a neuroblocking agent, a neurostimulating agent, a neurodepressant, a vasodilator, a vasoconstrictor, glucose, insulin, a combination thereof, and a formulation of the substance with a delivery vehicle.

20. The guidewire in accordance with claim 18, wherein at least one of the one or more microneedles comprises one or more electrodes for at least one of sensing, stimulating, and ablating the anatomical site of interest upon deployment of the microneedle there into.

21. The guidewire of claim 1, wherein the guidewire comprises a diameter one of less than 1 mm, less than 0.75 mm, less than 0.5 mm, and less than 0.25 mm.

22. A system for neuromodulating an anatomical site in a vicinity of a lumen, comprising:

a subsystem configured to perform a surgical procedure on the anatomical site;

a guidewire configured to monitor electrophysiological activity within a parenchyma of an organ coupled to the lumen and to generate one or more signals therefrom; and a control unit configured to accept signals from the guidewire, and to at least one of: adjust the surgical procedure dependent upon the signals; display the signals; evaluate the surgical procedure dependent upon the signals; plan a surgical path dependent upon the signals; and determine the extent of the procedure dependent upon the signals;

wherein the guidewire comprises:

an elongate body dimensioned for insertion into a lumen within a body; and a sensing tip electrically and mechanically coupled to the elongate body, configured to interface with the wall of the lumen, the sensing tip configured to convey one or more electrophysiological signals associated with an electrophysiological activity in the vicinity of an anatomical site of interest within the vicinity of the lumen;

wherein the sensing tip comprises:
- a flexible substrate dimensioned to form a base and two or more tines extending from the base;
- a plurality of electrodes formed on the two or more tines of the flexible substrate;
- one or more microcircuits formed on the base of the flexible substrate;
- one or more conducting traces formed on the flexible substrate providing electrical interconnection between the one or more microcircuits and the plurality of electrodes; and
- one or more interconnects for coupling at least one of the one or more microcircuits formed on the base of the flexible substrate with one or more power and signal lead wires; and wherein the flexible substrate is rolled to form the sensing tip.

23. The system in accordance with claim 22, wherein the surgical procedure is selected from the group consisting of an ablation, an excision, a cut, a burn, a radio frequency ablation, radiosurgery, an ultrasonic ablation, an abrasion, a biopsy, and delivery of a substance.

24. The system in accordance with claim 22, further comprising at least one of a stimulation electrode and an ablation electrode configured so as to convey at least one of a pulsatile frequency signal and a radio frequency signal to the anatomical site from the control unit, the guidewire configured to convey one or more feedback signals related to at least one of the pulsatile frequency signal and radio frequency signal back to the control unit.

25. The system in accordance with claim 24, wherein the one or more feedback signals are related to an electrode impedance, a bioimpedance, a local electrical field, or an electrophysiological response to at least one of the pulsatile frequency signal and radio frequency signal.

26. The system in accordance with claim 24, wherein at least one of the stimulation electrode and ablation electrode is comprised within the guidewire.

27. The system in accordance with claim 26, wherein at least one of the stimulation electrode and ablation electrode is comprised within the sensing tip of the guidewire.

28. The system in accordance with claim 22, wherein the subsystem is situated coaxially with the guidewire in the lumen.

29. The system in accordance with claim 22, further comprising a sensor, separate from the sensing tip, configured to measure one or more physiologic signals associated with a body comprising the lumen, and to convey the physiologic signals to the control unit for use in the procedure.

30. The system in accordance with claim 29, wherein the sensor is configured to measure one or more of water concentration, tone, blood oxygen saturation of local tissues, evoked potential, stimulation of nervous activity, sensing of nervous activity, electromyography, temperature, blood pressure, vasodilation, vessel wall stiffness, muscle sympathetic nerve activity (MSNA), central sympathetic drive, tissue tone, blood flow, a blood flow differential signal, blood perfusion, pupil dilation, electrolyte levels in a biofluid, a blood analyte level, nerve traffic, or a combination thereof.

31. The system of claim 22, wherein the subsystem is provided over the guidewire to perform the surgical procedure on the anatomical site.

* * * * *